(12) United States Patent
Ben-Haim et al.

(10) Patent No.: US 6,298,268 B1
(45) Date of Patent: Oct. 2, 2001

(54) CARDIAC OUTPUT CONTROLLER

(75) Inventors: Shlomo Ben-Haim; Nissim Darvish; Yuval Mika, all of Haifa; Maier Fenster, Petach Tikva, all of (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/254,902

(22) PCT Filed: Jul. 9, 1997

(86) PCT No.: PCT/IL97/00235

§ 371 Date: Mar. 12, 1999

§ 102(e) Date: Mar. 12, 1999

(87) PCT Pub. No.: WO98/10831

PCT Pub. Date: Mar. 19, 1998

Related U.S. Application Data

(60) Provisional application No. 60/026,392, filed on Sep. 16, 1996.

(51) Int. Cl.[7] .................................................... A61N 1/365
(52) U.S. Cl. ................................................................ 607/9
(58) Field of Search ............................ 607/4, 5, 9, 11, 607/68

(56) References Cited

U.S. PATENT DOCUMENTS

| 4,554,922 | 11/1985 | Prystowsky et al. . |
| 5,083,564 | 1/1992 | Scherlag . |
| 5,568,809 | 10/1996 | Ben-Haim . |
| 5,800,464 | 9/1998 | Kieval . |
| 5,814,079 | 9/1998 | Kieval . |
| 5,871,506 | 2/1999 | Mower . |

FOREIGN PATENT DOCUMENTS

| 0727241 | 8/1996 | (EP) . |
| WO 97/25098 | 7/1997 | (WO) . |
| WO 97/25101 | 7/1997 | (WO) . |
| WO 98/10828 | 3/1998 | (WO) . |
| WO 98/10829 | 3/1998 | (WO) . |
| WO 98/10830 | 3/1998 | (WO) . |
| WO 98/10832 | 3/1998 | (WO) . |

OTHER PUBLICATIONS

Morse et al., "A Guide to Cardiac Pacemakers, Defibrillators and Related Products", Droege Computing Services, Durham, NC.

Sutton and Bourgeois, "The Foundations of Cardiac pacing", p. 73.

H. Antoni, et al., Polarization Effects of Sinusoidal 50–Cycle Alternating Current on Membrane Potential of Mammalian Cardiac Fibres, Pflugers Arch. 314, pp. 274–291, (1970).

*Primary Examiner*—Jeffrey R. Jastrzab
(74) *Attorney, Agent, or Firm*—Cowan, Liebowitz & Latman, P.C.; William H. Deppert

(57) ABSTRACT

This invention is an apparatus for modifying cardiac output of the heart of a subject, including one or more sensors which sense signals responsive to cardiac activity, and a stimulation probe including one or more stimulation electrodes which apply non-excitatory stimulation pulses to a cardiac muscle segment. Signal generation circuitry is coupled to the one or more sensors and the stimulation probe, which circuitry receives the signals from the one or more sensors and generates the non-excitatory stimulation pulses responsive to the signals.

42 Claims, 50 Drawing Sheets

CARDIAC OUTPUT CONTROLLER

This application claims benefit of provisional application Ser. No. 60/026,392 filed Sep. 16, 1996.

FIELD OF THE INVENTION

The present invention relates generally to cardiac therapeutic devices, and specifically to invasive devices for enhancing performance of the heart.

BACKGROUND OF THE INVENTION

Cardiac insufficiency, characterized inter alia by a reduction in the cardiac output, is a common, well-known and well-documented heart malfunction. It develops as a result of congenital defects or as an end-effect of many diseases. Cardiac output, i.e., the output of the heart per unit time, is the product of stroke volume and heart rate. Hence, variations in cardiac output can be produced by chances in cardiac rate or stroke volume. The stroke volume can be influenced, for example, by changing the strength of cardiac contraction, by changing the length of the cardiac muscle fibers, and by changing contractility of cardiac muscle independent of fiber length. The heart rate and rhythm influence the cardiac output both directly and indirectly, since changes in the rate and rhythm also affect myocardial contractility.

The human body normally regulates the cardiac output in response to body needs by changing the heart rate, as during physical exercise, and/or by adapting the stroke volume. Under pathological conditions, however, some of the normal regulatory mechanisms may be damaged. For example, heart tissue damaged due to myocardial infarct typically cannot sustain normal pumping function, leading to a reduction in stroke volume, and hence of cardiac output. The body may react to such a reduction by increasing the heart rate, thus imposing long term strain on the heart muscles, leading in more severe cases to heart failure. There is thus a need for devices and treatments that can regulate the cardiac output, so as to compensate for the deficiencies in the normal regulation mechanisms.

In response to this need, modern cardiology has developed means to control various parameters associated with the heart's operation. Pharmaceuticals, for example, may be used to influence the conduction velocity, excitability, contractility and duration of the refractory period of the heart tissue. These pharmaceuticals are used to treat arrhythmia, enhance cardiac output and prevent fibrillation. Pharmaceuticals are generally limited in effectiveness in that they affect both healthy and diseased segments of the heart, usually, with a relatively low precision. They frequently also have unwanted side-effects.

A special kind of control can be achieved using implantable electronic devices, which provide excitatory electrical stimulation to the heart to control directly the heart rate and/or rhythm. For example, a pacemaker, an electronic devices which is typically implanted in the heart to support the heart's electrical excitation system or to bypass a blocked portion of the conduction system. Another type of cardiac electronic device is a defibrillator, which senses fibrillation in the heart and applies a high voltage impulse to "reset" the heart. While electronic pacemakers can control the heart rate, however, they are limited in their capacity to enhance cardiac output, and they are known to reduce stroke volume in at least some instances. Defibrillators are useful in treating arrhythmia when it occurs (although they are painful to the patient and traumatic to the heart), but they provide no long-term amelioration of cardiac insufficiency.

Thus, none of the treatments known in the art allow effective, long-term regulation of cardiac output. The electromechanical properties of the heart, as well as methods known in the art for influencing these properties, are more fully described in the "Background of the Invention" section of PCT patent application PCT/IL97/00012, which is assigned to the assignee of the present patent application and is incorporated herein by reference.

SUMMARY OF THE INVENTION

It is an object of the present invention to provide a device and method for regulation of hemodynamic parameters, and particularly for increasing the cardiac output by enhancing the heart's stroke volume.

In preferred embodiments of the present invention, a cardiac output controller comprises a non-excitatory stimulation probe, including one or more non-excitatory stimulation electrodes; at least one sensor, preferably a sensing electrode; and electronic control circuitry, coupled to the stimulation probe and sensor. The stimulation electrodes and, preferably, the sensor are implanted in the heart of a subject. Alternatively, a sensing electrode may be placed on a body surface. The circuitry receives signals from the sensor, indicative of the heart's activity, and responsive thereto, drives the stimulation electrodes to provide non-excitatory electrical stimulation to the heart.

The term "non-excitatory electrical stimulation," in the context of the present patent application and in the claims, refers to electrical pulses that do not induce new activation potentials to propagate in cardiac muscle cells. Rather, such pulses generally affect the response of the heart muscle to the action potentials, possibly by modulating cell contractility within selected segments of the cardiac muscle. Specifically, as described in the above-mentioned PCT patent application PCT/IL97/00012 and incorporated herein by reference, the inventors have found that by applying non-excitatory electrical stimulation pulses of suitable strength, appropriately timed with respect to the heart's electrical activation, the contraction of the selected segments can be increased or decreased, thus increasing or decreasing the stroke volume of the heart. This finding forms the basis for the present invention.

In preferred embodiments of the present invention, characteristics of the non-excitatory stimulation are adjusted so as to modify the heart's muscular activity, thus affecting the cardiac output, preferably by increasing the stroke volume, without directly affecting the heart rate. Preferably, the device is used to increase cardiac output substantially continuously for extended periods of time, most preferably to boost cardiac output during those portions of a day for which a patient needs increased blood supply. Accordingly, the device is preferably not used at night, to allow the heart muscle to rest.

Alternatively, the device may be used to modify the heart's muscular activity in other ways. For example, in some conditions, such as HOCM (hypertrophic obstructive cardiomyopathy), the device may be operated to reduce cardiac output, so as to reduce the workload on the heart, or particularly to reduce cardiac muscle contraction in a hypertrophic region of the heart. As another example, the device may be used to increase the heart's contraction efficiency, so that a given level of cardiac output is maintained at a reduced expenditure of energy. Such uses of the device are described further in a PCT patent application entitled, "Apparatus and Method for Controlling the Contractility of Muscles," filed on even date (Ser. No. 09/254994, which is assigned to the assignee of the present patent application, and whose disclosure is incorporated herein by reference.

In any case, the effect of the device on cardiac output is preferably regulated by changing the timing of the non-excitatory stimulation pulse relative to the heart's activity, preferably relative to the heart's local electrical activity or ECG signals received by the sensing electrode, and/or by changing other pulse characteristics, such as the voltage, current, duration, polarity, waveform and frequency of the waveform. Preferably, the device senses the heart's sinus rhythm and applies and synchronizes the stimulation pulse relative thereto, preferably with a delay before the onset of the stimulation pulse. Additionally, the circuitry may analyze the signals, for example, to determine the QT interval, so as to adjust the stimulation pulses responsive thereto. Alternatively, when the heart's rhythm is irregular, due to ventricular premature beats (VPB's) or other cardiac arrhythmias, the device preferably identifies and analyzes the irregularity, using signal processing methods known in the art, and adjusts or withholds the stimulation pulse accordingly.

In some preferred embodiments of the present invention the control circuitry is contained within a console external to the body, and the electrodes are fed percutaneously into the subject's vascular system, for example, through the femoral artery, and are implanted in the heart. Such embodiments are useful particularly in short-term therapy to regulate and stabilize the subject's hemodynamics following an insult or trauma, for example, open heart surgery or MI.

In alternative preferred embodiments of the present invention, the electronic control circuitry is contained within a miniaturized, implantable case, similar to pacemaker cases known in the art.

In some preferred embodiments of the present invention, the non-excitatory stimulation electrodes have a large surface area in contact with the heart tissue, by comparison with intracardiac electrodes known in the art, such as pacing, or electrophysiology electrodes. Preferably, the stimulation electrodes comprise large-area carbon electrodes, most preferably vitreous carbon, or alternatively, pyro-carbon. Both types of carbon materials are known for their compatibility with heart tissue, in-vivo durability and excellent electrical properties, including high electrical conductivity. Thus, they allow a relatively high electrical current to be delivered to a relatively large segment of the heart tissue, without inducing electrical excitation.

Alternatively, the non-excitatory stimulation electrodes may comprise large-area electrodes of other types known in the art, such as platinum or platinum/iridium.

In other preferred embodiments of the present invention, the non-excitatory stimulation electrodes are inserted into one of the blood vessels of the heart, preferably into the coronary sinus, or alternatively, into a coronary artery. These preferred embodiments are based on the inventors' experimental findings that cardiac output is most enhanced when the stimulation electrodes are placed in the heart adjacent to the blood vessels. In one such preferred embodiment, the non-excitatory stimulation probe comprises a carbon wire electrode, which is inserted into the coronary sinus and passed therein to a position adjacent the left ventricle.

In some preferred embodiments of the present invention the stimulation probe comprises a plurality of stimulation electrodes. Preferably, the probe comprises a stimulation net, which includes a plurality of interconnected, individually- and/or collectively- addressable electrodes, covering a substantial segment of the heart wall. As described in the above-mentioned '012 PCT application, the inventors have found that the extent of change in cardiac output, especially in left ventricular stroke volume, may be controlled by varying the size of the segment of the heart to which a non-excitatory field is applied. Such size variation is most preferably achieved by varying the number of the electrodes within the net that are to which the non-excitatory stimulation pulse is applied simultaneously.

In another preferred embodiment of this type, different stimulation pulses are applied to respective ones or groups of the plurality of stimulation electrodes. Preferably, the different stimulation pulses are applied to the respective electrodes with a predetermined delay between the different pulses. The delay may be varied so as to achieve a desired hemodynamic effect, for example, to maximize the increase in stroke volume.

In still other such preferred embodiments, the positions of the plurality of stimulation electrodes and/or characteristics of the stimulation pulses applied thereto are optimized responsive to clinical characteristics of the heart. Preferably, before insertion of the electrodes, a map of the heart is produced, for example, an electrophysiological map, as described in U.S. Pat. No. 5,568,809, or a phase-dependent geometrical map, as described in PCT Patent Application PCT/IL97/00011, both of which are incorporated herein by reference. Preferably, the map includes information regarding the viability of the heart tissue, for example, based on local contractility or electrical activity. The non-excitatory stimulation electrodes are then positioned responsive to the map.

Alternatively or additionally, at the time of implantation of the non-excitatory stimulation electrodes, their positions are varied and the results of the variation on hemodynamics are observed, in order to find optimal, fixed positions for the electrodes. A similar effect may be attained by implanting the net electrode, as described above, and variably addressing different ones or groups of electrodes in the net so as to optimize the hemodynamic effect.

In alternative embodiments of the present invention, the non-excitatory stimulation probe comprises at least one hybrid electrode. The hybrid electrode preferably comprises a sensing core, preferably a platinum or platinum/iridium electrode, surrounded by an annular non-excitatory stimulation electrode, preferably comprising a carbon electrode, as described above.

In still other embodiments of the present invention, a single electrode may serve as both the sensing electrode and as one of the one or more stimulation electrodes.

In some preferred embodiments of the present invention at least one non-excitatory stimulation electrode and the sensing electrode are implanted in the same chamber of the heart, preferably in the left ventricle. Preferably, the non-excitatory stimulation electrode is fixed against the wall of the left ventricle, and the sensing electrode is fixed at the septum thereof. Alternatively, the stimulation and sensing electrodes may be implanted in different chambers of the heart, in either the ventricles or the atria. The delay between the heart activity signal sensed by the sensing electrode and the pulse applied to the stimulation electrode is preferably dependent on the relative postions of these electrodes.

In some preferred embodiments of the present invention, the non-excitatory stimulation electrodes comprise a bipolar electrode, and the non-excitatory stimulation pulse is provided to the heart tissue between the poles of the electrode. In other preferred embodiments, the non-excitatory stimulation pulse is provided between the one or more stimulation electrode and another electrode, for example, the sensing electrode. Alternatively, the pulse may be applied between the stimulation electrodes and the case of the control circuitry, in those embodiments of the present invention in which the case is implanted in the patient's body, as described above.

In preferred embodiments of the present invention, the control circuitry applies to the stimulation electrodes a square wave stimulation pulse having current up to 50 mA, most preferably between 5 and 10 mA, for a duration that may be nearly as long as the beat-to-beat interval of the heart, most preferably between 30 and 50 msec. Preferably, the stimulation pulse is followed by a pulse of opposite polarity, to prevent problems of electrode degradation and polarization.

In some preferred embodiments of the present invention, an alternating waveform is superimposed on the square wave pulse. The waveform is itself preferably a square wave or, alternatively a sinusoidal or a sawtooth wave, having a frequency up to 10 kHz and amplitude less than or comparable to that of the square wave pulse. The inventors have found that in at least some cases, such a waveform enhances the hemodynamic effect of the non-excitatory stimulation pulse on the heart muscle.

In some preferred embodiments of the present invention, the control circuitry also receives a sensor signal indicative of hemodynamic conditions, preferably indicative of the cardiac output, and adjusts the stimulation pulse responsive to the signal to achieve a desired cardiac output level. Alternatively or additionally, physiological sensors may be used to sense other hemodynamic parameters, such as blood pressure or blood oxygenation, so as to provide feedback signals to the control circuitry or to telemetry apparatus associated with the control circuitry. Sensors used for this purpose may thus include flow rate sensors, pressure sensors, temperature sensors, oxygen sensors, and other types of sensors known in the art. The control circuitry then adjusts the stimulation pulse so that the hemodynamic parameters are maintained within a desired range of values.

Although preferred embodiments of the present invention are described for the most part with reference to sensing electrogram signals in the heart, so the cardiac output controller applies the non-excitatory stimulation pulse in response to and generally synchronized with the sinus rhythm, cardiac output controllers in accordance with the present invention may also be synchronized by other methods. For example, as described above, the non-excitatory stimulation pulse may be synchronized relative to a body-surface ECG, and may also be synchronized and controlled relative to an arrhythmic heart beat.

Alternatively, the pulse may be externally synchronized, for example by an externally-applied trigger pulse or by a pacing pulse that is applied to the heart. These aspects of the present invention are further described in a PCT patent application filed on even date, entitled "Cardiac Output Enhanced Pacemaker" Ser. No. 09/254,900, which is assigned to the assignee of the present application, and whose disclosure is incorporated herein by reference.

Preferred embodiments of the present invention may also be used in conjunction with suitable drugs, as described in a PCT patent application entitled "Drug-Device Combination for Controlling the Contractility of Muscles" Ser. No. 09/254,993, and in conjunction with devices and methods for preventing cardiac fibrillation, as described in a PCT patent application entitled "Fencing of Cardiac Muscles" Ser. No. 09/254,903, both filed on even date and assigned to the assignee of the present application. The disclosures of these applications are incorporated herein by reference.

There is therefore provided, in accordance with a preferred embodiment of the present invention, apparatus for modifying cardiac output of the heart of a subject, including:
one or more sensors, which sense signals responsive to cardiac activity;
a stimulation probe including one or more stimulation -electrodes, which apply non-excitatory stimulation pulses to a cardiac muscle segment; and
signal generation circuitry, coupled to the one or more sensors and the stimulation probe, which circuitry receives the signals from the one or more sensors and generates the non-excitatory stimulation pulses, responsive to the signals.

Preferably, the signal generation circuitry is contained in a unit external to the subject's body, or alternatively, in an implantable case.

Preferably, application of the stimulation pulses engenders an increase in the cardiac output, or alternatively, a decrease in the cardiac output.

Alternatively or additionally, application of the stimulation pulses increases an efficiency of contraction of the heart.

Preferably, the one or more sensors include a intracardiac electrode, and the signal generation circuitry synchronizes the stimulation pulse to electrical activity of the heart. Alternatively, the one or more sensors includes a body surface electrode, and the signal generation circuitry synchronizes the stimulation pulse to an ECG signal. Preferably, the signal generation circuitry identifies an arrhythmia in the signals and controls the stimulation pulses responsive thereto. Additionally or alternatively, the signal generation circuitry detects a QT interval in the signals and controls the stimulation pulses responsive thereto.

Preferably, the signal generation circuitry varies one or more parameters of the stimulation pulse, from the group of parameters including voltage, current, duration, timing delay, waveform and waveform frequency. After the non-excitatory stimulation pulse, the signal generation circuitry generates another pulse of opposite polarity to the stimulation pulse, which is applied to the cardiac muscle segment by the stimulation probe.

Preferably, the one or more stimulation electrodes apply the stimulation pulse to a heart segment having an area of at least 5 mm$^2$, more preferably at least 1 cm$^2$, and most preferably at least 4 cm$^2$.

In a preferred embodiment of the invention, the signal generation circuitry varies the area of the heart segment to which the stimulation pulse is applied. Preferably, the stimulation probe includes a net of electrodes, which are addressable such that an extent of the segment to which the stimulation pulses is applied is controlled by addressing selected electrodes in the net. Preferably, the circuitry applies multiple, different stimulation pulses, preferably a time sequence of pulses, to different ones of the electrodes in the net.

In another preferred embodiment of the invention, the stimulation probe includes a hybrid electrode, including the intracardiac electrode together with at least one of the one or more stimulation electrodes. Preferably, the hybrid electrode includes a core section including the sensing electrode, enclosed within an annular section including the at least one stimulation electrode, wherein the annular section preferably includes a carbon material.

In still another preferred embodiment, the one or more stimulation electrodes include an elongate electrode, which is inserted into a blood vessel of the heart.

Preferably, the one or more stimulation electrodes include vitreous carbon or, alternatively, pyrolitic carbon.

In a preferred embodiment of the invention the one or more sensors include a hemodynamic sensor, which generates signals responsive to a hemodynamic parameter. Preferably, the hemodynamic sensor generates the signals responsive to blood flow. Alternatively or additionally, the hemodynamic sensor generates the signals responsive to blood oxygenation and/or temperature. Preferably, the one or more sensors include an electrode, which senses cardiac electrical activity.

Preferably, the apparatus includes a telemetry device, which receives the signals from at least one of the one or more sensors and controls the signal generation circuitry to adjust the non-excitatory stimulation pulse.

There is further provided, in accordance with a preferred embodiment of the present invention, a method for modifying cardiac output, including:

applying a stimulation probe including one or more stimulation electrodes to a subject's heart;

receiving a signal from at least one sensor responsive to the subject's cardiac muscle activity;

generating a non-excitatory stimulation pulse responsive to the signal and conveying the pulse to at least one of the one or more electrodes.

Preferably, receiving the signal includes introducing a sensing electrode into the heart and receiving signals therefrom, and generating the stimulation pulse includes generating a pulse synchronized with electrical activity sensed by the sensing electrode.

Alternatively or additionally, receiving the signal includes applying an electrode to a body surface and receiving signals therefrom, and wherein generating the stimulation pulse includes generating a pulse synchronized with an ECG signal.

Further alternatively or additionally, receiving the signal includes receiving signals from at least one of the one or more stimulation electrodes.

Preferably, generating the stimulation pulse includes generating a pulse having a predetermined delay relative to the signal.

In a preferred embodiment of the invention, applying the stimulation probe includes applying a probe including a plurality of stimulation electrodes, and generating and conveying the pulse includes generating a sequence of pulses and applying each pulse in the sequence to a different one of the plurality of stimulation electrodes.

Preferably, generating and conveying the stimulation pulse includes generating and conveying stimulation pulses selectively, based on a characteristic of the signals received from the at least one sensor. Further preferably, generating and conveying the pulses includes generating and applying pulses at a rate dependent on the heart rate, but not equal to the heart rate. Alternatively or additionally, generating and conveying the pulses includes detecting a cardiac arrhythmia and adjusting the application of the pulses responsive thereto. Further additionally or alternatively, generating and conveying the pulses comprises detecting a QT interval in the signals and generating pulses responsive thereto.

Preferably, generating the non-excitatory stimulation pulse includes varying one or more parameters of the pulse, selected from the group including the pulse voltage, current, duration, delay, waveform and waveform frequency.

Further preferably, the pulse includes a baseline pulse and a waveform, preferably a square wave, of substantially higher frequency than the baseline pulse superimposed thereon. Preferably, after generating the non-excitatory stimulation pulse another pulse of opposite polarity thereto is generated and conveyed to the electrodes.

In a preferred embodiment of the invention, applying the non-excitatory stimulation pulse includes varying the extent of a portion of the area of the heart segment to which the stimulation pulse is applied, wherein varying the extent preferably includes selectively addressing a net of stimulation electrodes implanted in the heart.

In another preferred embodiment, applying the stimulation probe includes inserting the one or more stimulation electrodes in multiple chambers of the heart.

In still another preferred embodiment, implanting the stimulation probe includes inserting at least one of the one or more stimulation electrodes into a blood vessel of the heart, preferably into the coronary sinus.

In a preferred embodiment of the invention, receiving the signal includes sensing a hemodynamic parameter, preferably sensing cardiac output, wherein generating the pulse preferably includes changing the pulse responsive to the signal to increase the cardiac output, or alternatively, to decrease the cardiac output.

Alternatively or additionally, sensing the hemodynamic parameter includes sensing a pressure and/or a flow rate and/or oxygenation and/or a temperature.

In another preferred embodiment of the invention, generating and conveying the pulse includes generating and conveying pulses at selected times of day, preferably conveying pulses to increase cardiac output during the subject's waking hours.

Preferably, generating and conveying the pulses includes generating and conveying pulses which increase the subject's cardiac output, or alternatively decrease the subject's cardiac output. Further alternatively or additionally, generating and conveying the pulses includes generating and conveying pulses which increase the efficiency of contraction of the heart.

Preferably, conveying the pulses includes applying pulses to a heart segment having an area of at least 5 $mm^2$, more preferably at least 1 $cm^2$, and most preferably at least 4 $cm^2$.

The present invention will be more fully understood from the following detailed description of the preferred embodiments thereof, taken together with the drawings in which:

DETAILED DESCRIPTION OF PREFERRED EMBODIMENTS

Figure 1A:
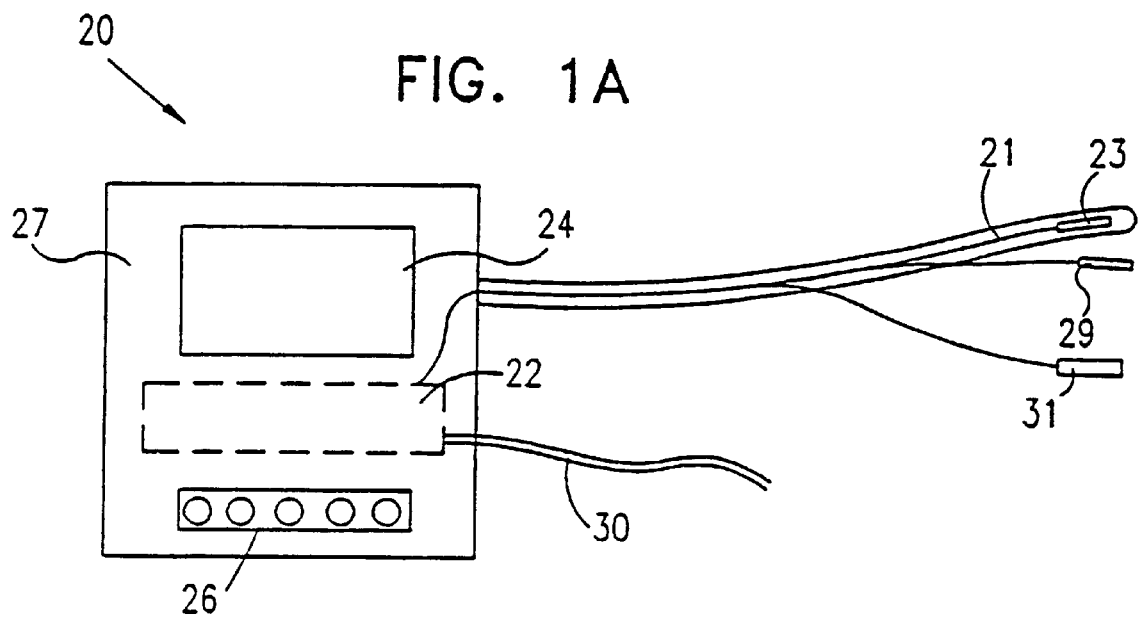
FIG. 1A is a schematic illustration showing a device for controlling cardiac output, in accordance with a preferred embodiment of the present invention.

FIG. 1A schematically illustrates a device 20 for regulating cardiac output, comprising a control unit 27, an implantable non-excitatory stimulation probe 21, including at least one non-excitatory stimulation electrode 23, and an implantable sensing electrode 29. Control unit 27 includes signal generation circuitry 22 (shown in FIG. 3 below and described with reference thereto), as well as an optional display 24 and a control panel 26. When properly implanted in the heart, as described below, sensing electrode 29 receives local electrogram signals from the heart muscle and transmits them to the signal generation circuitry 22. The circuitry generates a non-excitatory stimulation pulse responsive to the electrogram signal, which pulse is applied by probe 21 to cardiac muscle tissue. Control unit 27 optionally also includes an external trigger input 30. Device 20 may further include another physiological sensor 31, for example, a flow sensor, for determining the effect of the stimulation provided by the device on the cardiac output.

Figure 1B:
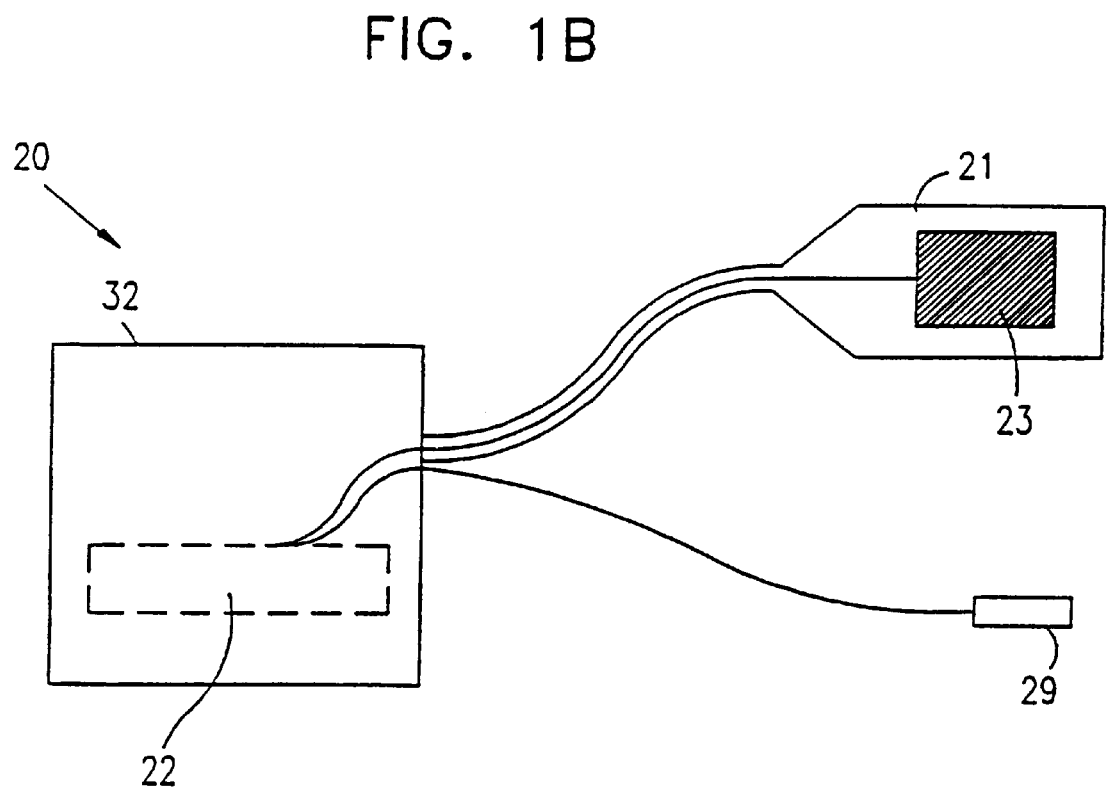
FIG. 1B is a schematic illustration showing a miniaturized implantable device for controlling cardiac output, in accordance with an alternative preferred embodiment of the present invention.

FIG. 1B schematically illustrates device 20 in accordance with an alternative preferred embodiment of the present invention, in which signal generation circuitry 22 is contained in an implantable miniaturized electronic control circuitry case 32, similar to implantable pacemaker cases known in the art. Unlike control unit 27, case 32 does not include display 24 and control panel 26, but in other respects, the embodiment of FIG. 1B is functionally similar to that of FIG. 1A.

In the embodiment shown in FIG. 1B, stimulation electrode 23 is shown to be a relatively large area electrode, designed to provide stimulation an area of at least 5 mm$^2$ in the heart. Electrode 23 preferably comprises a low-resistance carbon material, preferably vitreous carbon, or alternatively, pyrolitic carbon. Electrodes made of such materials are manufactured, for example, by Sorin Biomedica, of Saluggia, Italy, and by Goodfellow Cambridge Ltd., of London, England. Both types of carbon materials are known for their compatibility with heart tissue, in-vivo durability and excellent electrical properties. It will be understood, however, that other types of electrode materials made also be used, such as various types described in *A Guide to Cardiac Pacemakers, Defibrillators and Related Products*, by Morse, et al. (Droege Computing Services, Durham, N.C.), which is incorporated herein by reference. Stimulation probe 21 may comprise more than a single stimulation electrode. Sensing electrode 29 may comprise any suitable type of intracardiac electrode, known in the art.

Preferably, electrodes 23 and 29 are coated with an anticoagulant, such as heparin, preferably in a time-release form, or elute the anticoagulant into the heart tissue, to prevent clot formation on and around the electrodes. Such electrodes may be produced in a manner similar to steroid-eluting electrodes known in the art, for example, the Medtronic CAPSURE model 4003 electrode, described in *The Foundations of Cardiac Pacing*, by Sutton and Bourgeois, p. 73, which is incorporated herein by reference.

Figure 2A:
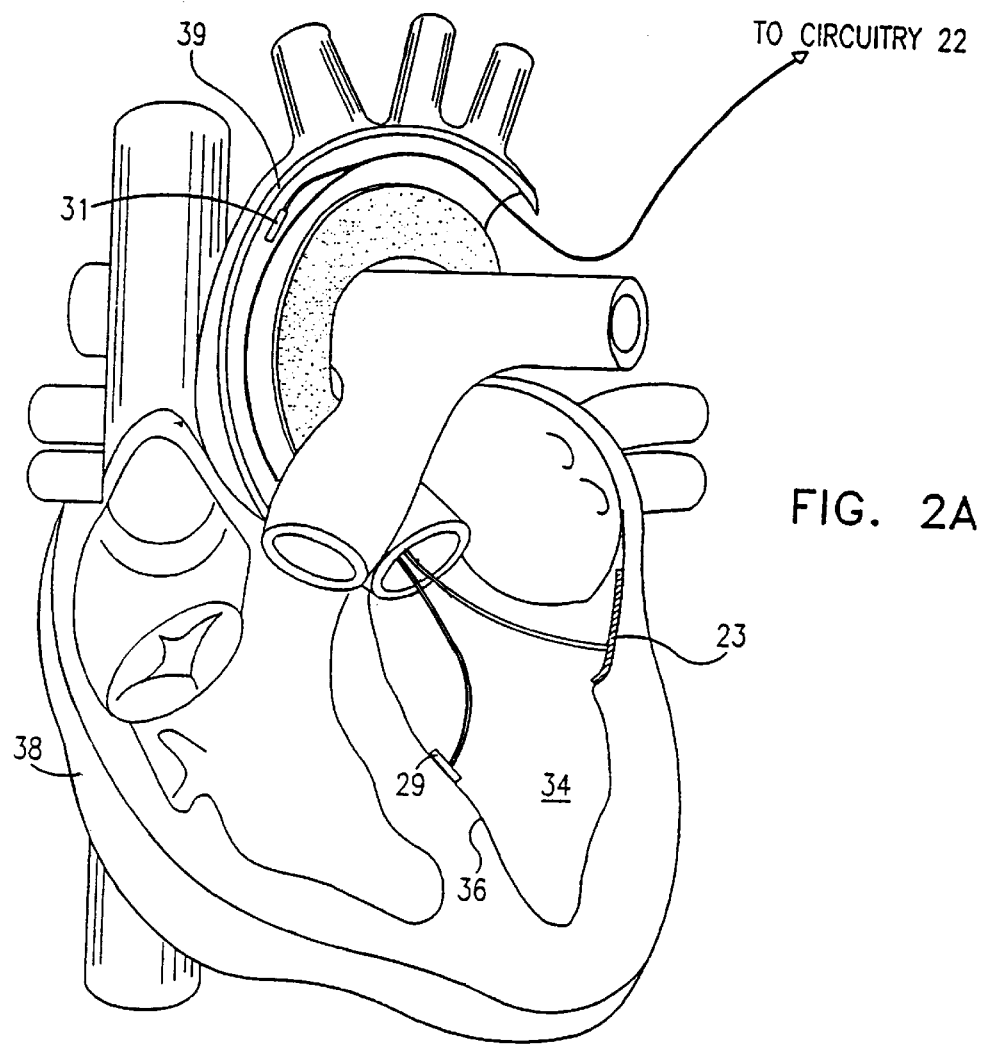
FIG. 2A is a schematic sectional illustration showing the heart of a patient, into which stimulation and sensing electrodes for use in conjunction with the device of FIG. 1A are inserted, in accordance with a preferred embodiment of the present invention.

FIG. 2A is a schematic illustration showing electrodes 23 and 29 implanted in a subject's heart 38, in accordance with a preferred embodiment of the present invention. Electrodes 23 and 29 are implanted in a chamber of the heart, preferably both in left ventricle 34. Most preferably, non-excitatory stimulation electrode 23 is implanted in contact with the wall of left ventricle 34, and sensing electrode 29 is implanted in septum 36, between the ventricles. Electrodes 23 and 29 are connected by wires passing through aorta 39 to either control unit 27 outside the body or to implantable case 32, which is preferably implanted in the patient's chest. When circuitry 22 detects an electrical activation pulse in the electrogram signal received from electrode 29, it generates a stimulation pulse, which is applied to electrode 23, preferably so as to increase the contraction of at least the segment or the wall of ventricle 34 with which electrode 23 is in contact, thus increasing the ventricular stroke volume.

Alternatively, stimulation electrode 29 and, optionally, sensing electrode 23 may be implanted surgically, preferably in the epicardium.

Figure 2B:
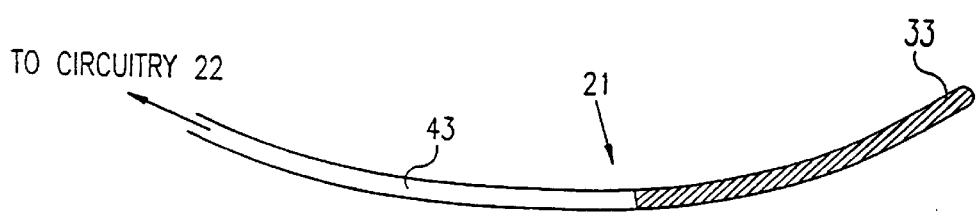
FIG. 2B is a schematic illustration of a non-excitatory stimulation probe, in accordance with another preferred embodiment of the present invention.

FIG. 2B is a schematic illustration showing an alternative preferred embodiment of the present invention, in which non-excitatory stimulation probe 21 comprises a wire electrode 33. The electrode, which preferably comprises carbon material, as described above, is connected by an insulated conductor 43 to circuitry 22. It is preferably implanted in one of the blood vessels of the heart. Most preferably, electrode 33 is passed through the right atrium of the heart, into the coronary sinus, using techniques of catheterization known in the art, and is positioned therein adjacent to left ventricle 34. The electrode is then driven by circuitry 22 to deliver the non-excitatory stimulation pulses to the heart wall, as described herein.

Figure 3:
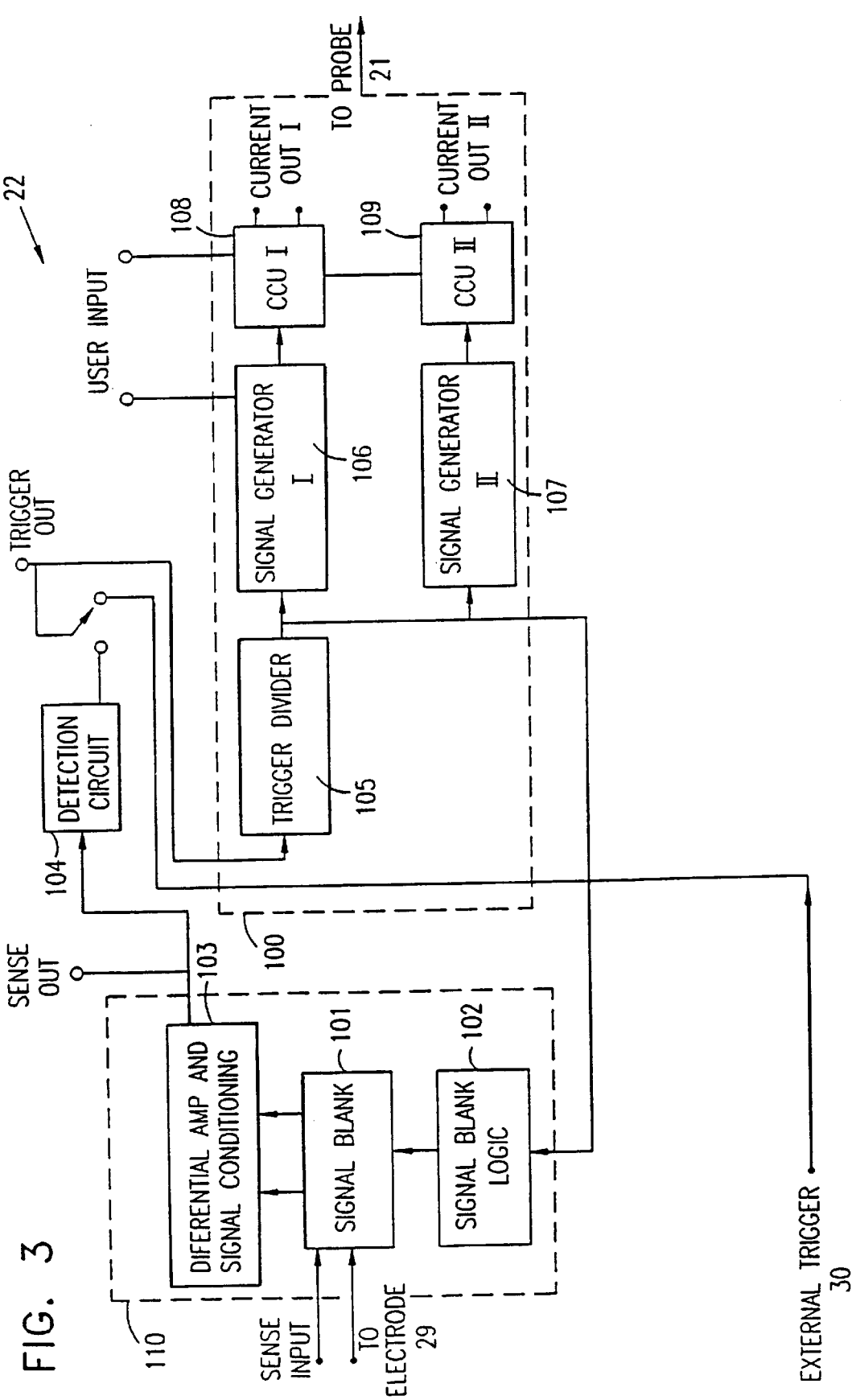
FIG. 3 is a schematic block diagram of control circuitry use in the devices depicted in FIG. 1A, in accordance with a preferred embodiment of the present invention.

FIG. 3 is a schematic block diagram of signal generation circuitry 22, in accordance with a preferred embodiment of the present invention. Circuitry 22 comprises a stimulation section 100, a detection circuit 104 and a sensing, unit 110. Unit 110 receives and conditions electrogram signals from sensing electrode 29. Detection circuit 104 senses a local activation wave in the electrogram, preferably by detecting a slope and voltage level corresponding to the rising edge of the wave, as is known in the art, and generates a trigger pulse responsive thereto. The trigger pulse is conveyed to stimulation section 100, which generates the stimulation pulses and applies these pulses to the electrodes of stimulation probe 21.

Sensing, unit 110 includes signal blanking unit 101 and signal blank logic 102 and a differential amplifier and signal conditioning circuit 103. The blanking operates to block the input to detection circuit 104 while the output of stimulation section 100 is active, to prevent ago the system from generating trigger pulses due to stimulation artifacts.

Stimulation section 100 comprises a trigger divider 105, which generates a modified trigger pulse in response to input trigger pulses from detection circuit 104 or alternatively from external trigger input 30. The trigger divider allows a user of device 20 to select whether the stimulation pulse will be applied at every heart beat or only once in a predetermined number of beats. Section 100 further includes signal generators 106 and 107, which generate voltage signals of predefined characteristics, as described below, in response to the modified trigger pulse, and constant current units (CCU) 108 and 109, which convert input voltage signals from the signal generators to output current pulses. Two stimulation output channels are shown in FIG. 3, enabling different stimulation pulses to be applied to two or more different stimulation electrodes. It will be appreciated, however, that only one of the channels need be used or alternatively, that additional channels may be added to drive additional stimulation electrodes.

Figure 4:
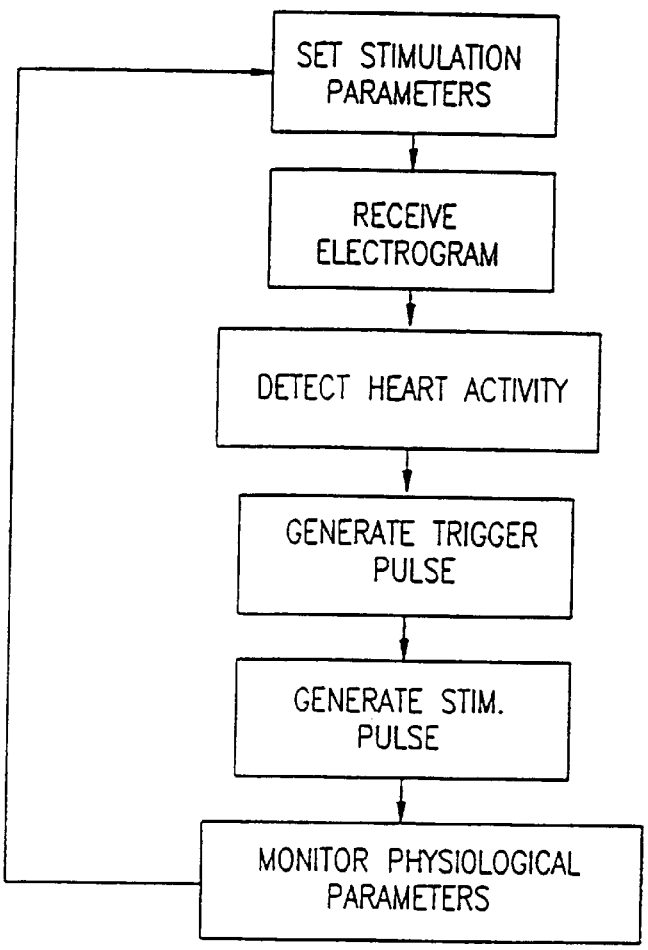
FIG. 4 is a flow chart illustrating a method of regulating cardiac output, in accordance with a preferred embodiment of the present invention.

FIG. 4 is a flow chart, which summarizes a method for regulation of cardiac output using device 20, according to a preferred embodiment of the present invention. Preferably, parameters of the stimulation pulse, such as its level, duration, delay and waveform characteristics, as described below, are preset by the user. Sensing electrode 29 senses electrogram signals, as described above, and signal generation circuitry 22 receives these signals and inputs them to detection circuit 104, which detects heart activity, preferably the sinus rhythm, and generates a trigger pulse responsive thereto. The trigger pulse drives stimulation section 100 to generate the stimulation pulse, which is applied to the heart by stimulation electrode 23. In an alternative preferred embodiment, an external trigger coupled to input 30 is employed.

Optionally, physiological parameters related to the cardiac output are monitored in order to verify the efficacy of the non-excitatory stimulation. For example, flow of blood through aorta 39 may be detected by flow sensor 31, as illustrated in FIG. 2A. Preferably, at least some of the parameters of the stimulation pulse, for example, its amplitude and/or timing, are adjusted responsive to the monitored parameters so as to achieve a desired cardiac output level. Such monitoring and adjustment are preferably carried out on-line, for example, by control unit 27 itself. Alternatively or additionally, a separate telemetry unit (not shown in the figures) monitors the parameters and is used to program control unit 27 to vary the parameters of the stimulation pulse accordingly.

Figure 5:
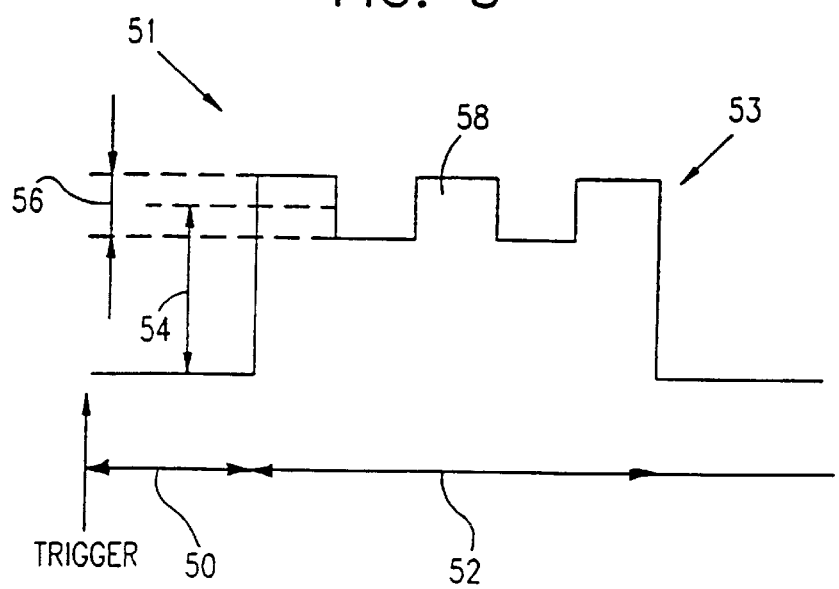
FIG. 5 is a schematic illustration showing a square wave stimulation pulse applied by stimulation electrodes to the patient's heart, in accordance with a preferred embodiment of the present invention.

FIG. 5 is a schematic illustration of a non-excitatory stimulation pulse 51 applied by stimulation electrode 23 to cardiac tissue, in accordance with a preferred embodiment of the present invention. In some preferred embodiments of the present invention the regulation of cardiac output is achieved by varying certain characteristics of pulse 51. Non-excitatory stimulation energy is applied to stimulation electrode 23 in the form of a baseline pulse 53 having a baseline amplitude, indicated by an arrow 54 in FIG. 5, of preferably 5 to 10 mA, optionally up to 50 mA. The duration of pulse 51, indicated by an arrow 52, preferably ranges between 30 and 80 ms, and optionally up to 500 ms. Pulse 53 is preferably followed by another pulse of opposite polarity (not shown in the figure) to prevent problems of tissue polarization and electrode degradation, as described in the above-referenced '012 PCT application and mentioned above. Preferably, a waveform 58 having a frequency of up to 10 kHz and amplitude, indicated by an arrow 56, up to or comparable to the baseline amplitude is superimposed on the baseline amplitude of pulse 53. Although waveform 58 is shown here as a square wave, any other suitable waveform may be used, for example, a sinusoid or sawtooth wave.

Preferably, waveform 51 is triggered upon the detection of the rising edge of the R-wave of the heart's electrical activity by detection circuit 104. Alternatively, signal generators 106 and 107 may be controlled to provide a delay, indicated by an arrow 50 in FIG. 5, of between 1 and 500 msec between the trigger input and the pulse generation. The appropriate delay may depend on whether the trigger is provided by detection circuit 104 or by external trigger 30, as well as on the relative positions of sensing electrode 29 and sensing electrode 23. The delay is adjusted based on the desired increase or decrease of cardiac output that is to be achieved, and the optimal delay will generally vary from patient to patient.

Figure 6:
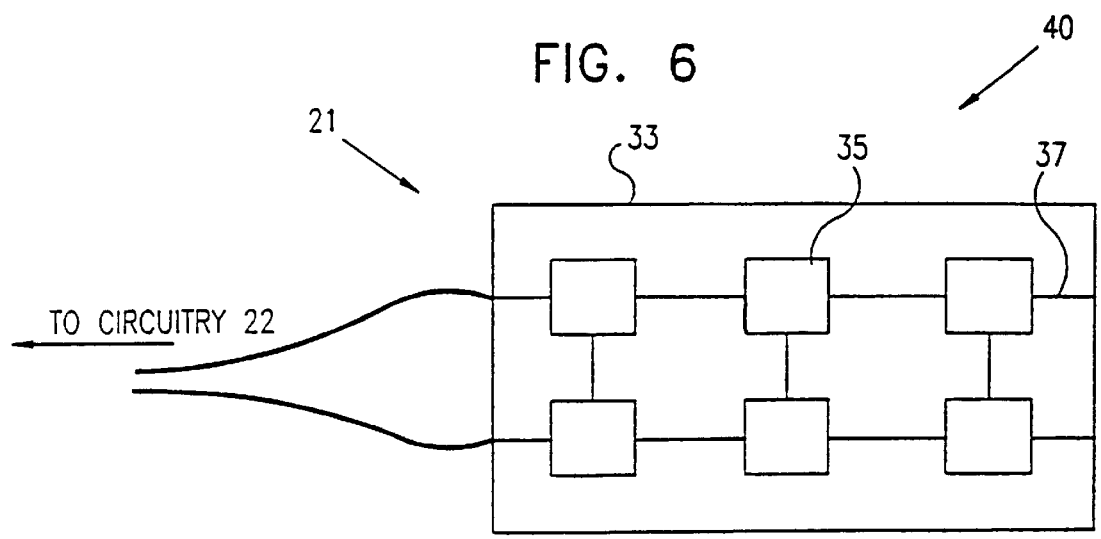
FIG. 6 is a schematic illustration of a stimulation electrode for use in conjunction with the devices of FIGS. 1A and 1B, in accordance with a preferred embodiment of the present invention.

FIG. 6 is a schematic illustration showing an electrode net 40, for use as part of stimulation probe 21, in accordance with a preferred embodiment of the present invention. Net 40 comprises a plurality of stimulation electrodes 35, preferably, interconnected by a conductor network 37. Electrodes 35 are preferably individually and/or collectively addressable, and may operate in either a unipolar or a bipolar mode. Net 40 is preferably large enough to cover a substantial segment of the heart wall, preferably at least 1 $cm^2$ and most preferably at least 4 $cm^2$. Each individual electrode 35 preferably has an area of at least 5 $mm^2$, and is separated from its neighbors preferably by at least 1 cm.

In this preferred embodiment, cardiac output regulation is preferably achieved through variation of the stimulated area of a segment of the heart wall with which net 40 is in contact, as described in the '012 PCT patent application. Preferably, the stimulated area is varied by changing the active area of net 40, i.e., varying the extent of the area of the net over which electrodes 35 are driven to deliver electric stimulation to the heart. The inventors have found, for example, that when the non-excitatory stimulation is applied between pairs of electrodes, selected among a plurality of electrodes placed in the left ventricle, the resultant enhancement of left-ventricular pressure and cardiac output varies responsive to the relative positions of the electrodes in the pair and the distance between them. Electrodes 35 in net 40 may thus be selectably addressed to optimize the hemodynamic results of the stimulation. Moreover, electrodes 50 may also be used as sensing electrodes, to map cardiac electrical activity over the segment of the heart wall, so that the stimulation may be applied responsive to the map.

Figure 7:
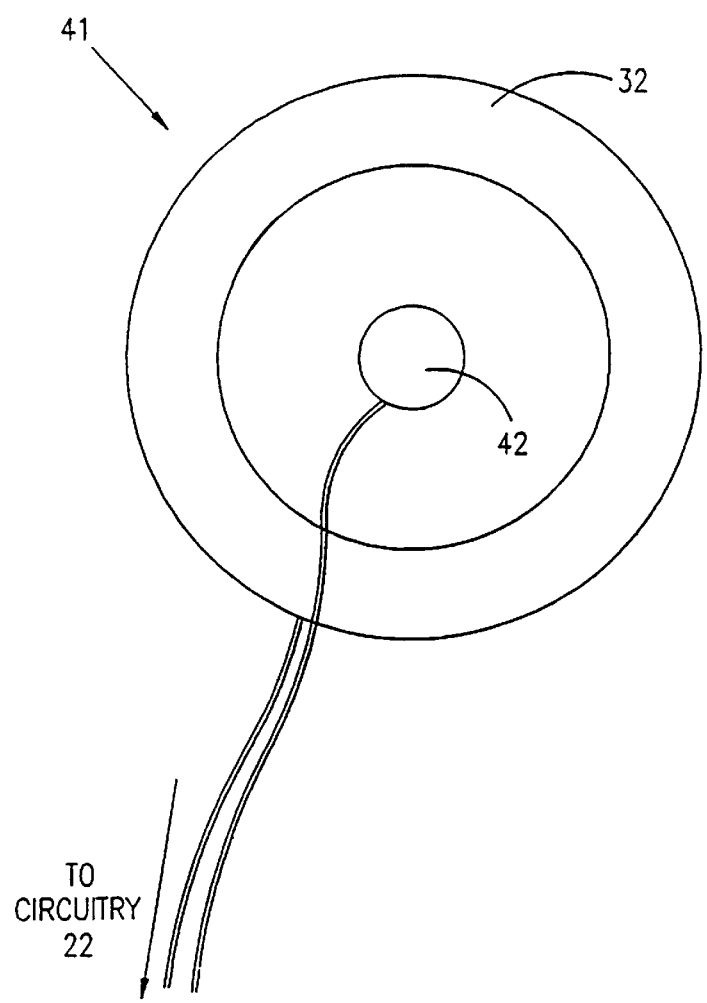
FIG. 7 is a schematic illustration of a hybrid electrode for use in conjunction with the devices of FIGS. 1A and 1B, in accordance with an alternative preferred embodiment of the present invention.

FIG. 7 schematically illustrates a hybrid electrode probe 41 for use with device 20, in accordance with an alternative preferred embodiment of the present invention. Probe 41 comprises an annular stimulation electrode 32, preferably a carbon electrode, as described above, surrounding a smaller sensing electrode 42 at the center of the probe, preferably, a platinum or platinum/iridium electrode, most preferably bipolar. It will be understood that the methods, stimulation waveforms and control electronics described above in relation to electrode 23 may be applied using probe 41, as well as any other suitable electrode configuration. Probe 41 is advantageous in that it reduces the number of separate electrodes that need to be introduced into and implanted in the heart.

Figure 8A:
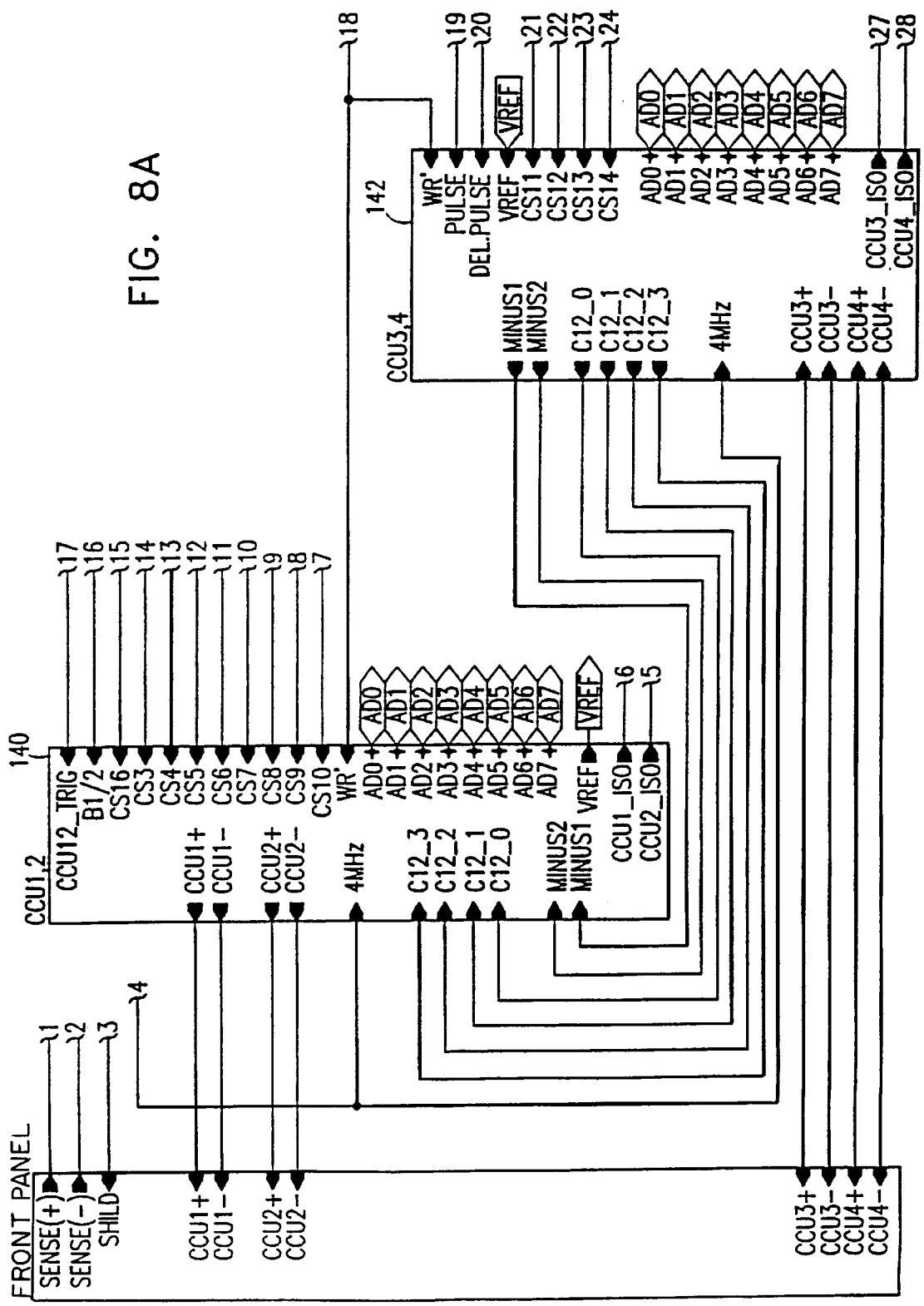
FIGS. 8–32 are electronic schematic electronic diagrams showing circuitry for use in the device of FIG. 1A, in accordance with a preferred embodiment of the present invention.
Figure 8B:
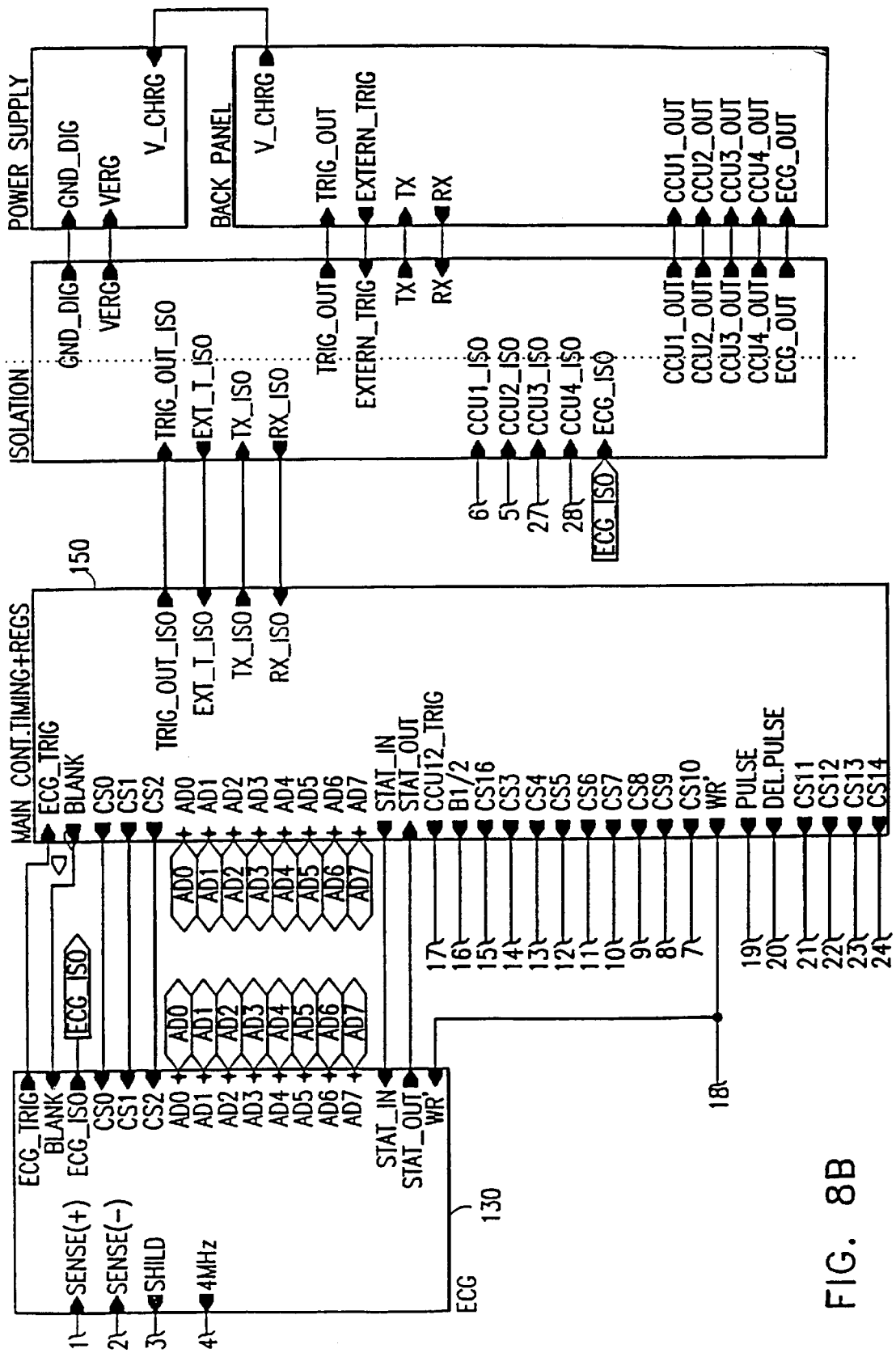

FIGS. 8–31 are electronic schematic diagrams illustrating circuitry for use in implementing the functions of circuitry 22, in accordance with a preferred embodiment of the present invention. As shown in FIGS. 8A and 8B, the circuitry includes an ECG processor 130, a first CCU section 140, and main control circuit 150, which together perform the functions of circuitry 22, as shown in FIG. 3 and described with reference thereto. In addition, a second CCU section 142 is designed to provide, optionally, excitatory stimulation pulses, i.e., to pace the heart. This element is beyond the scope of the present invention, however, and is described in detail in the above-mentioned PCT patent application entitled "Cardiac Output Enhanced Pacemaker," filed on even date and incorporated herein by reference.

FIGS. 9 through 31 are circuit diagrams showing details of the implementation of the elements of FIGS. 8A and 8B.

These diagrams are considered sufficient in and of themselves to enable one skilled in the art to practice the present invention. Various aspects of these diagrams are described hereinbelow.

Figure 9A:
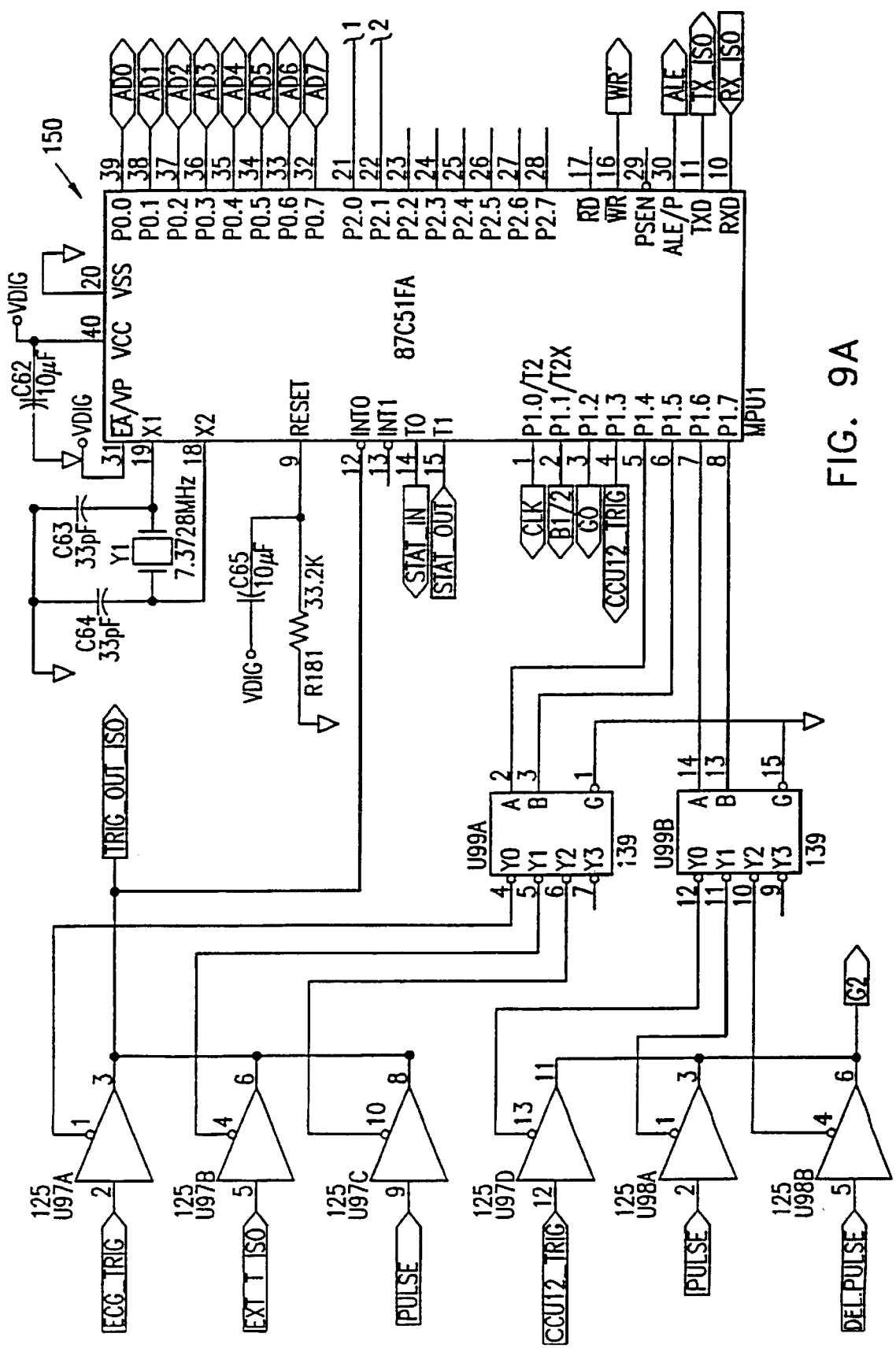
Figure 9B:
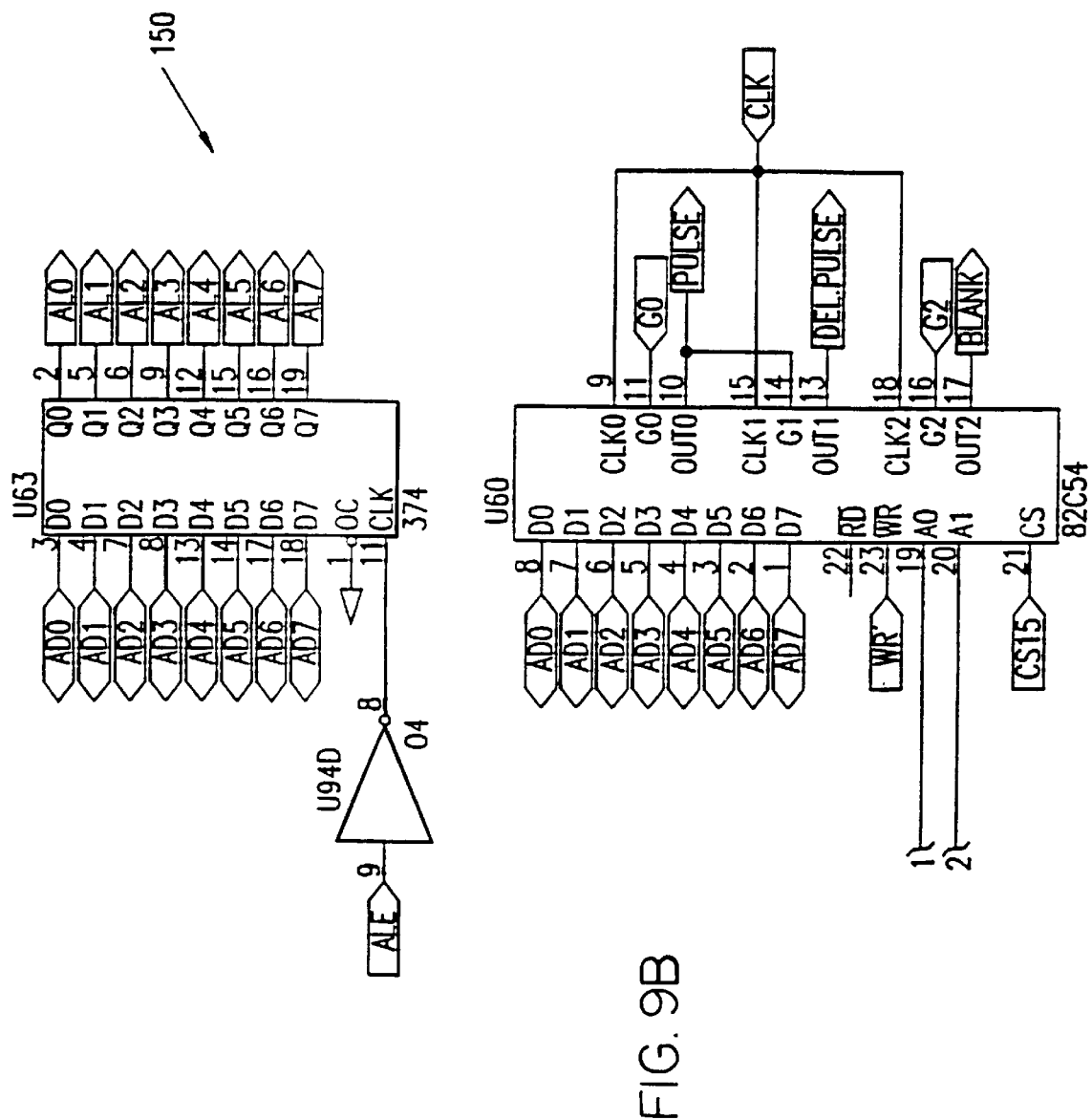
Figure 9C:
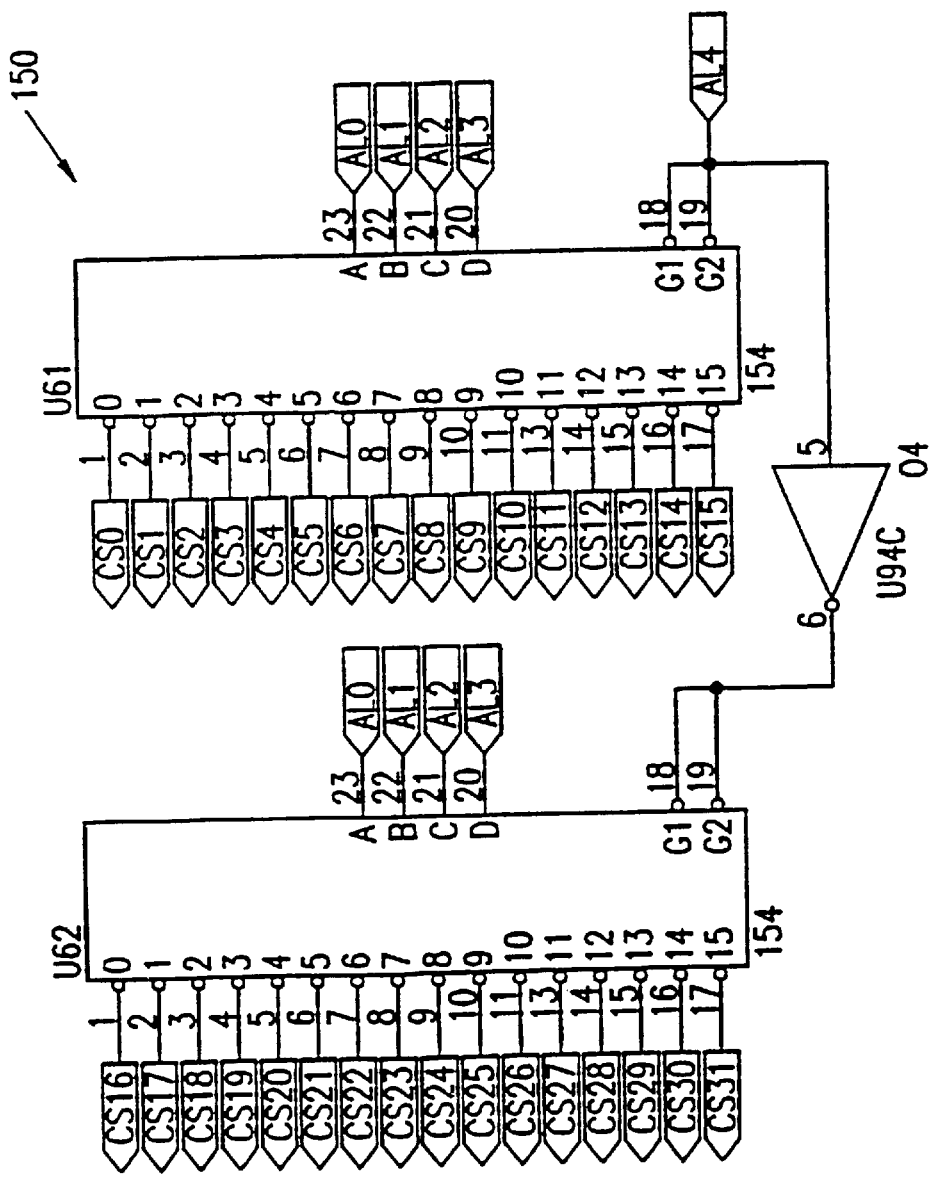

FIGS. 9A, 9B and 9C illustrate main control circuit 150, which is based on a microcontroller MPU 1, preferably an 8051-type microcontroller, as is known in the art. The microcontroller receives user commands via a communications interface, for example, to program parameters of the stimulation pulses to be applied. It controls other elements of circuitry 22 via a data bus, marked AD0–AD7.

Figure 10A:
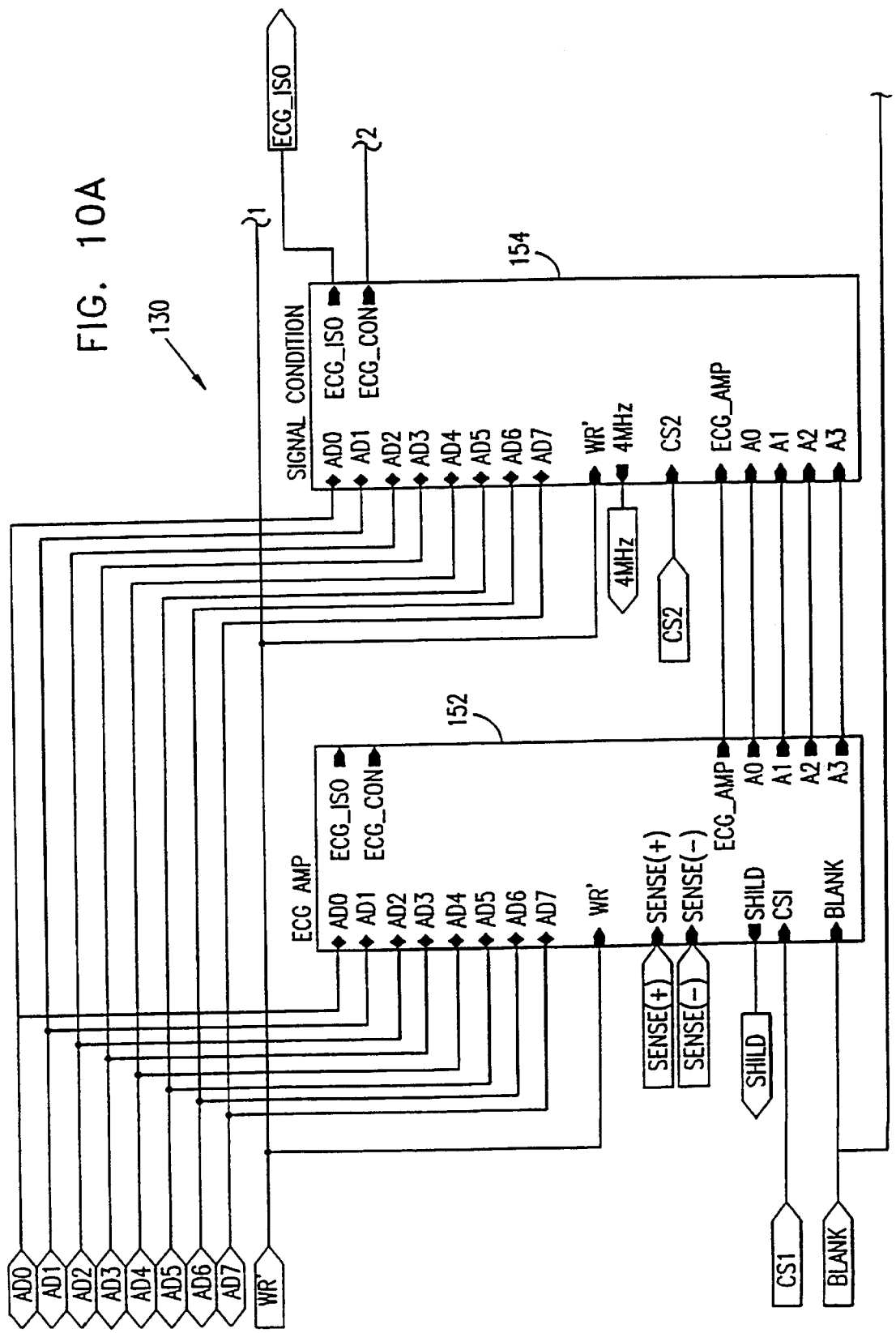
Figure 10B:
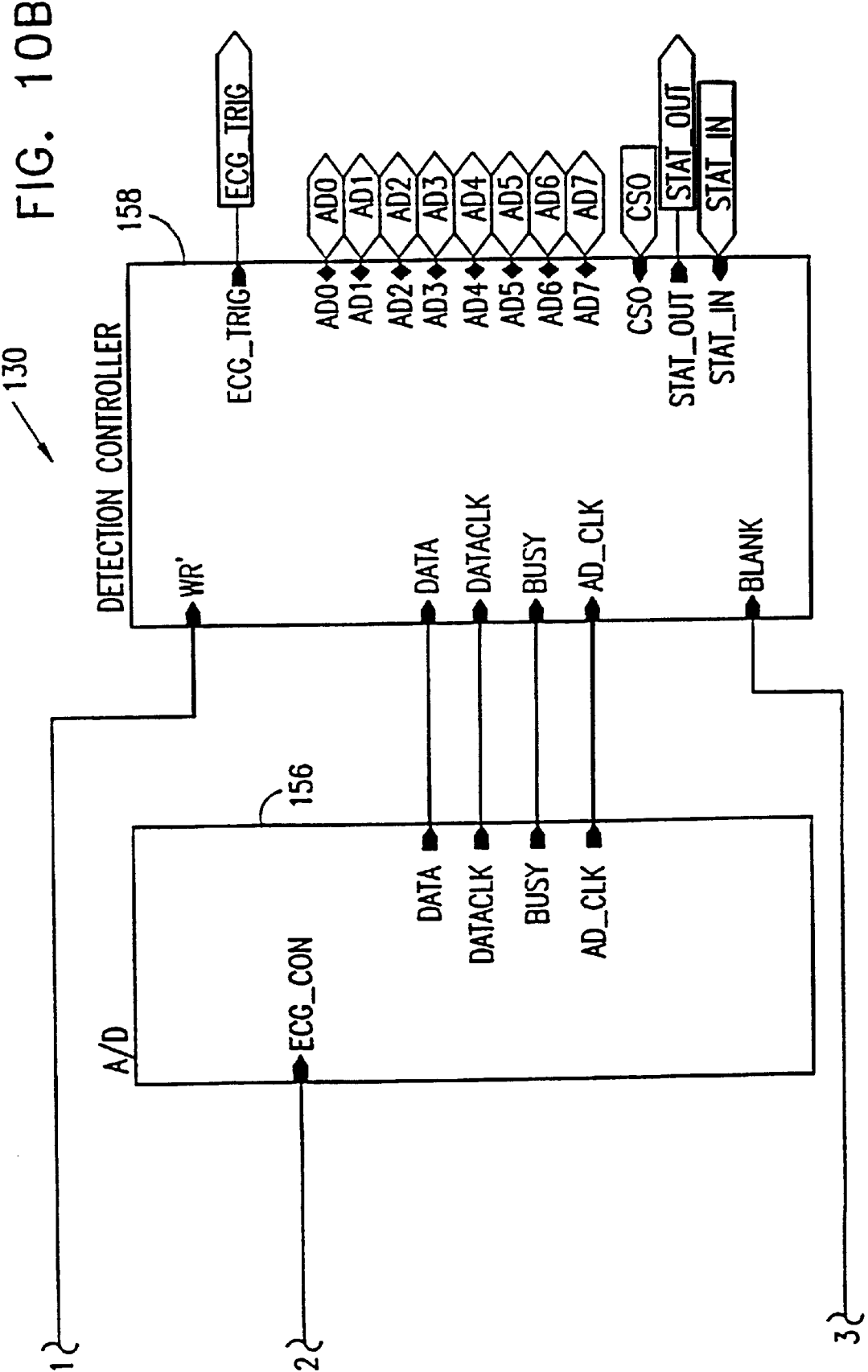
Figure 11:
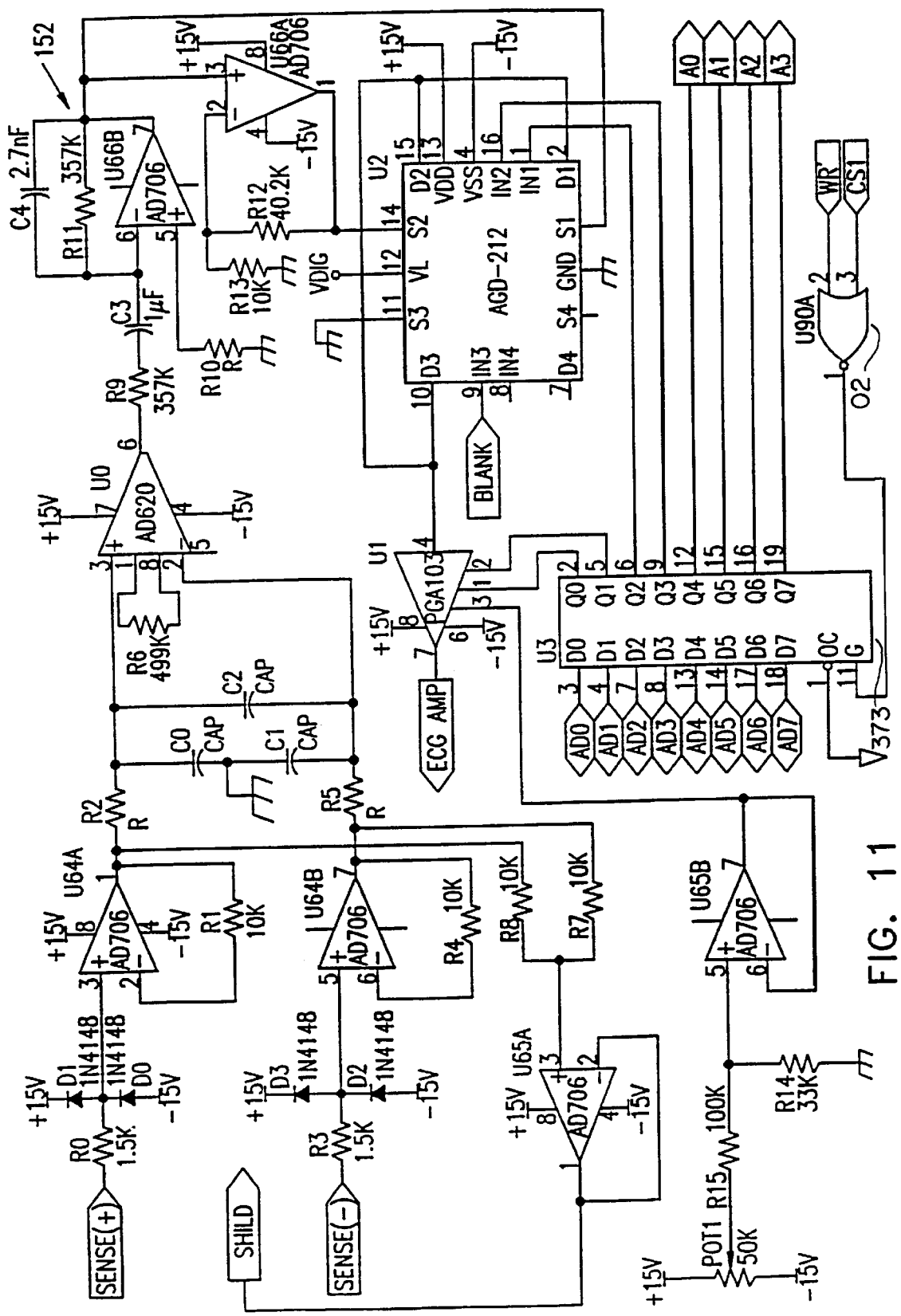
Figure 12A:
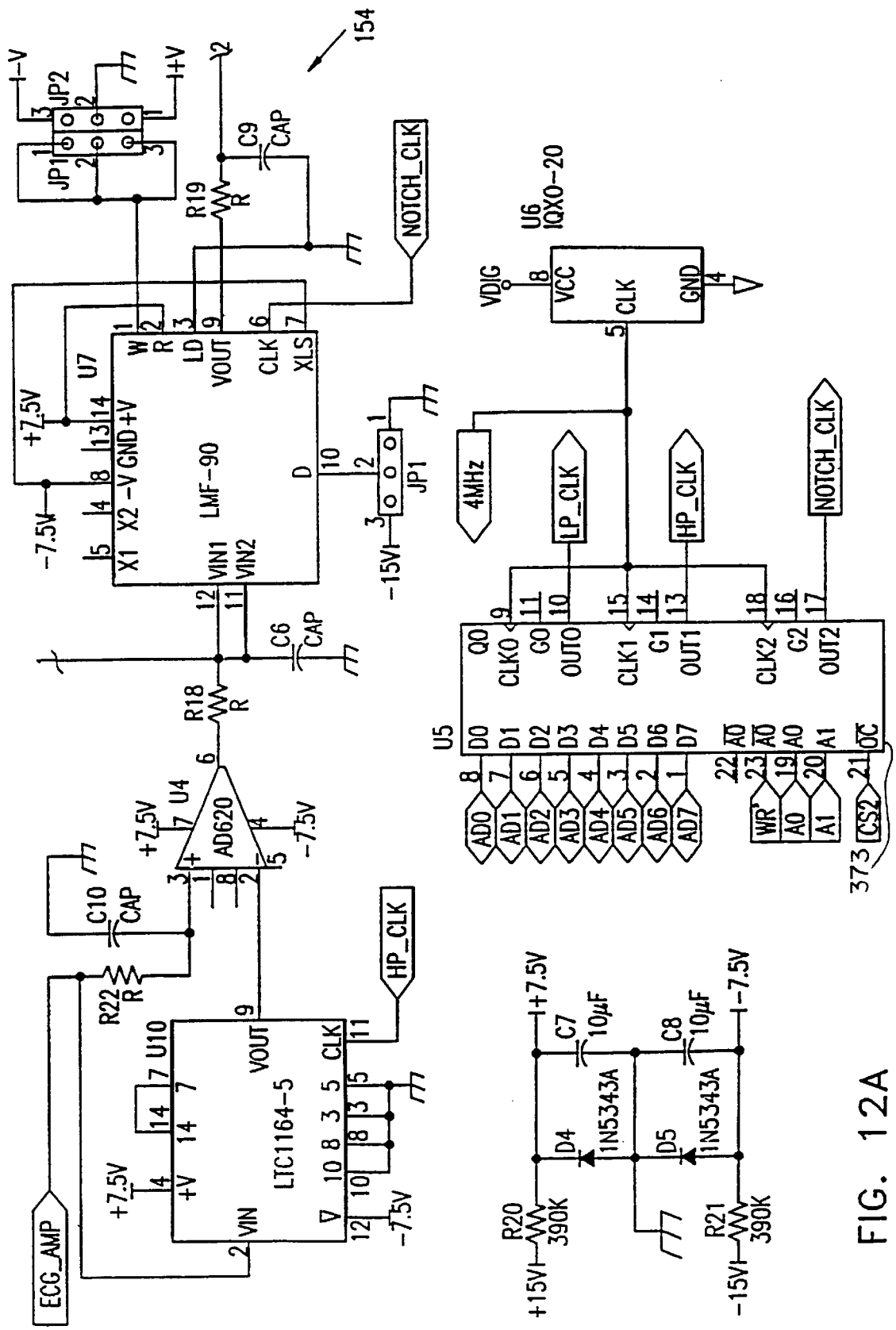
Figure 12B:
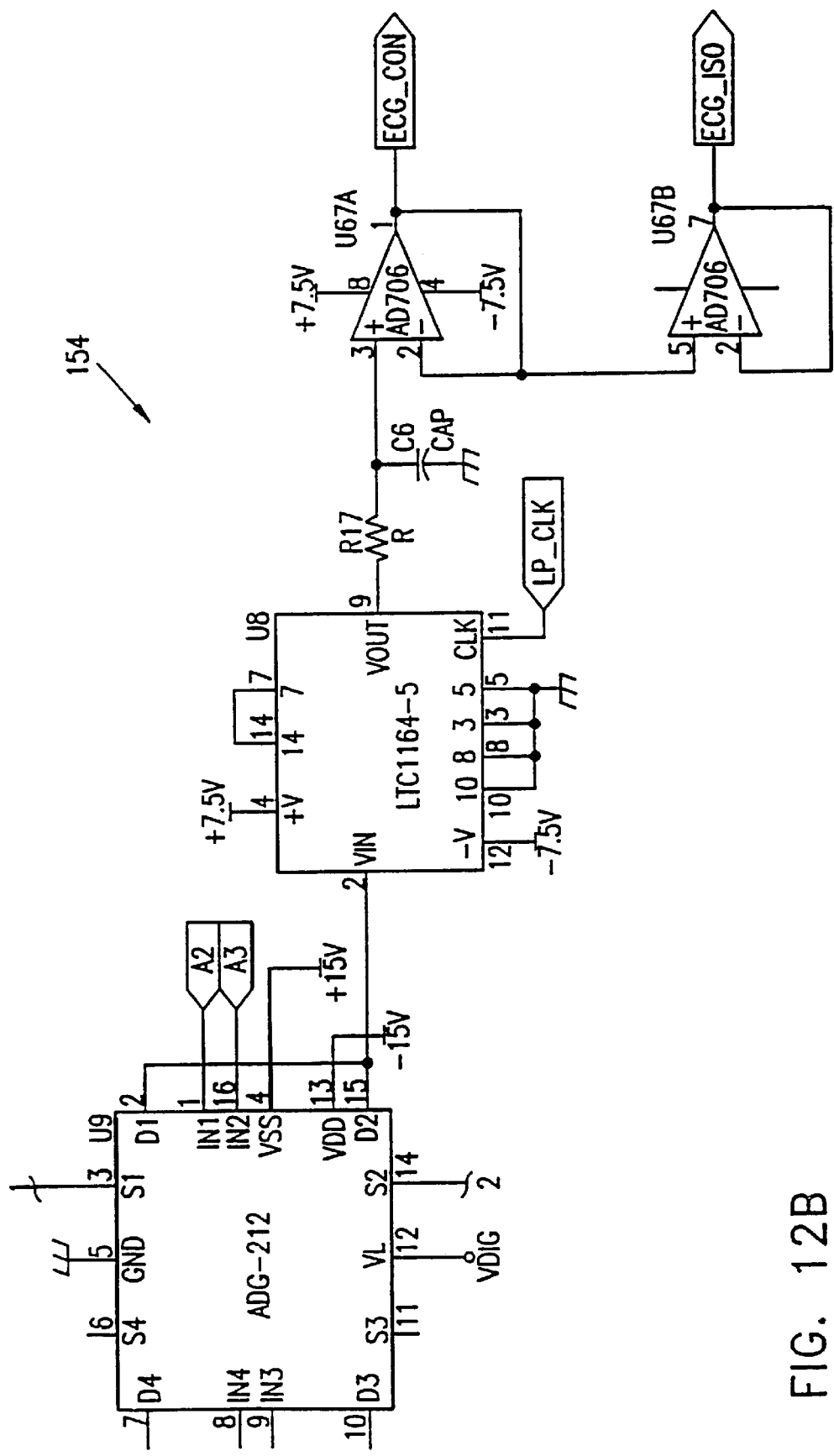
Figure 13:
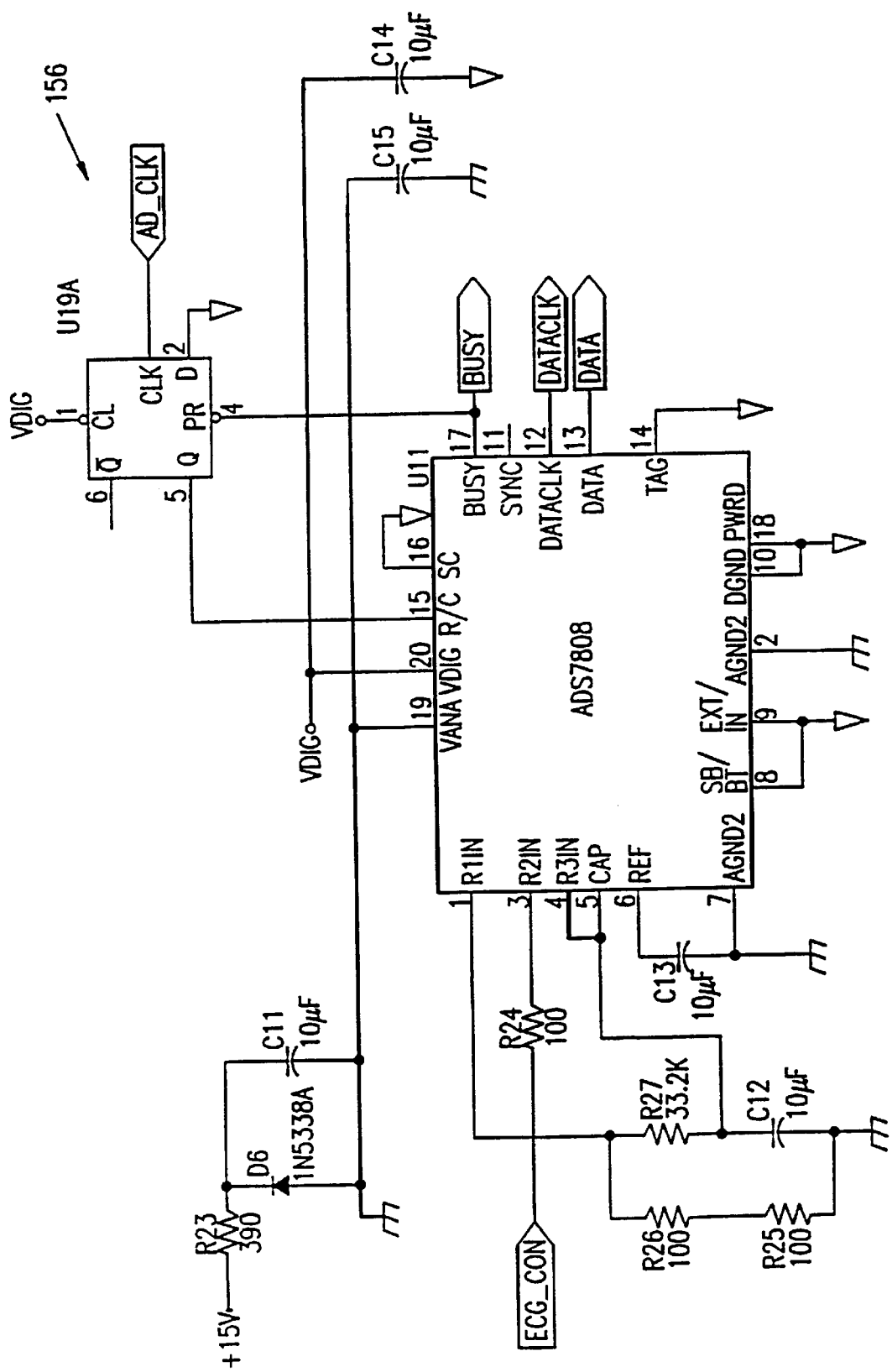
Figure 14A:
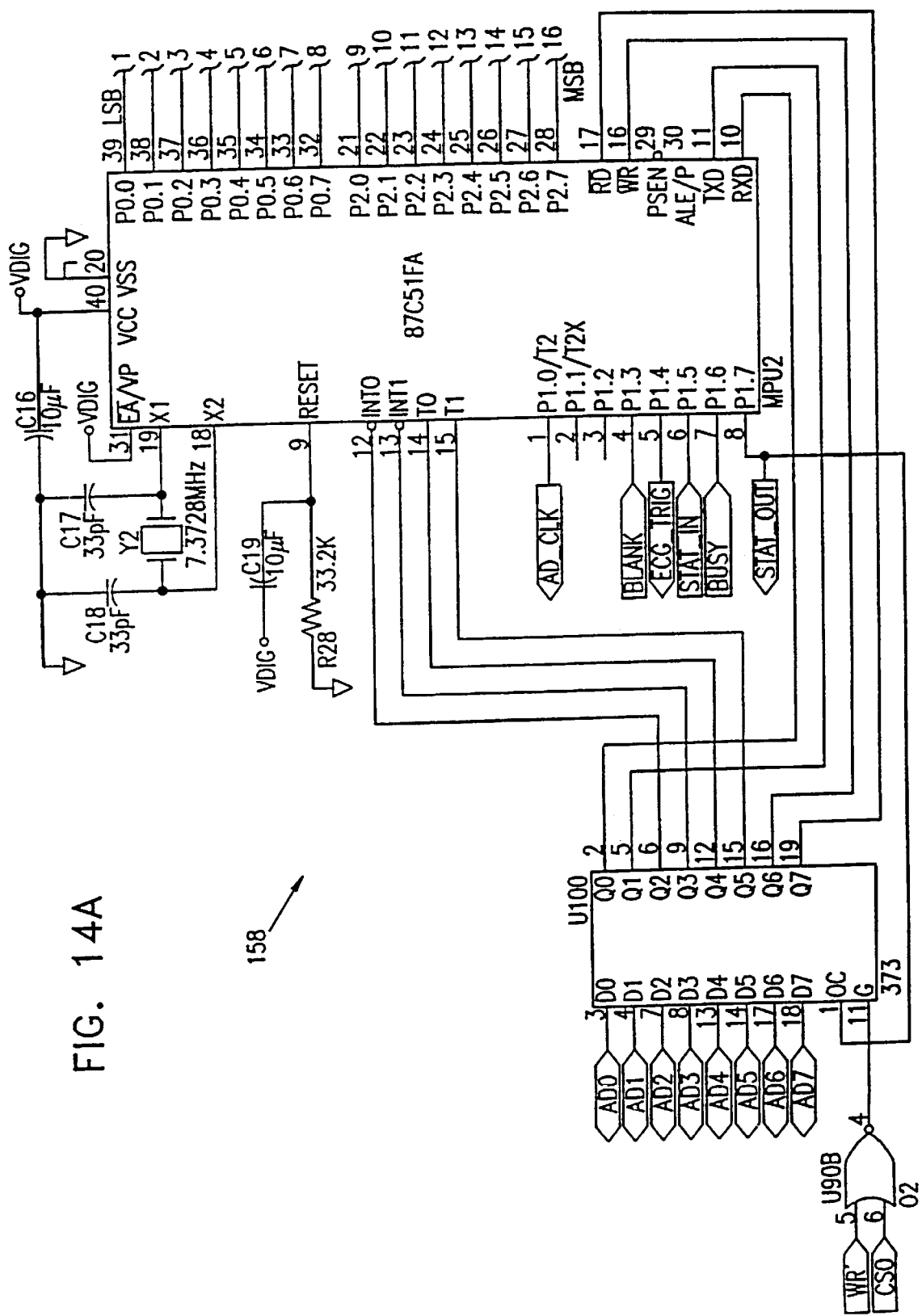
Figure 14B:
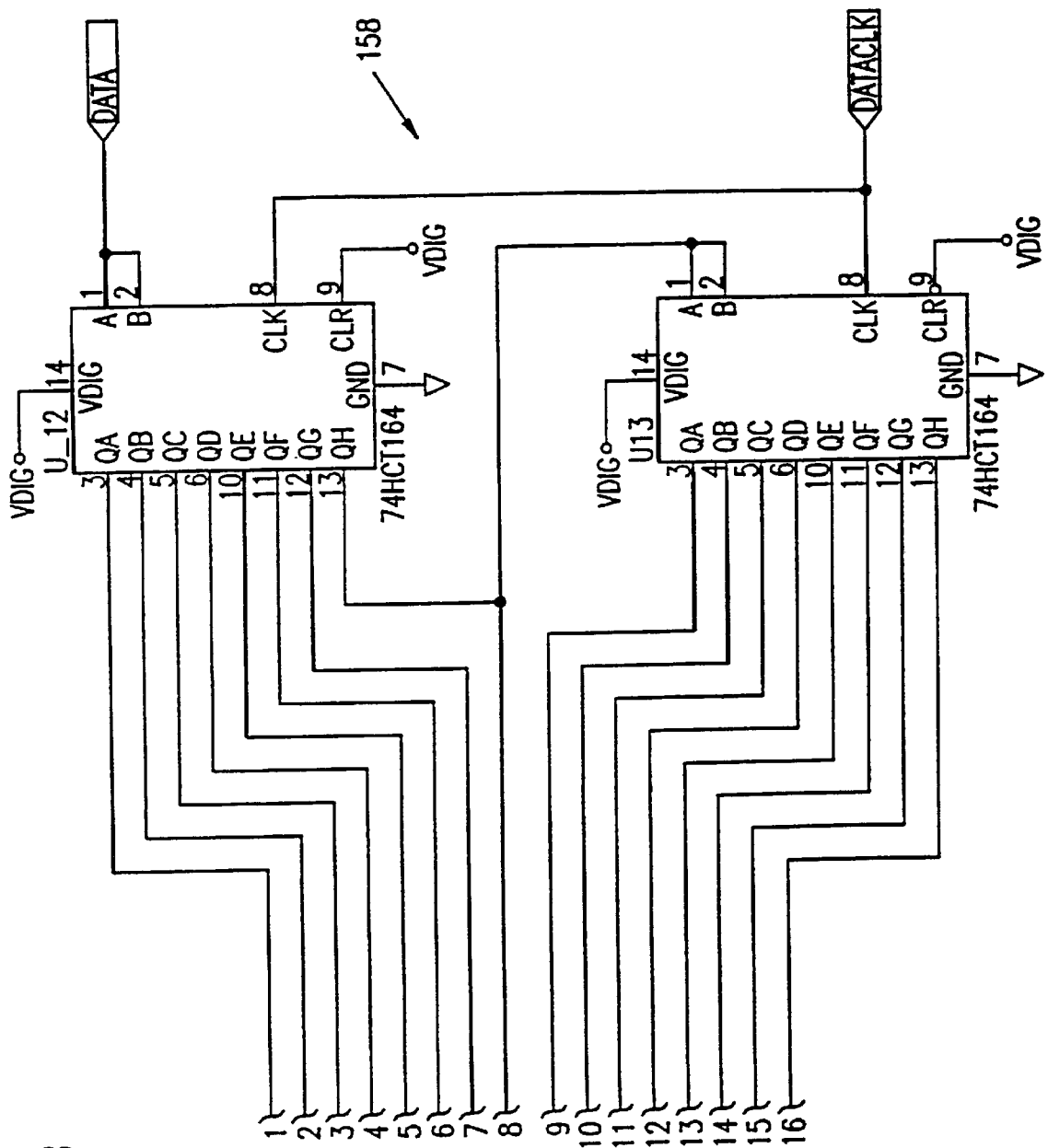

FIGS. 10A and 10B show details of ECG processor 130, which receives electrical signals from the patient's body and processes them to generate trigger pulses, as described above, for driving the non-excitatory stimulation. ECG processor 130 includes an ECG amplifier 152, an ECG signal conditioning unit 154, an A/D converter 156, and a detection controller 158. ECG amplifier 152 is shown in detail in FIG. 11, and comprises a differential preamplifier and programmable gain amplifier and blanking unit. Signal conditioning unit 154, shown in FIGS. 12A and 12B, includes programmable high-pass, low-pass and notch filters, selectable by means of a clock generator, and also including an analog switch for bypassing the notch filter. A/D converter 156 is shown in FIG. 13. FIGS. 14A and 14B illustrate controller 158, including another 8051-type microcontroller MPU2, which analyzes the ECG signal and generates the trigger pulse.

Figure 15A:
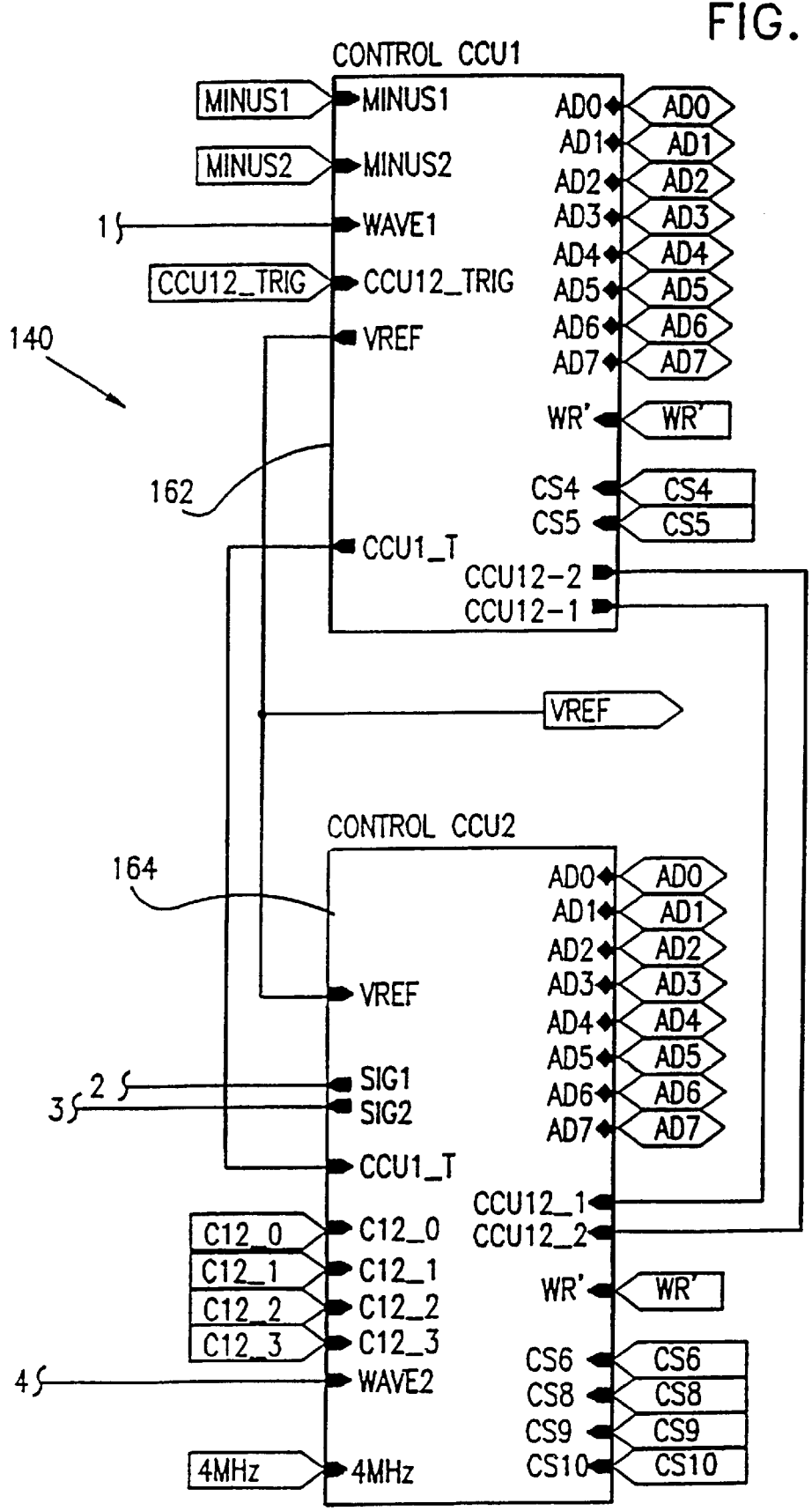
Figure 15B:
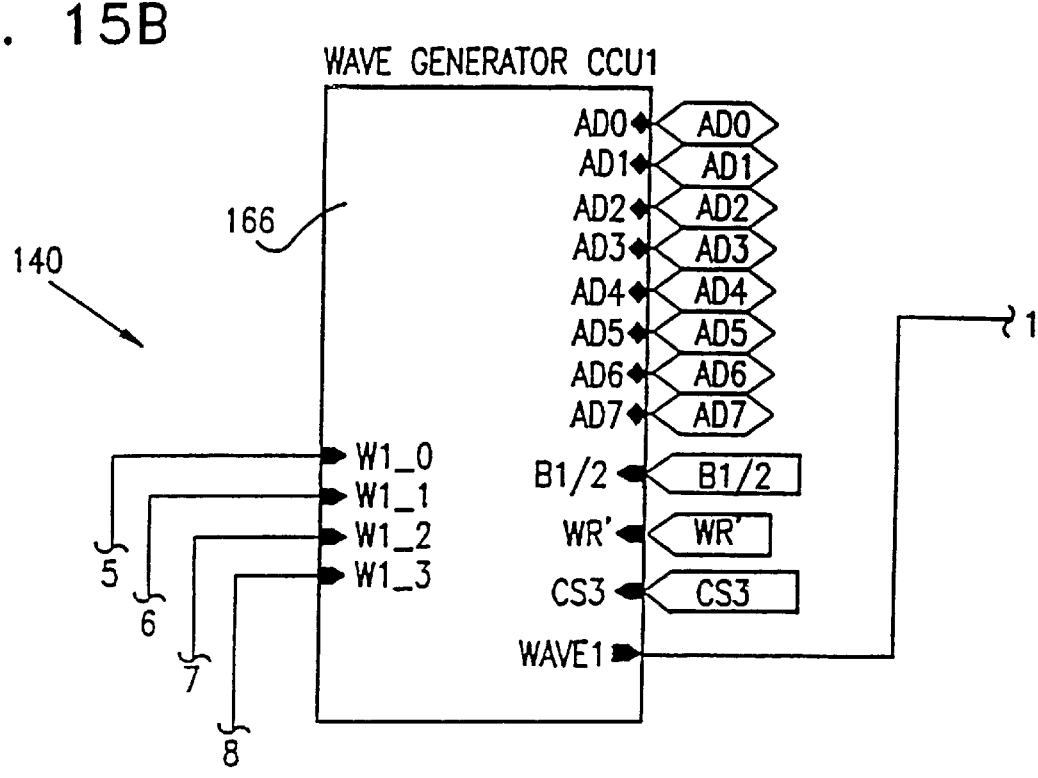
Figure 15B:
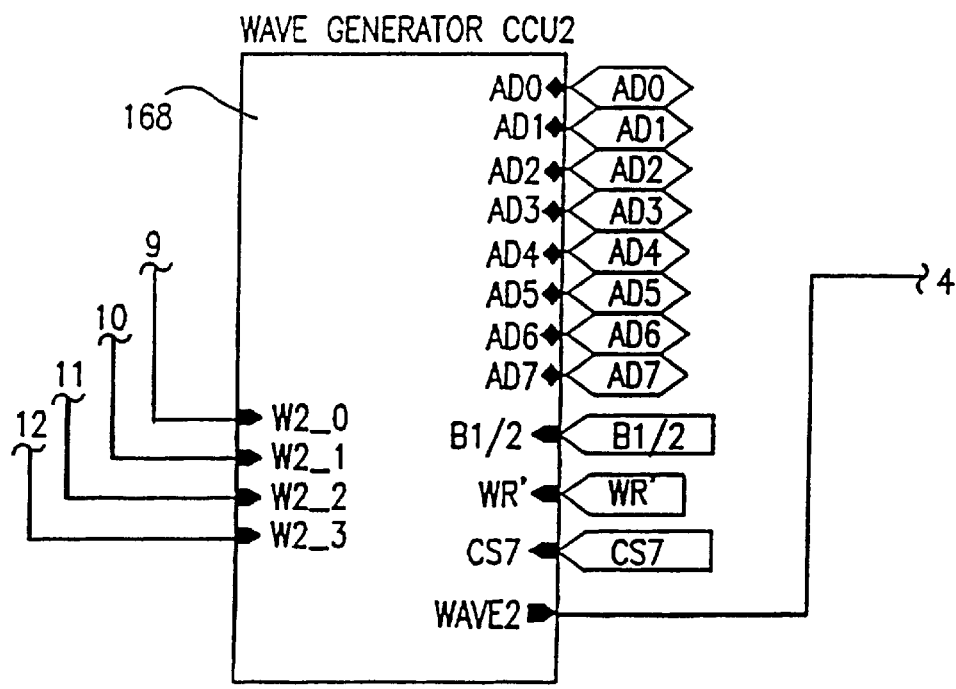
Figure 15C:
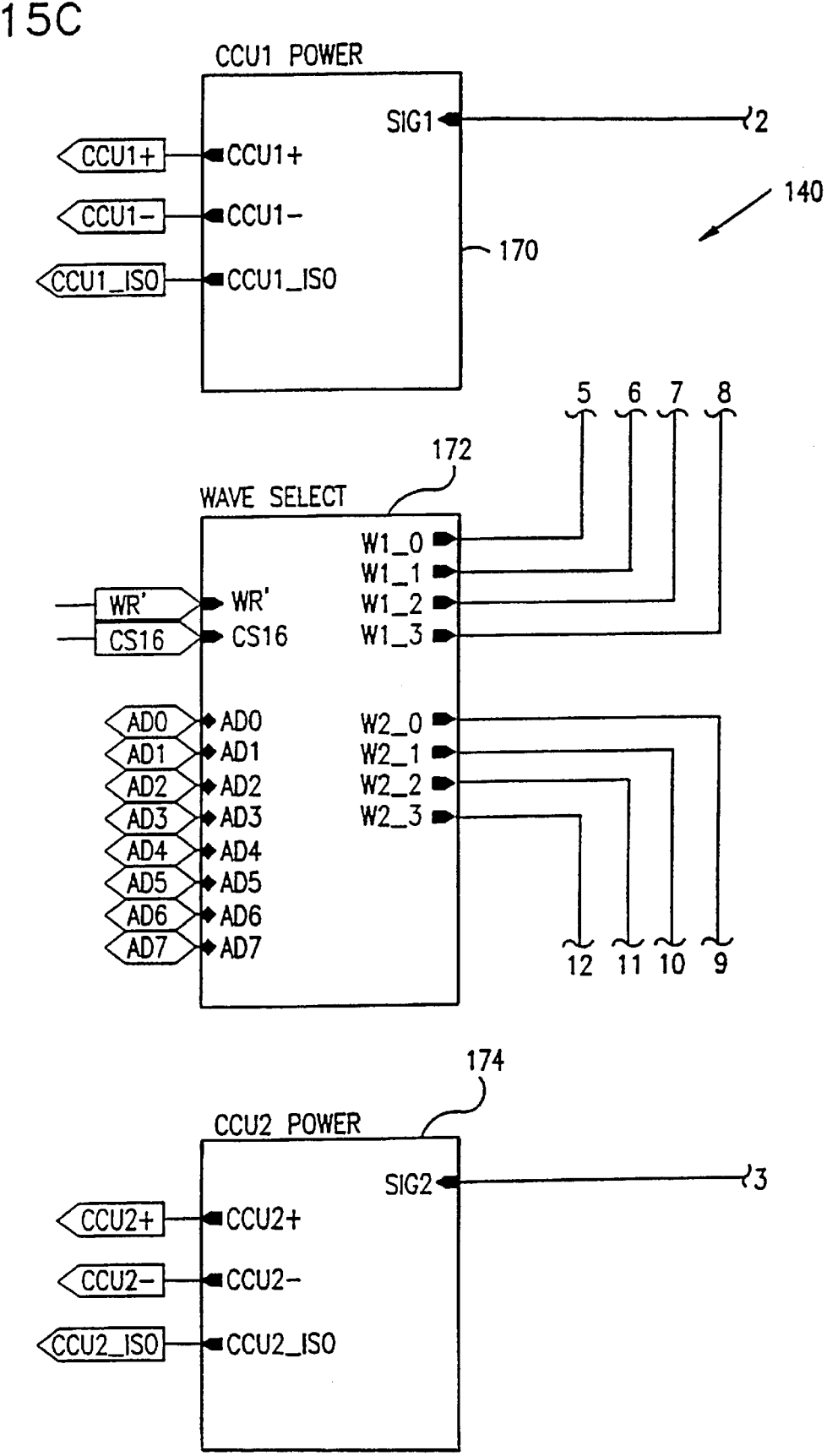
Figure 16A:
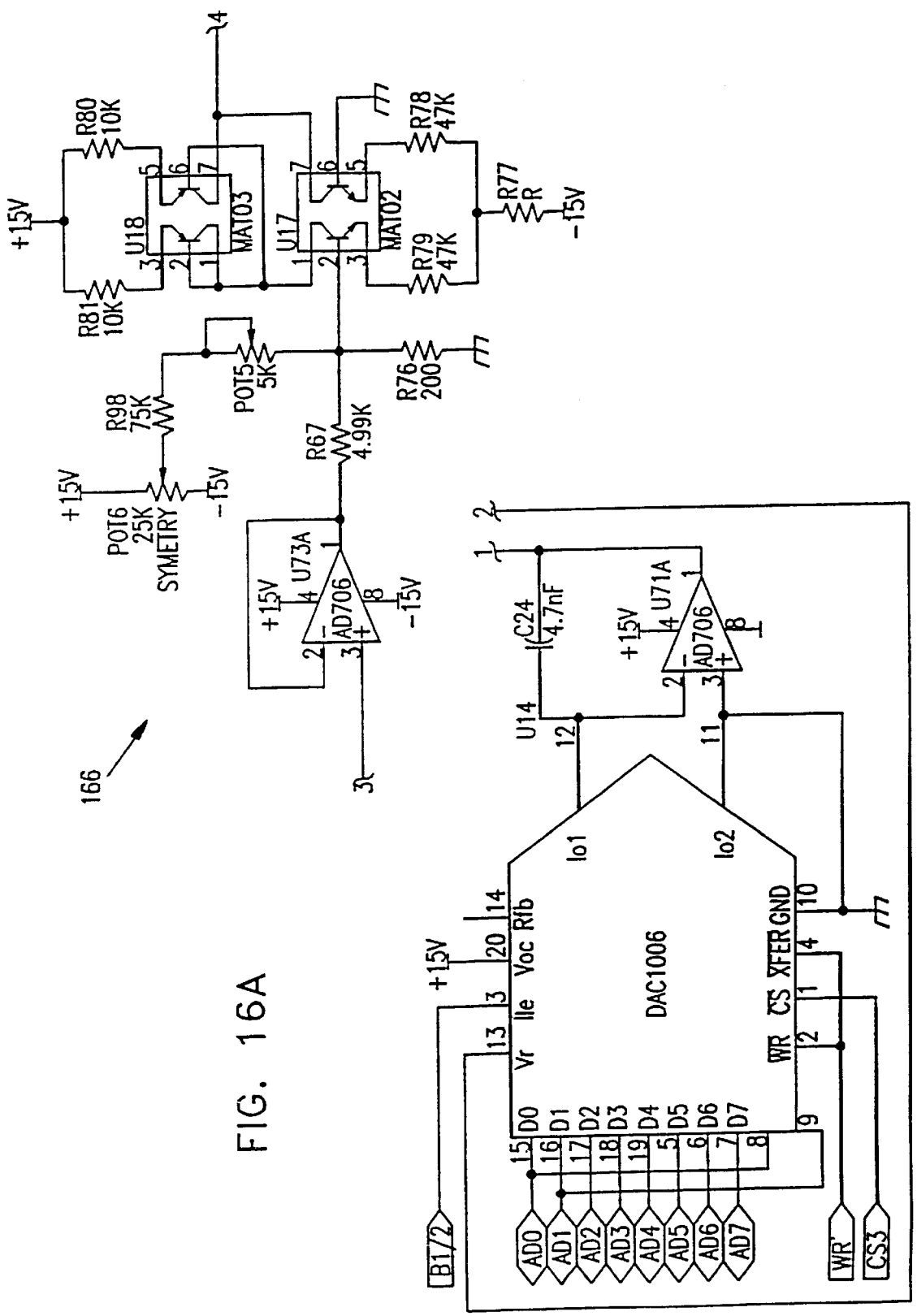
Figure 16B:
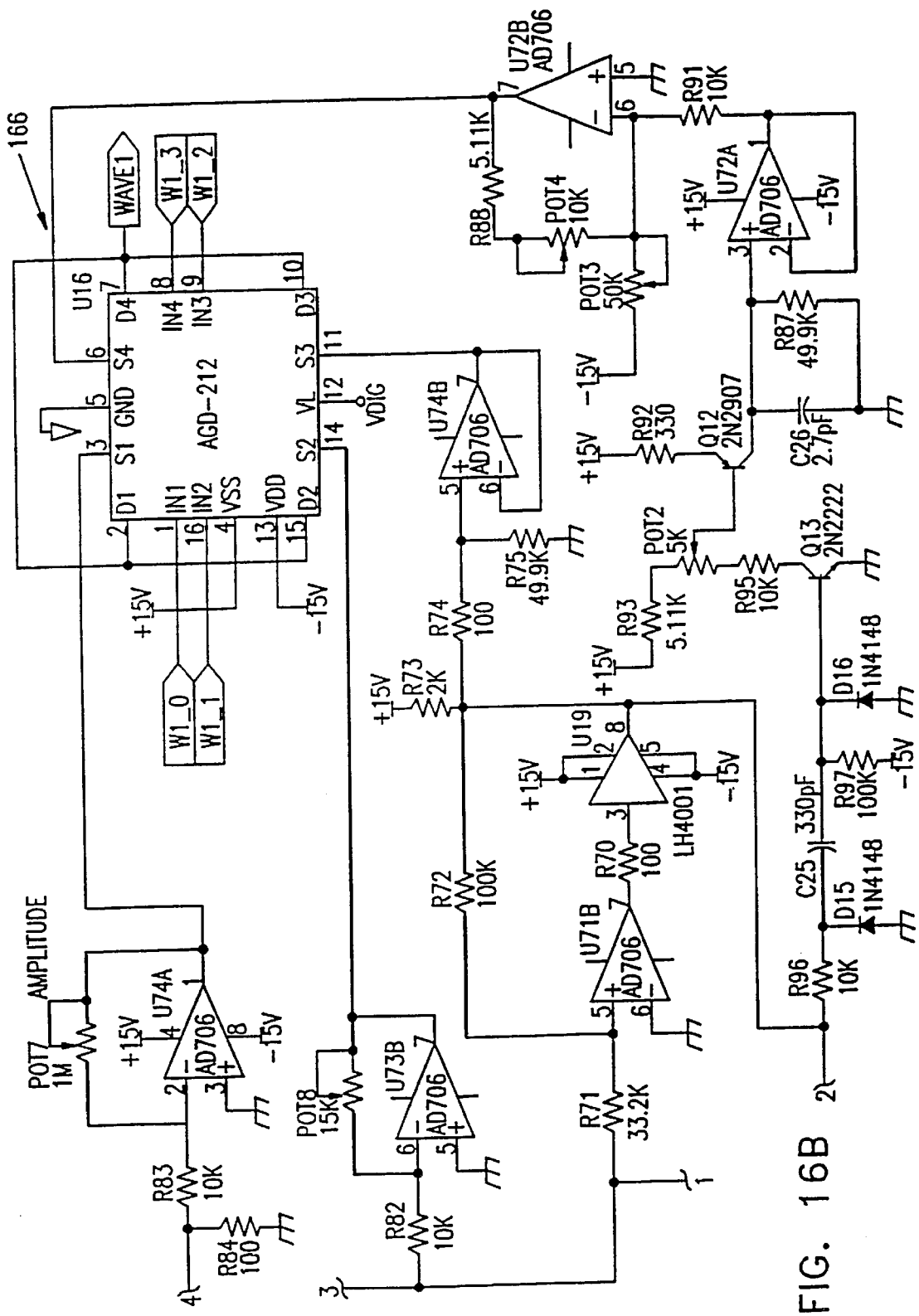
Figure 17A:
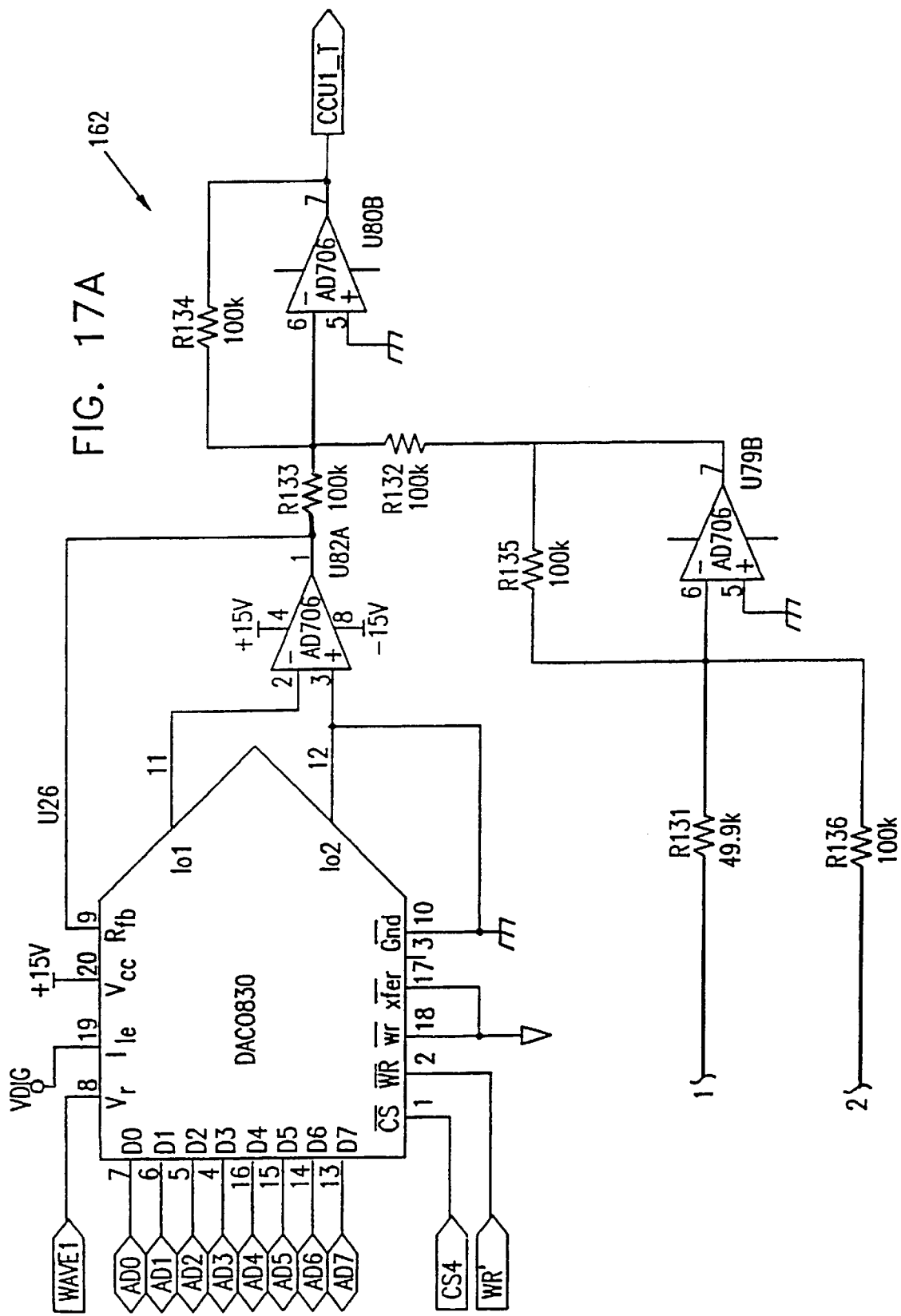
Figure 17B:
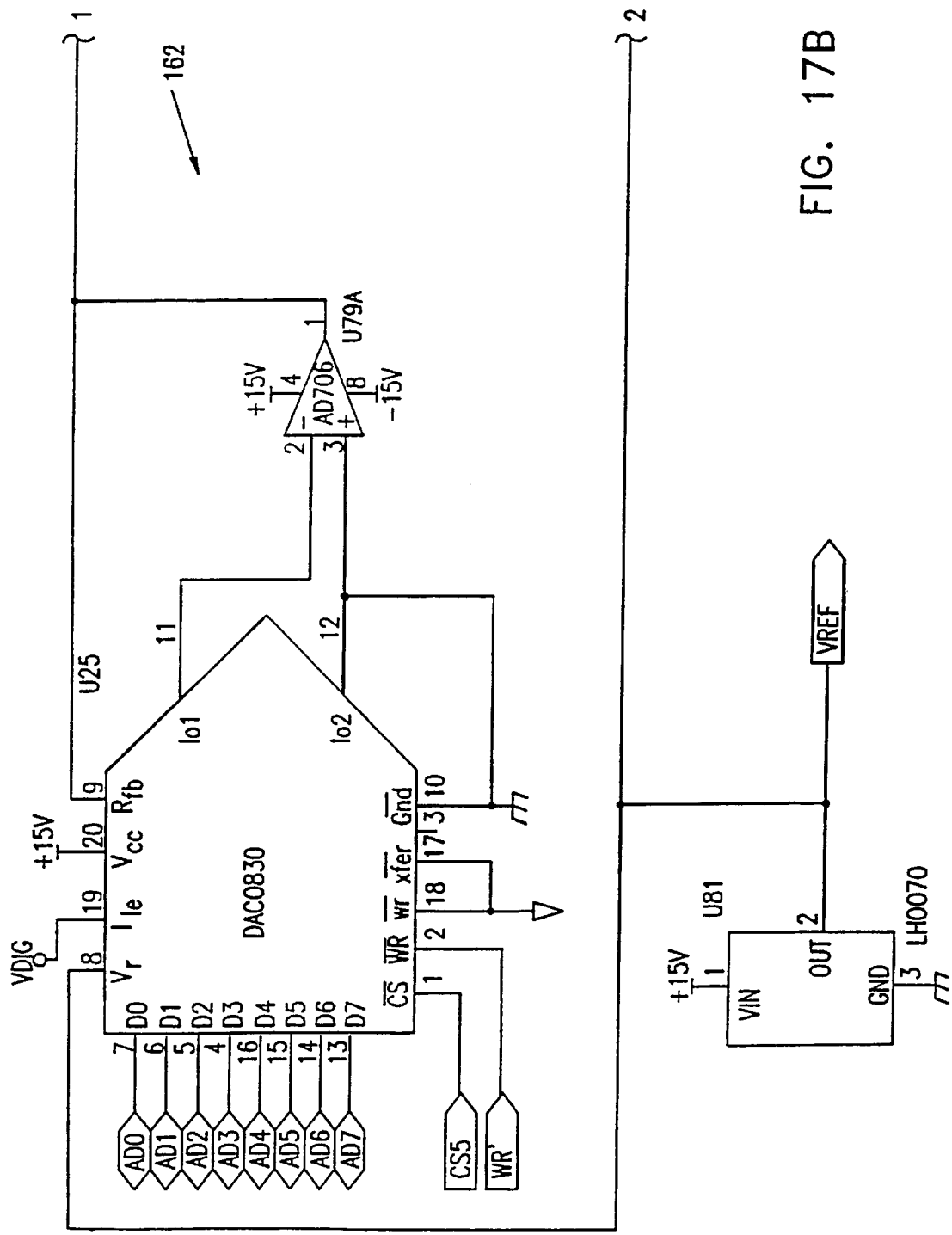
Figure 17C:
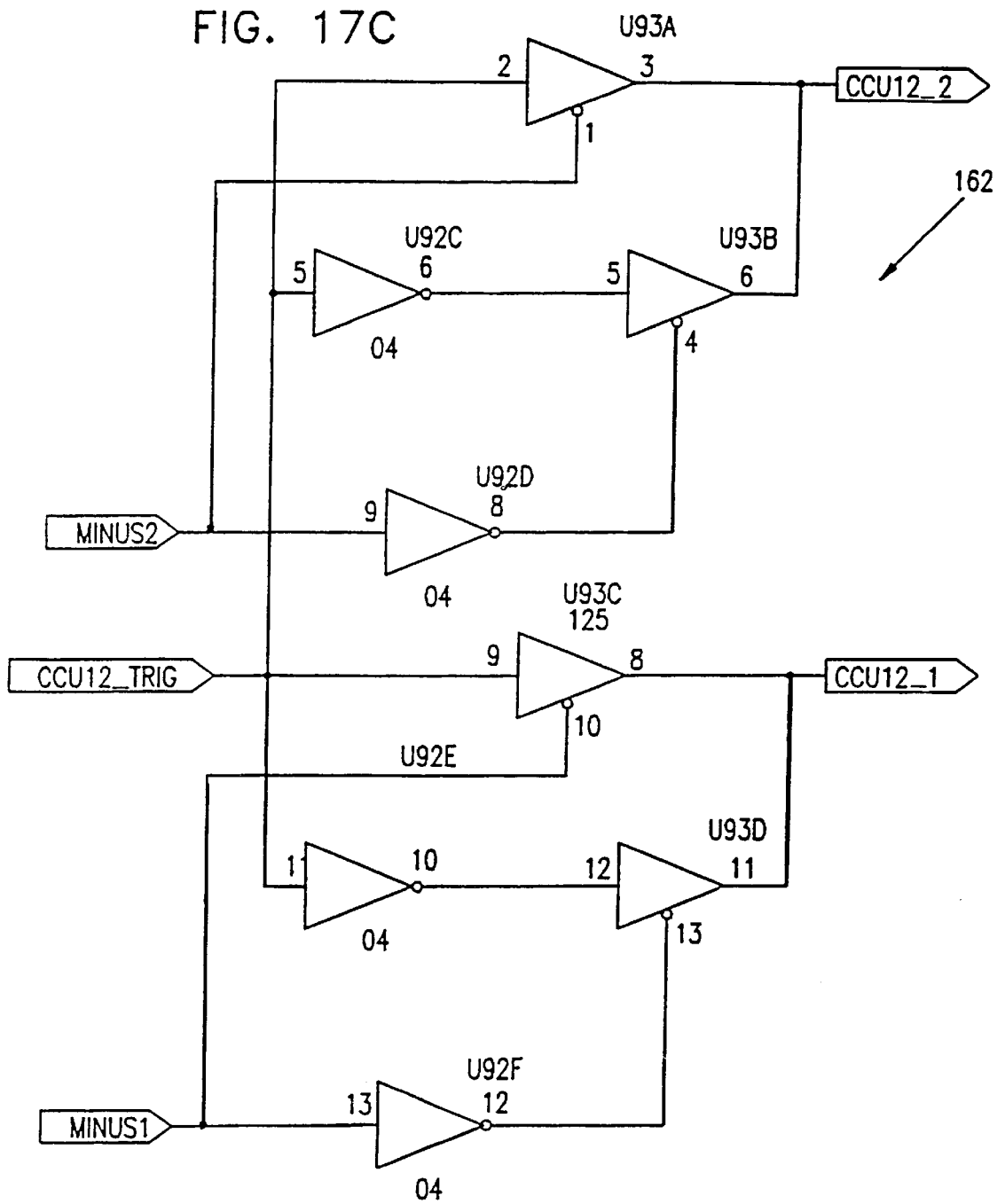
Figure 18:
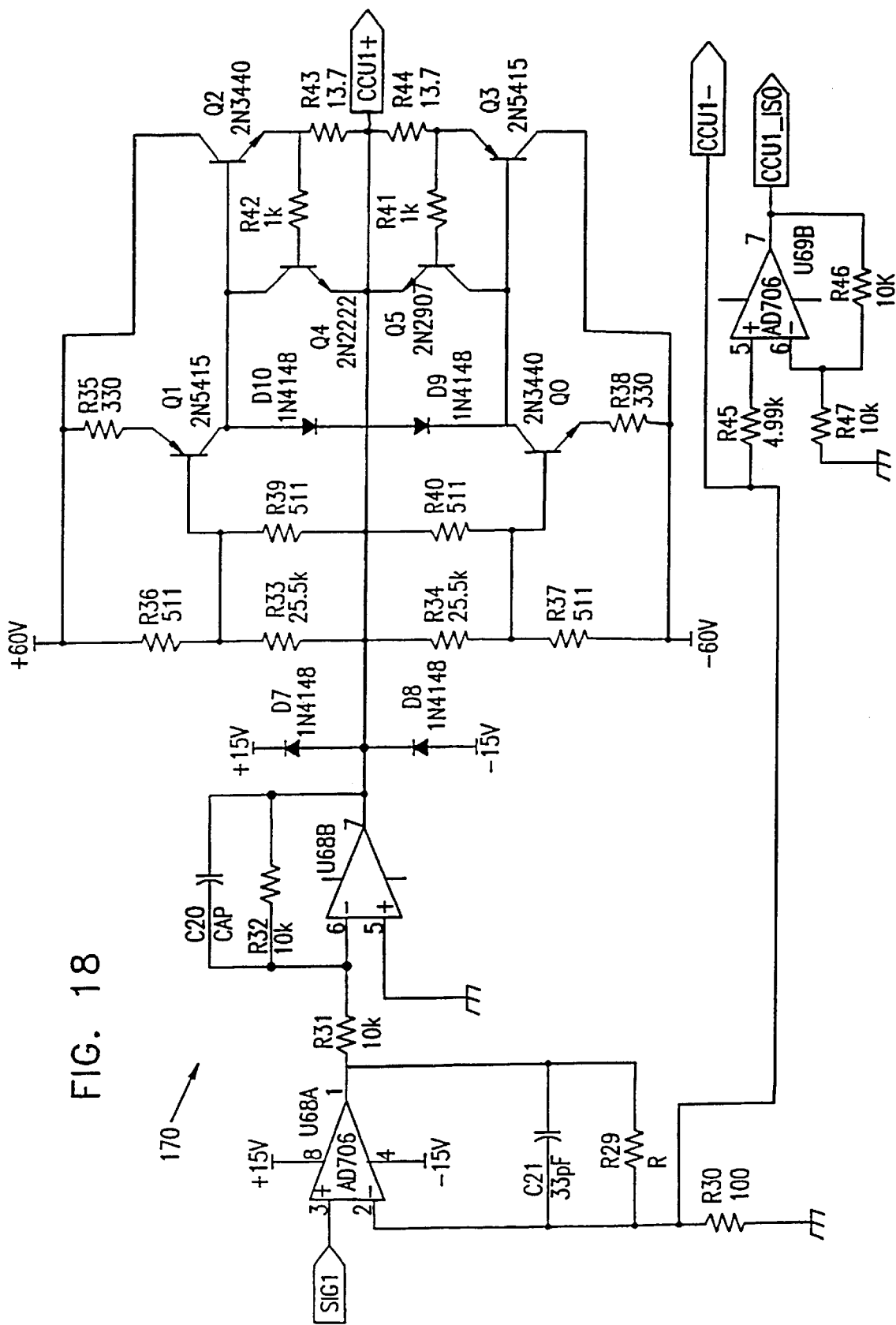
Figure 19A:
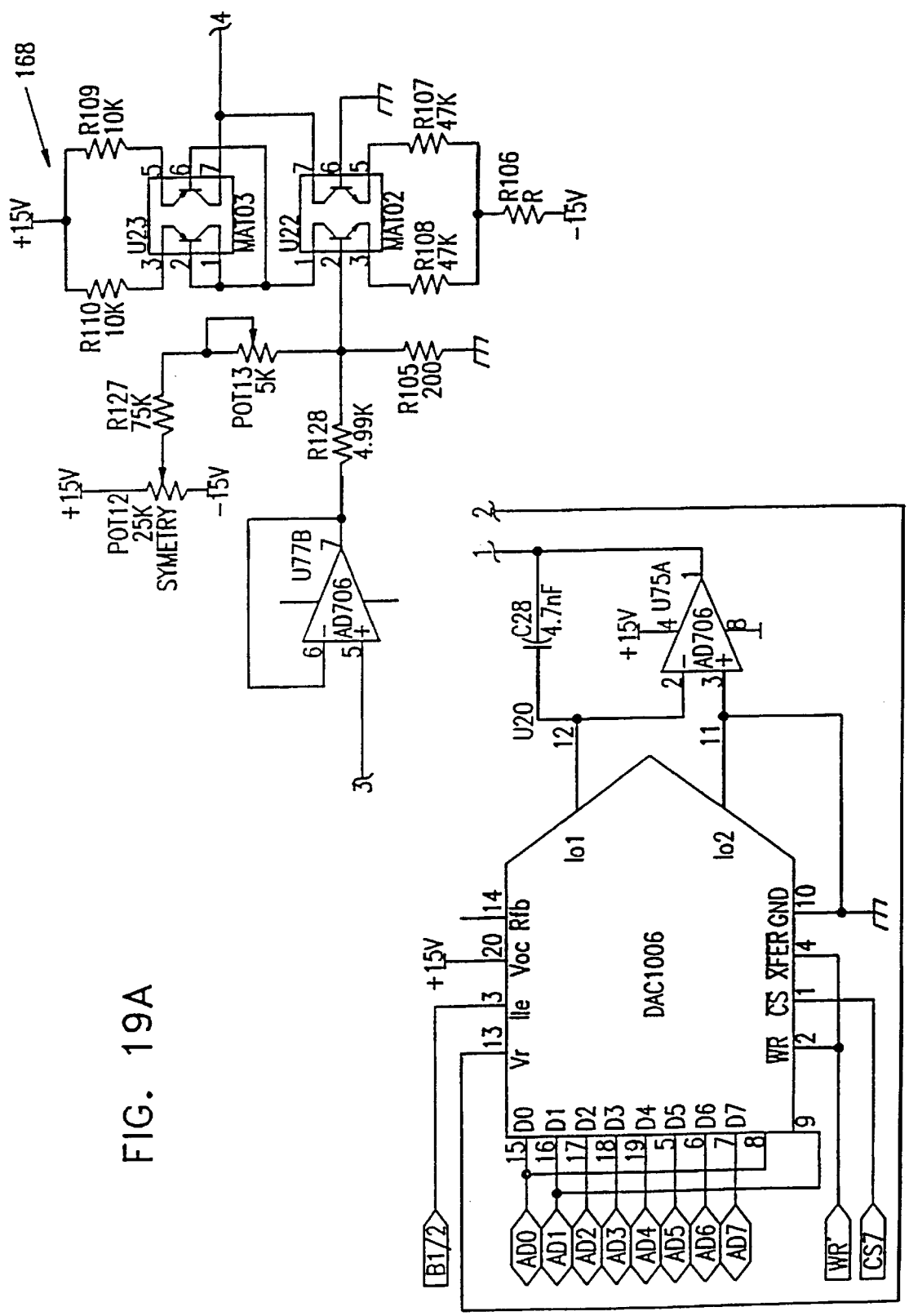
Figure 19B:
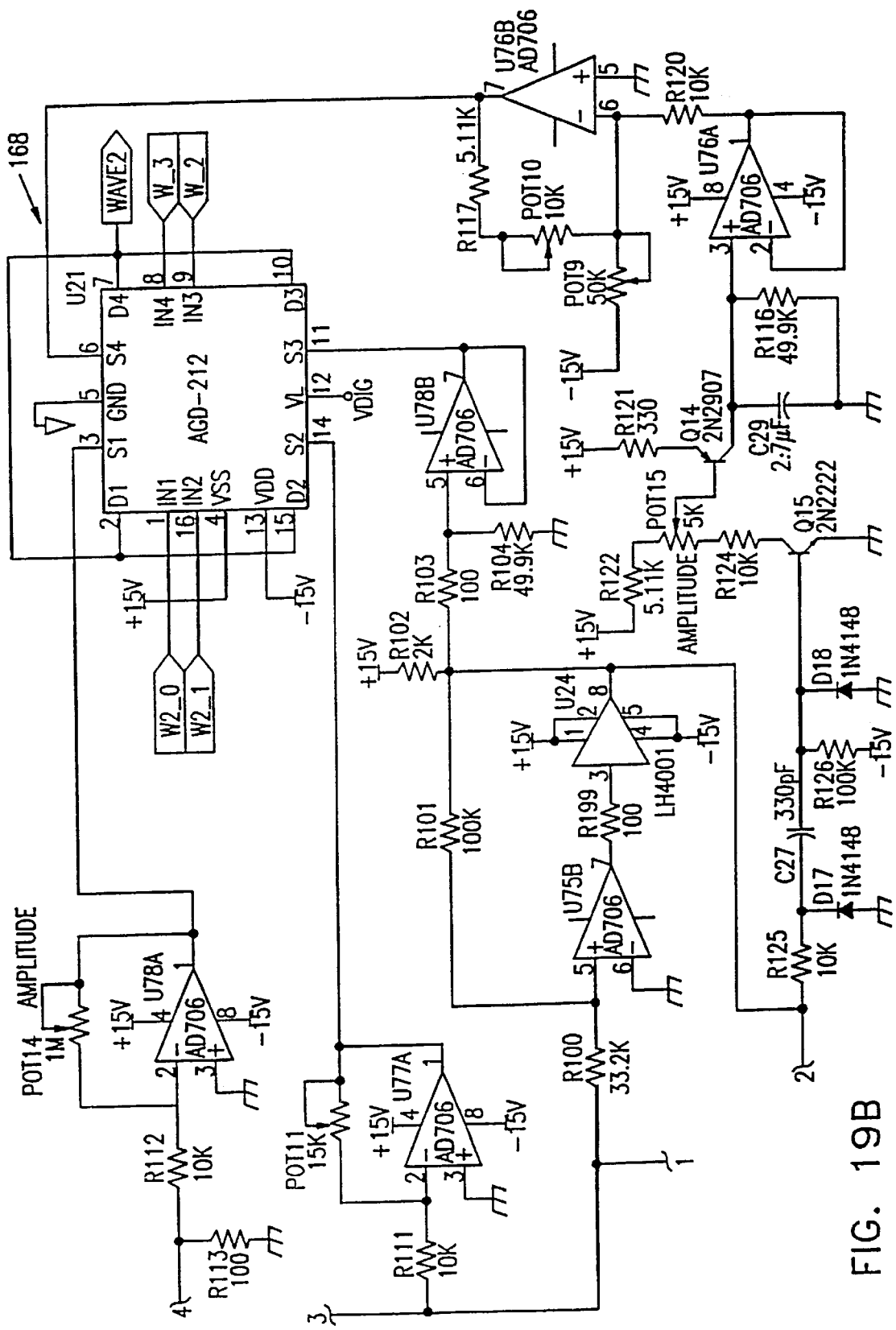
Figure 20A:
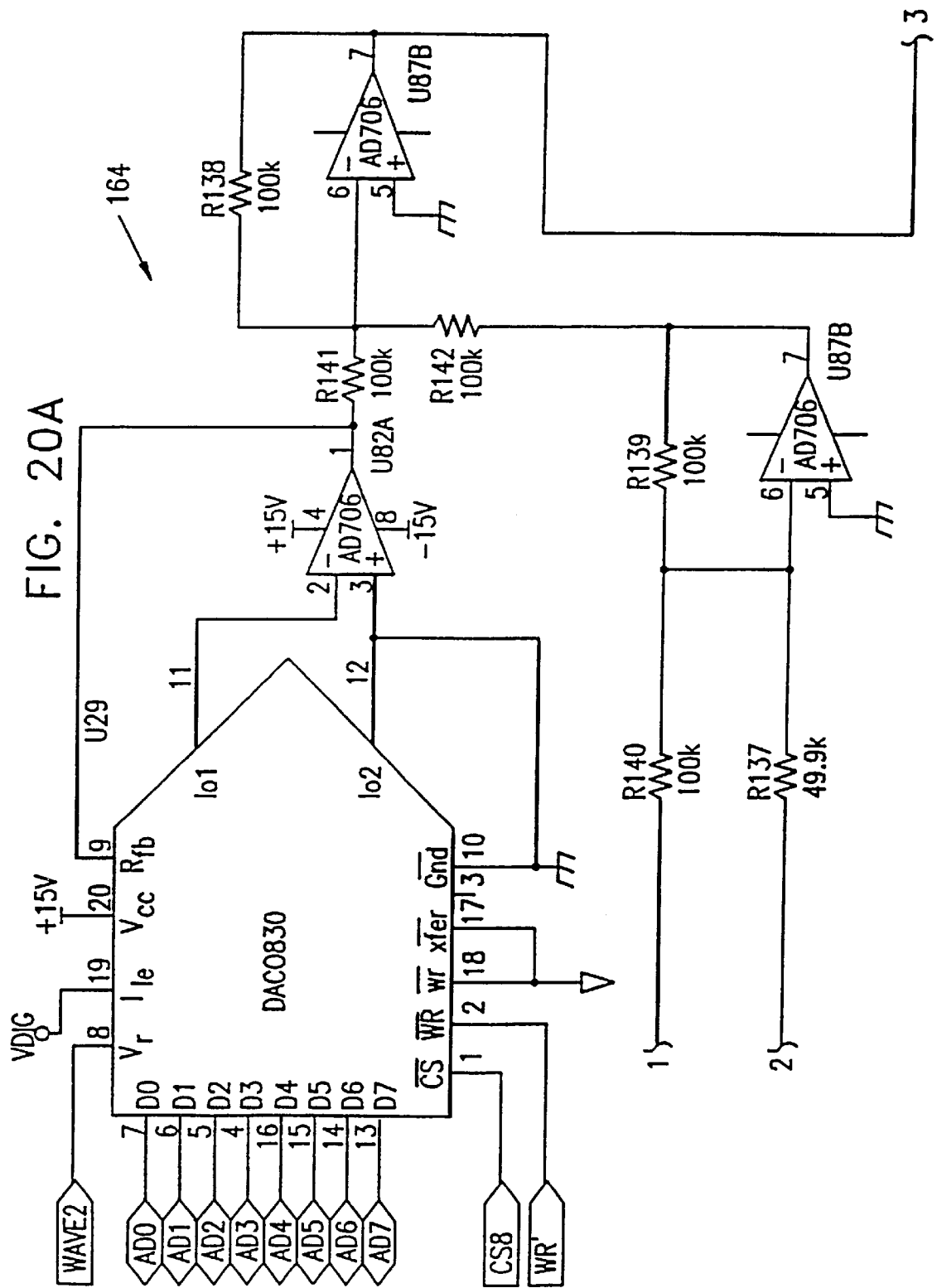
Figure 20B:
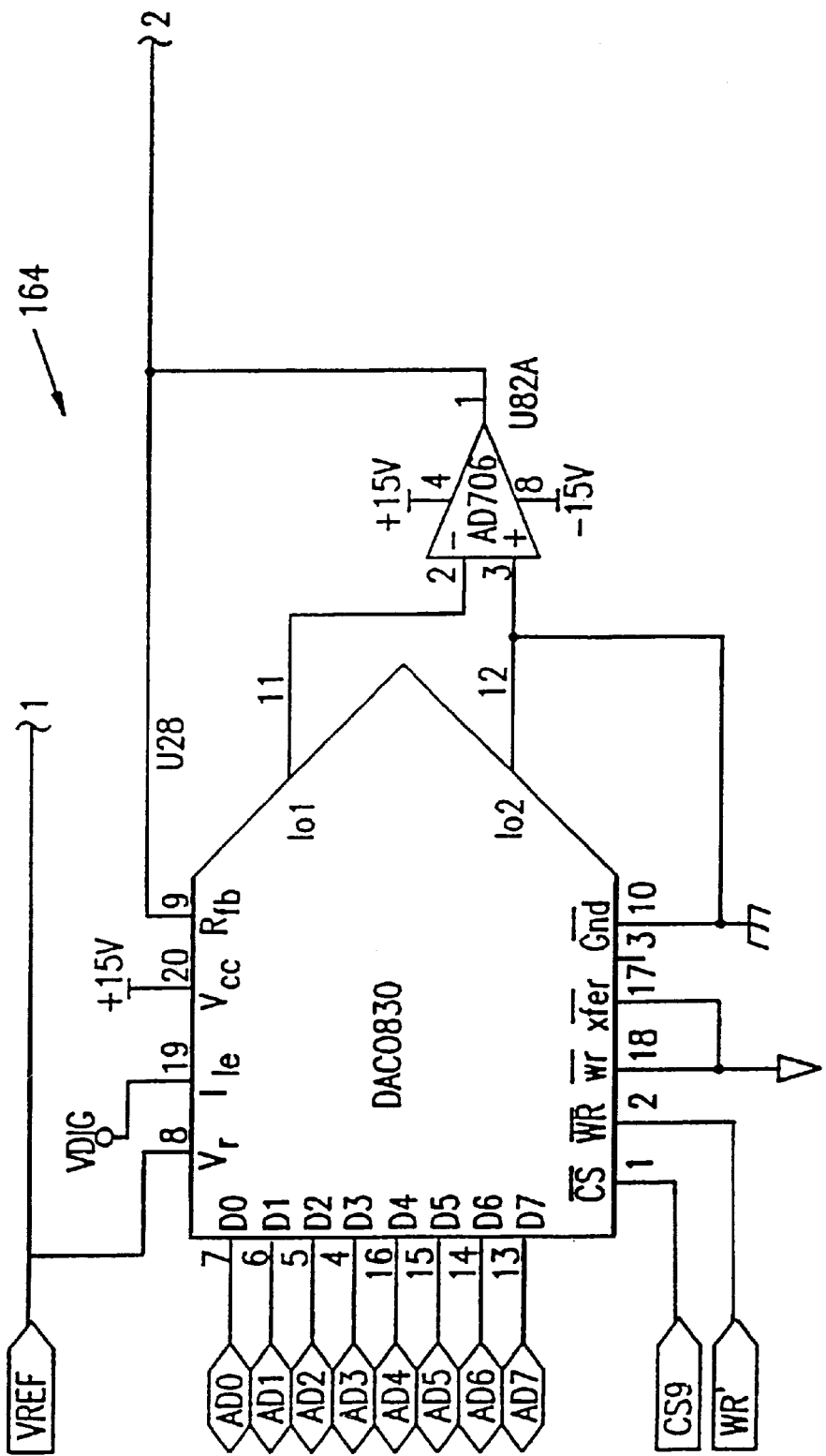
Figure 20C:
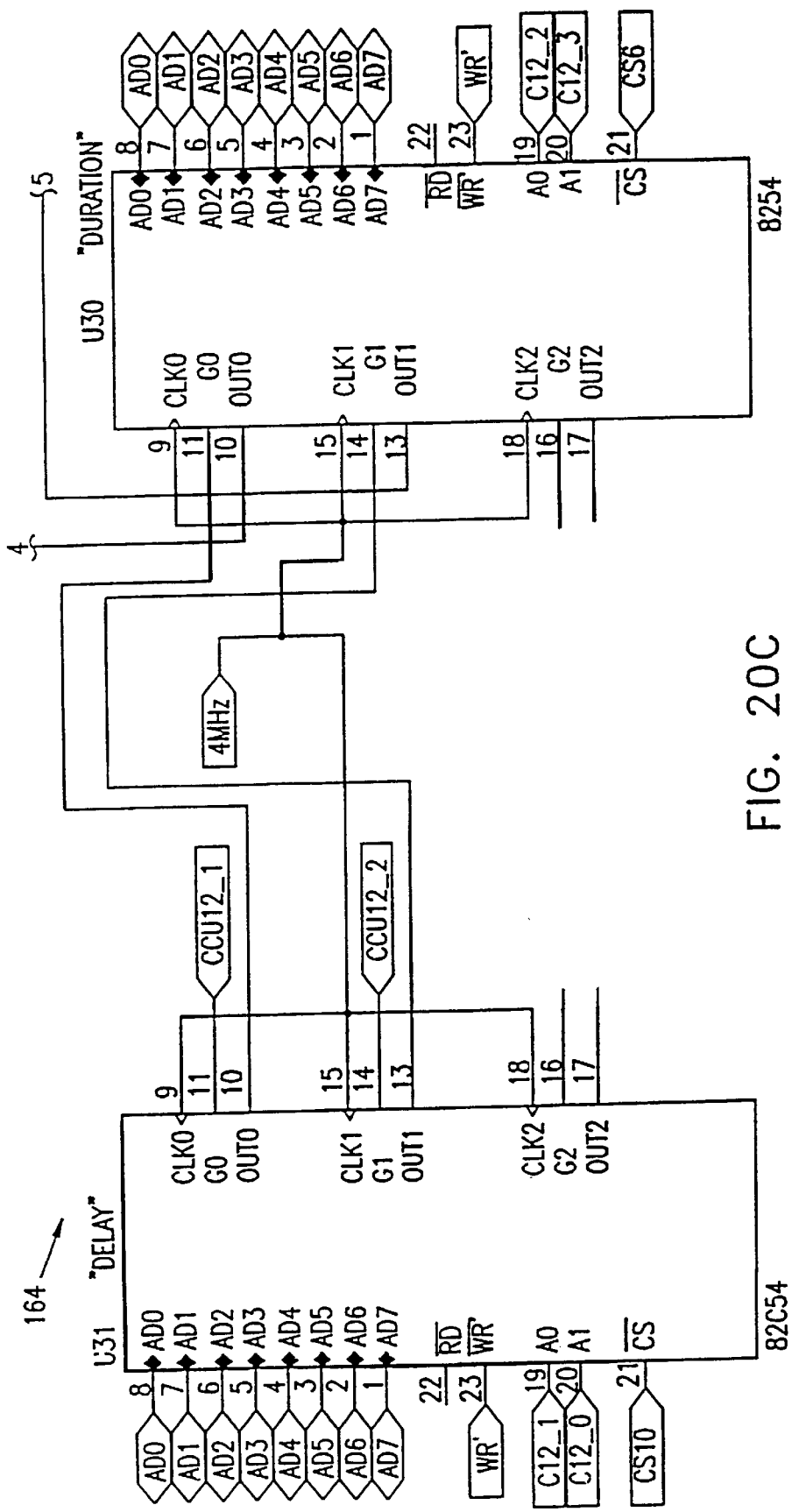
Figure 20D:
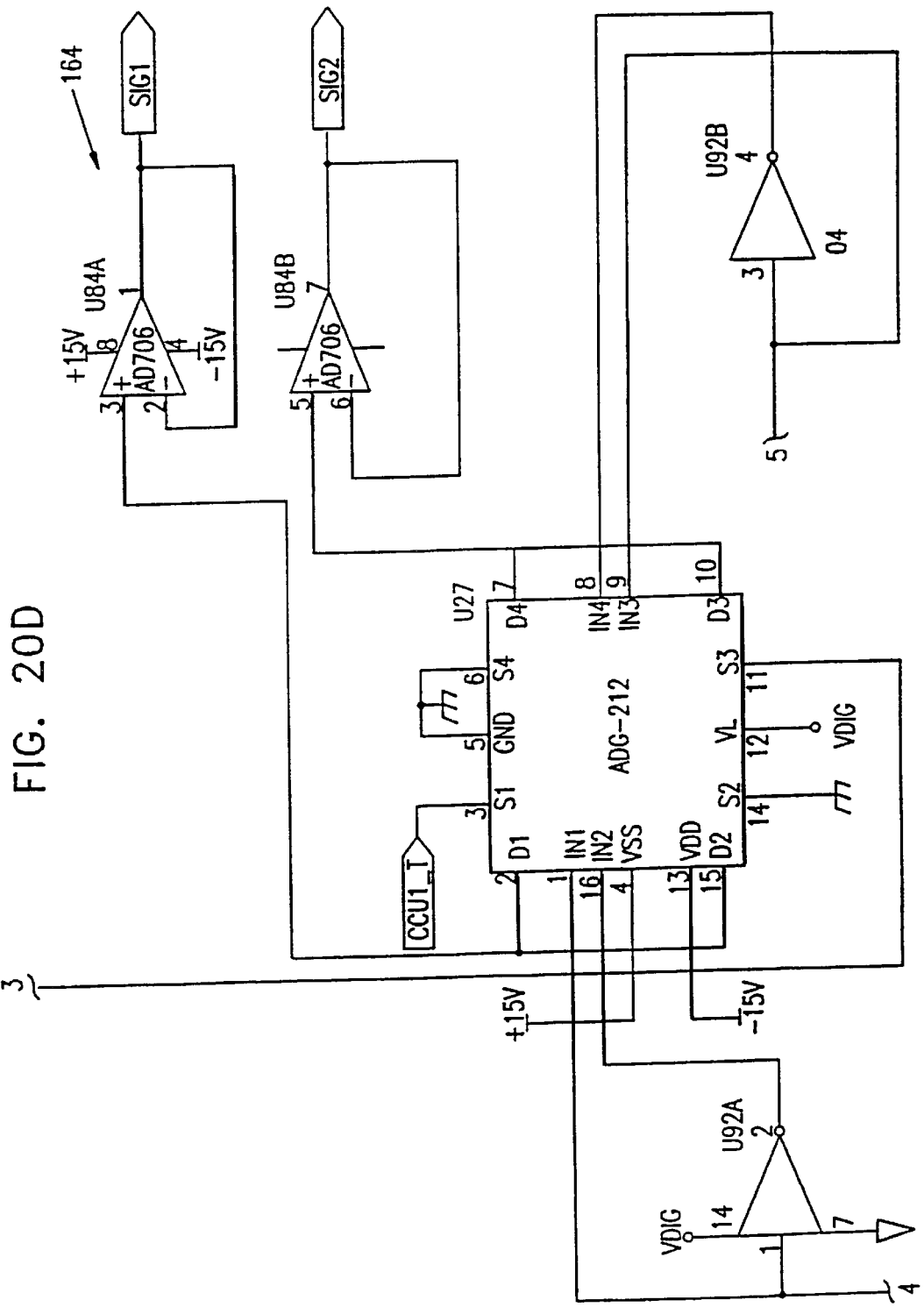
Figure 21:
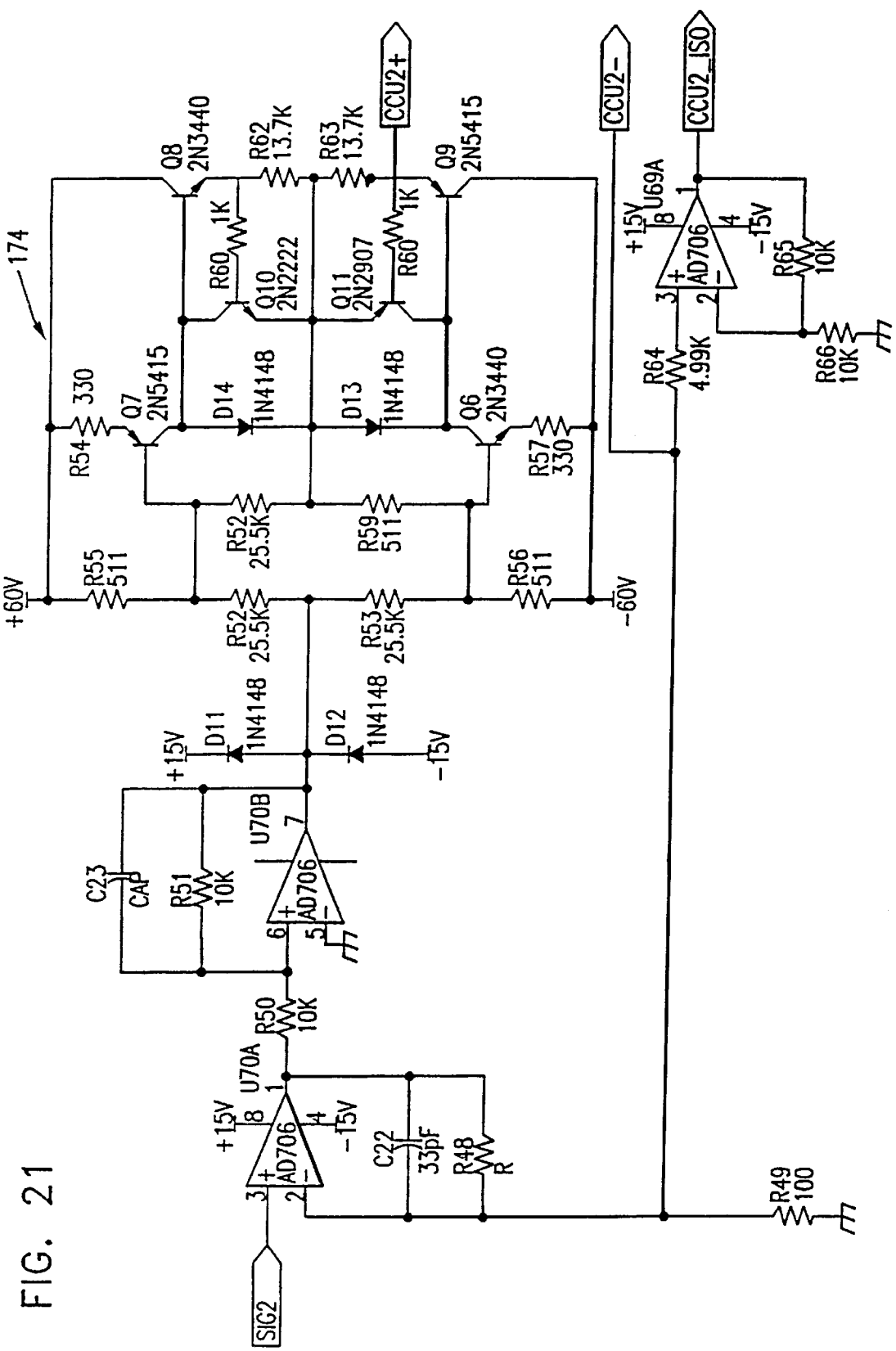
Figure 22:
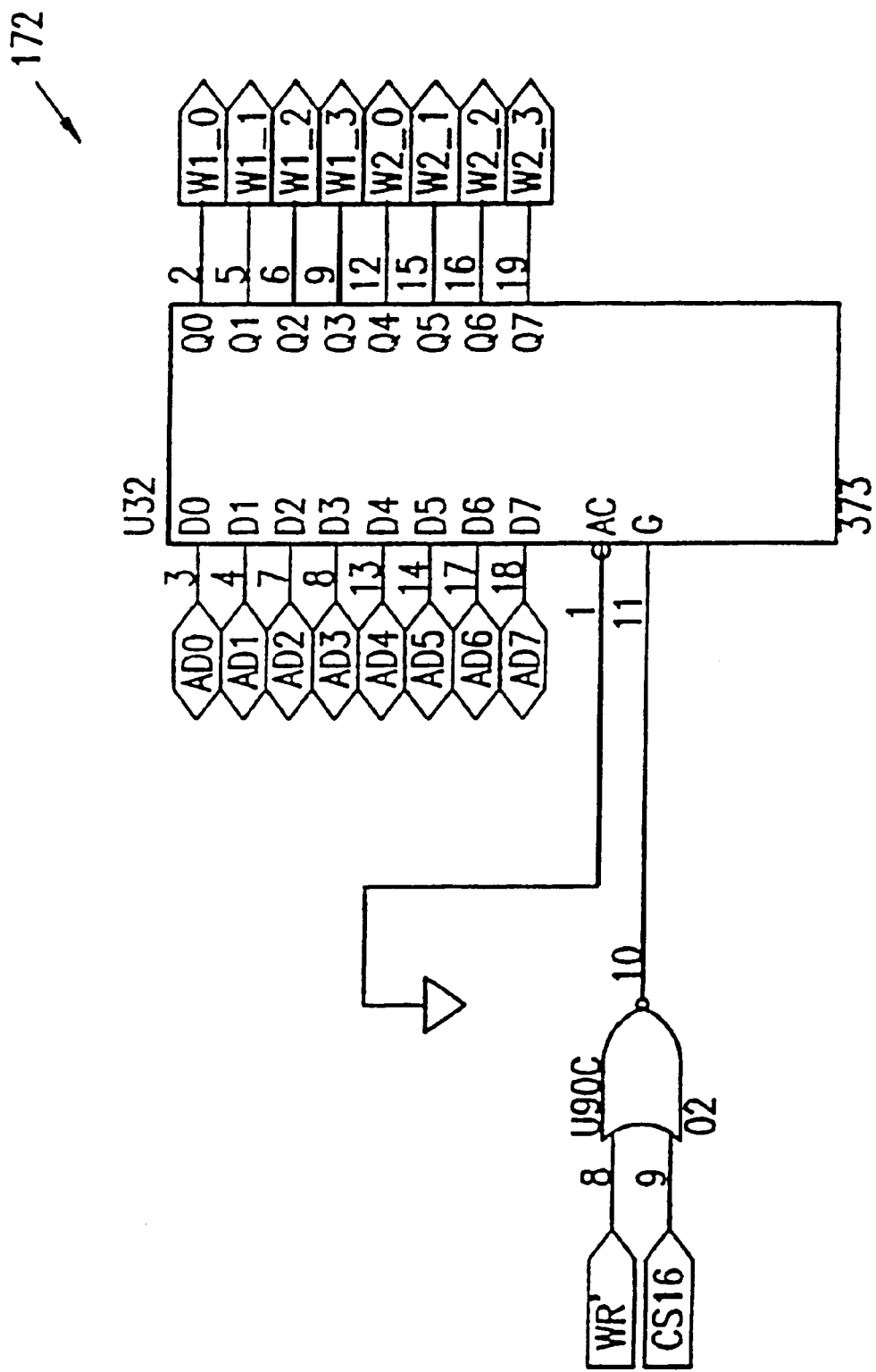

FIGS. 15A, 15B and 15C illustrate first CCU section 140, which generates two channels of non-excitatory stimulation pulses. CCU section 140 includes two control units 162 and 164, waveform generators 166 and 168, power units 170 and 174, and a waveform selector 172. FIGS. 16A and 16B show details of waveform generator 166, which drives a first one of the two non-excitatory channels, while FIGS. 19A and 19B show waveform generator 168, which is substantially similar to generator 166 and drives the second channel. FIGS. 17A, 17B and 17C illustrate control unit 162, which receives and scales the waveform from generator 166. FIG. 17C shows timing control logic common to both control units 162 and 164. FIGS. 20A, 20B, 20C and 20D illustrate control unit 164, wherein FIGS. 20A and 20B show waveform scaling circuitry similar to that in FIGS. 17A and 17B. FIGS. 20C and 20D include circuitry for controlling the relative delays of the pulses generated by the two stimulation channels. FIGS. 18 and 21 show details of power units 174 and 178, respectively, and FIG. 22 illustrates wave selector 176.

Figure 23:
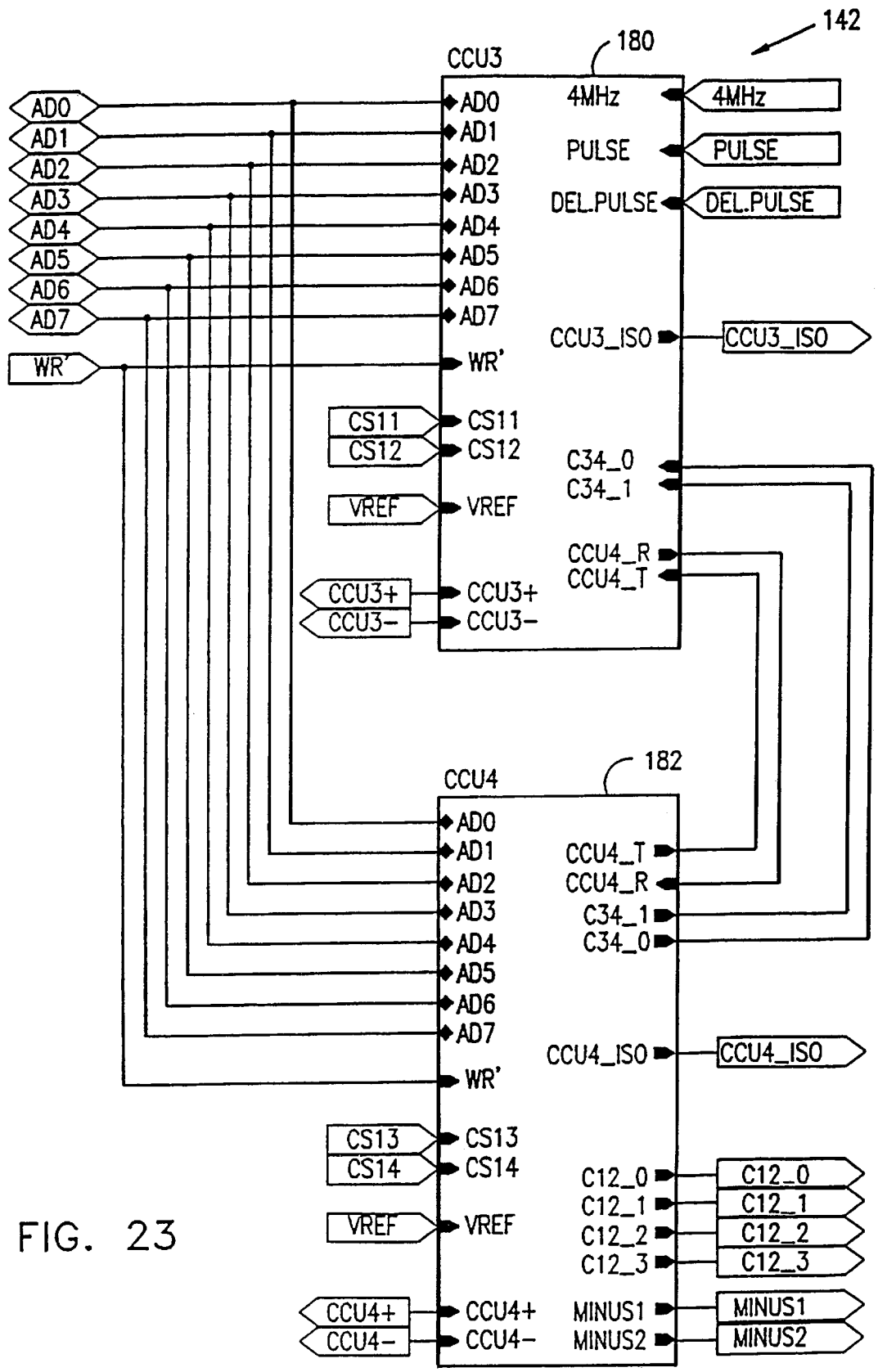
Figure 24A:
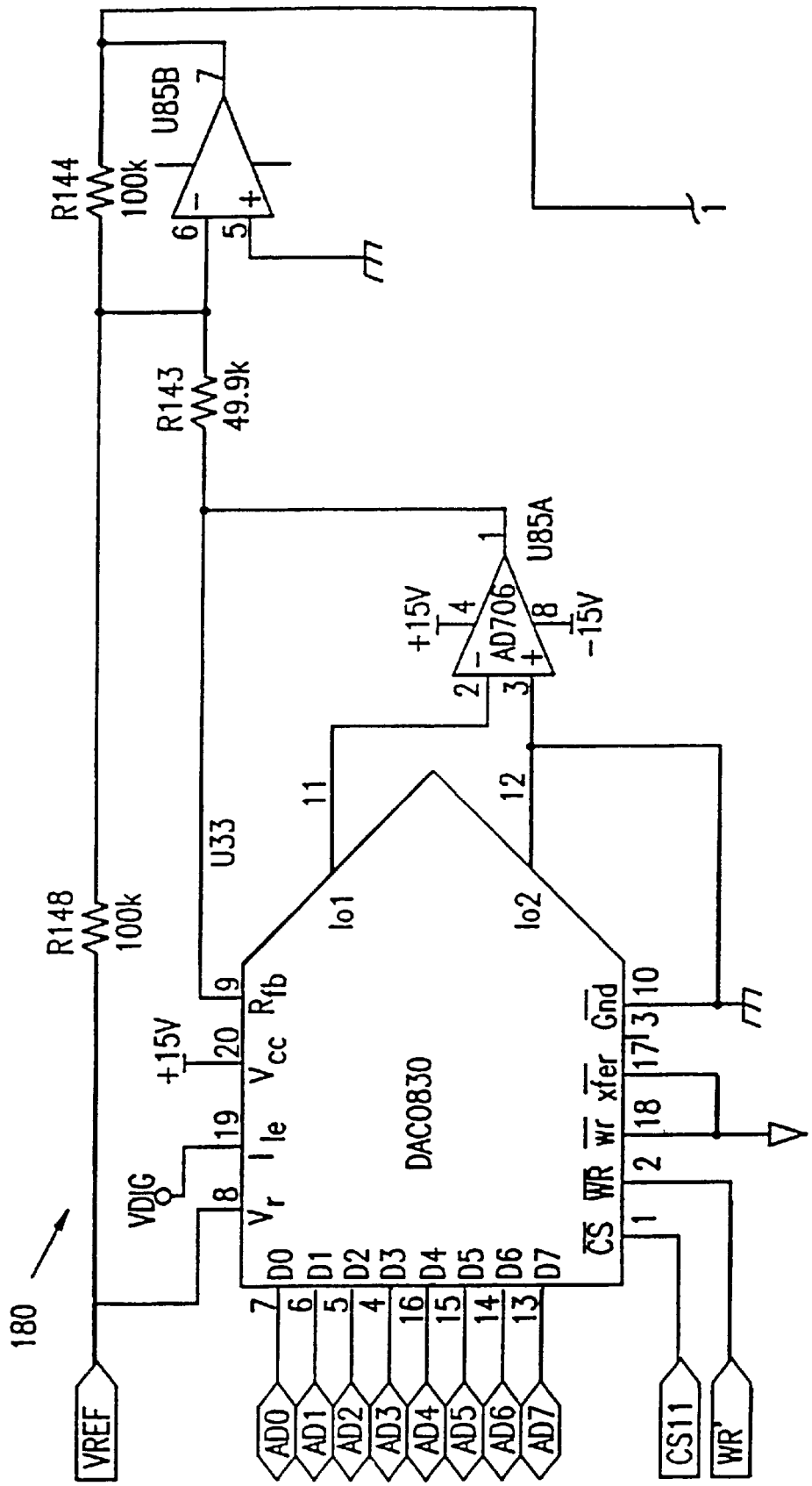
Figure 24B:
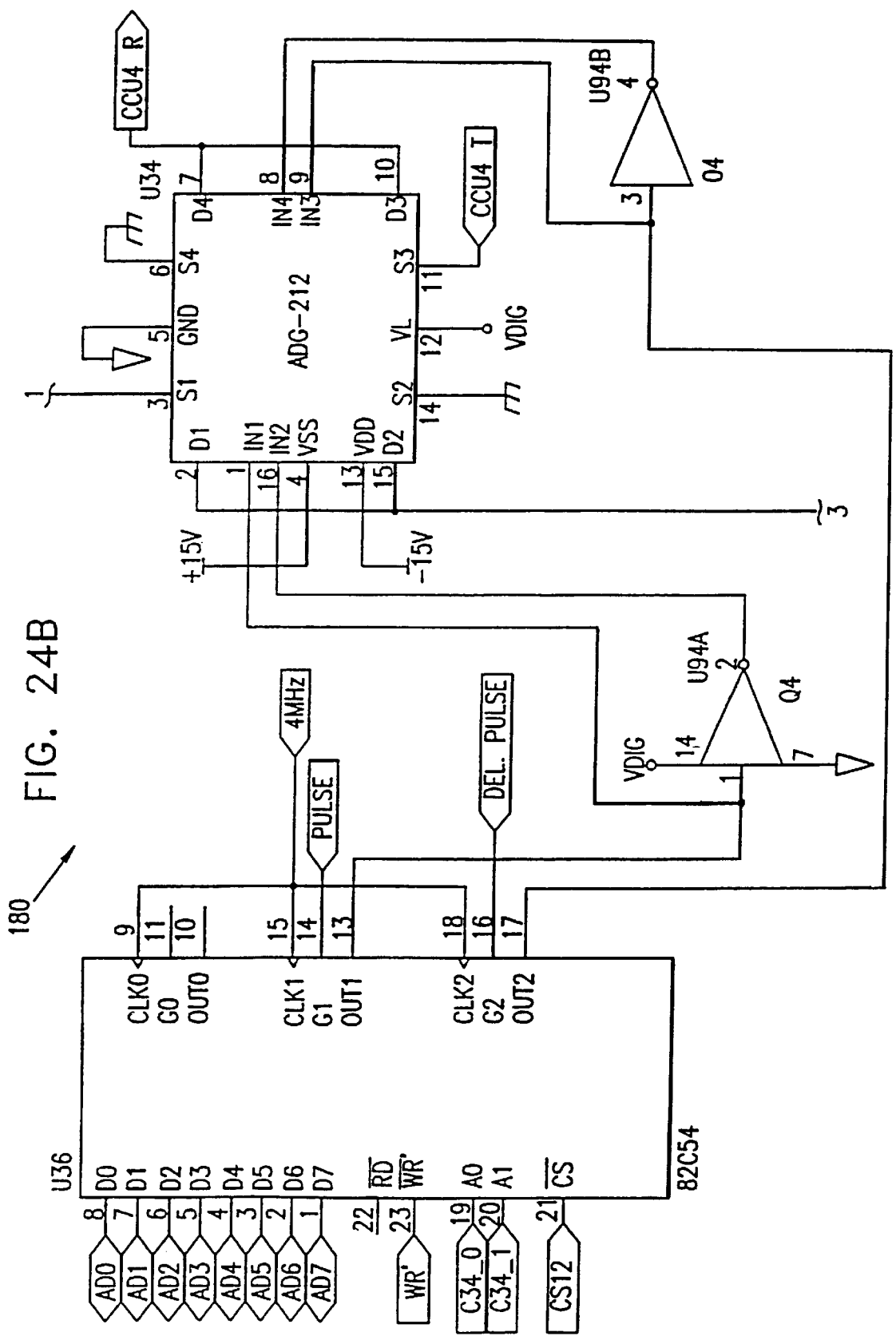
Figure 24C:
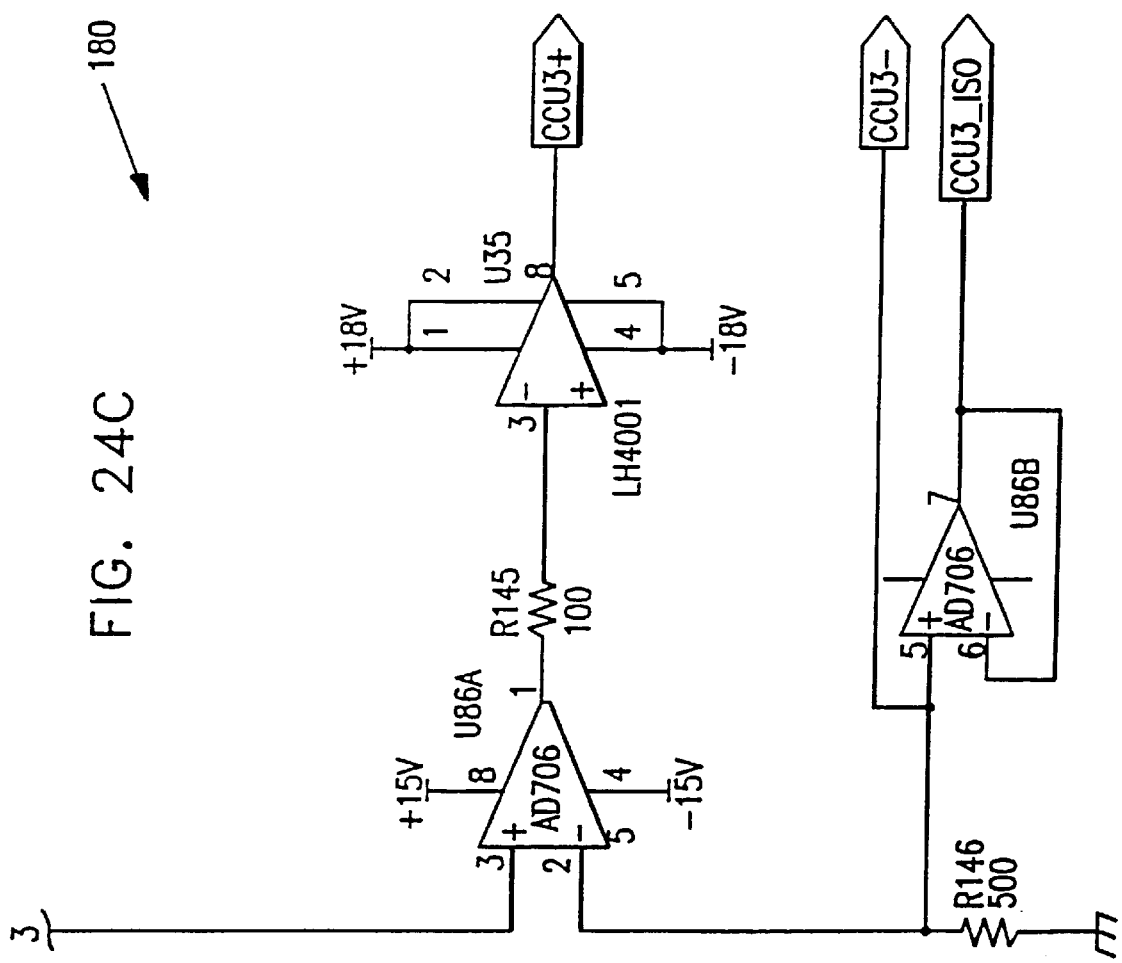
Figure 25A:
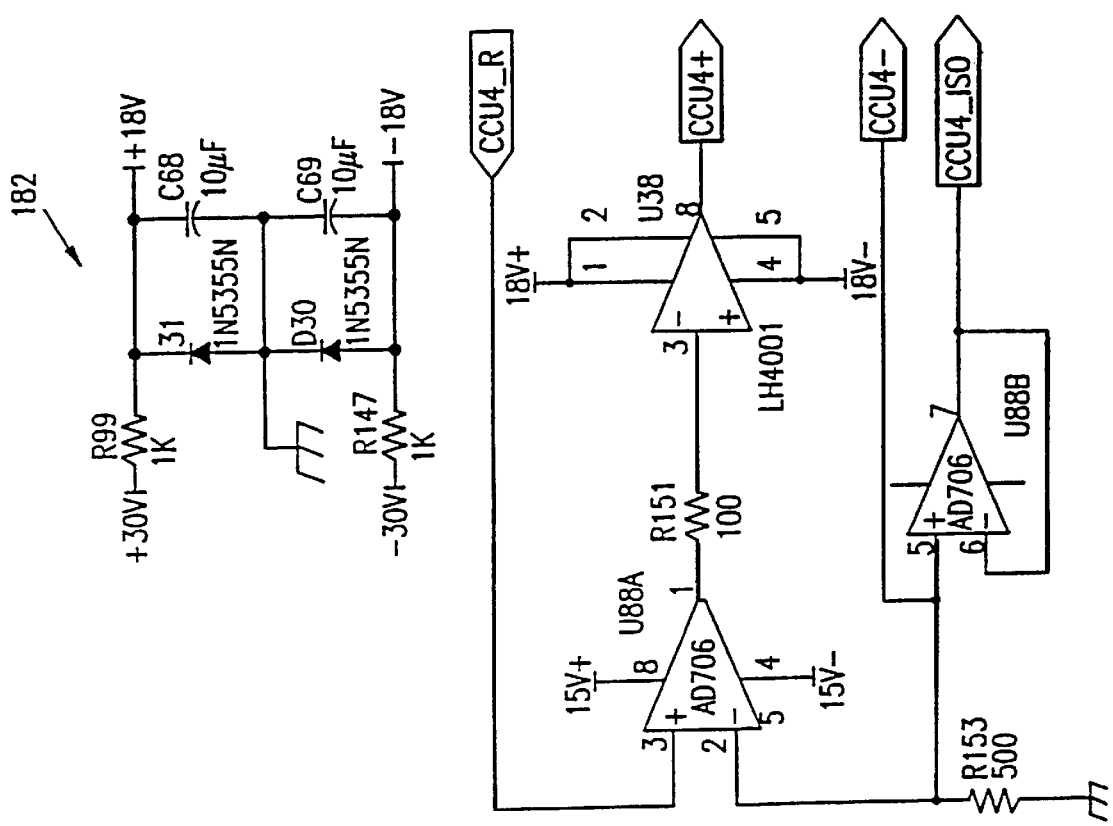
Figure 25A:
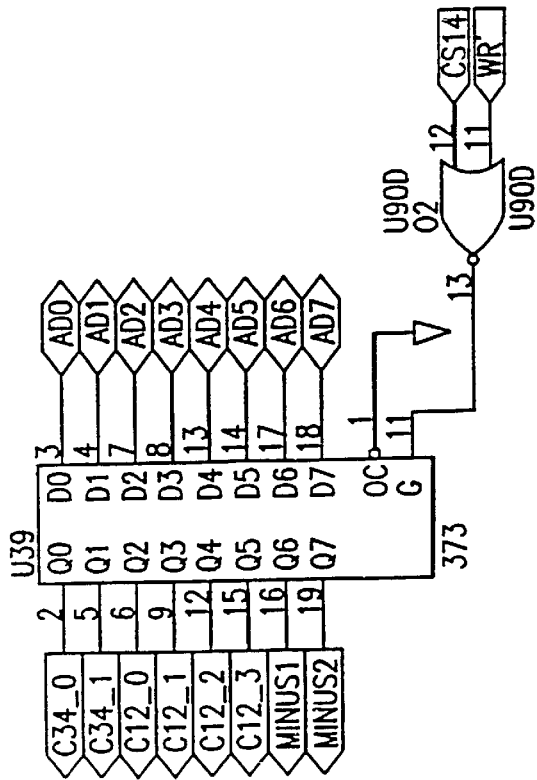
Figure 25B:
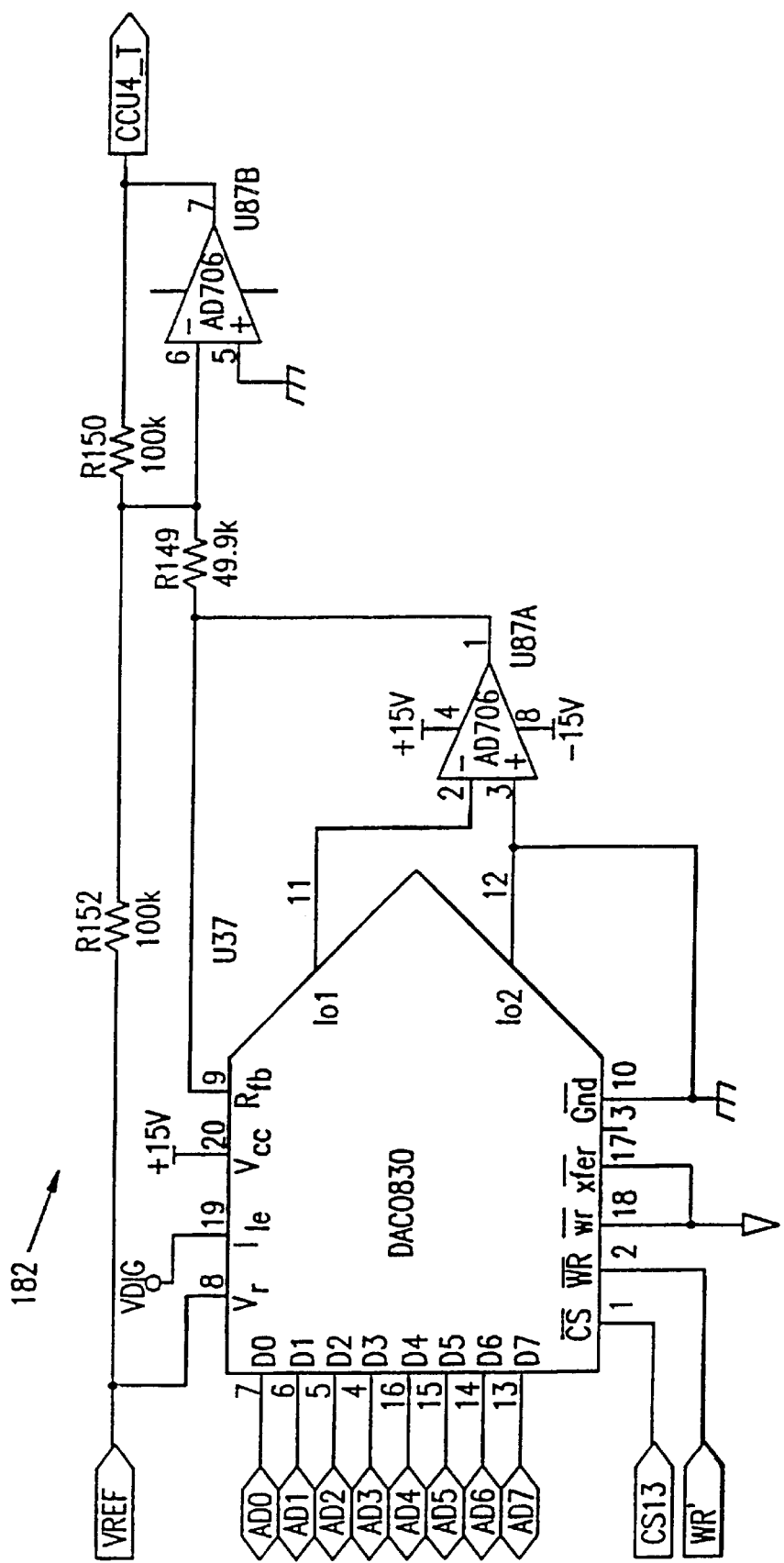
Figure 26:
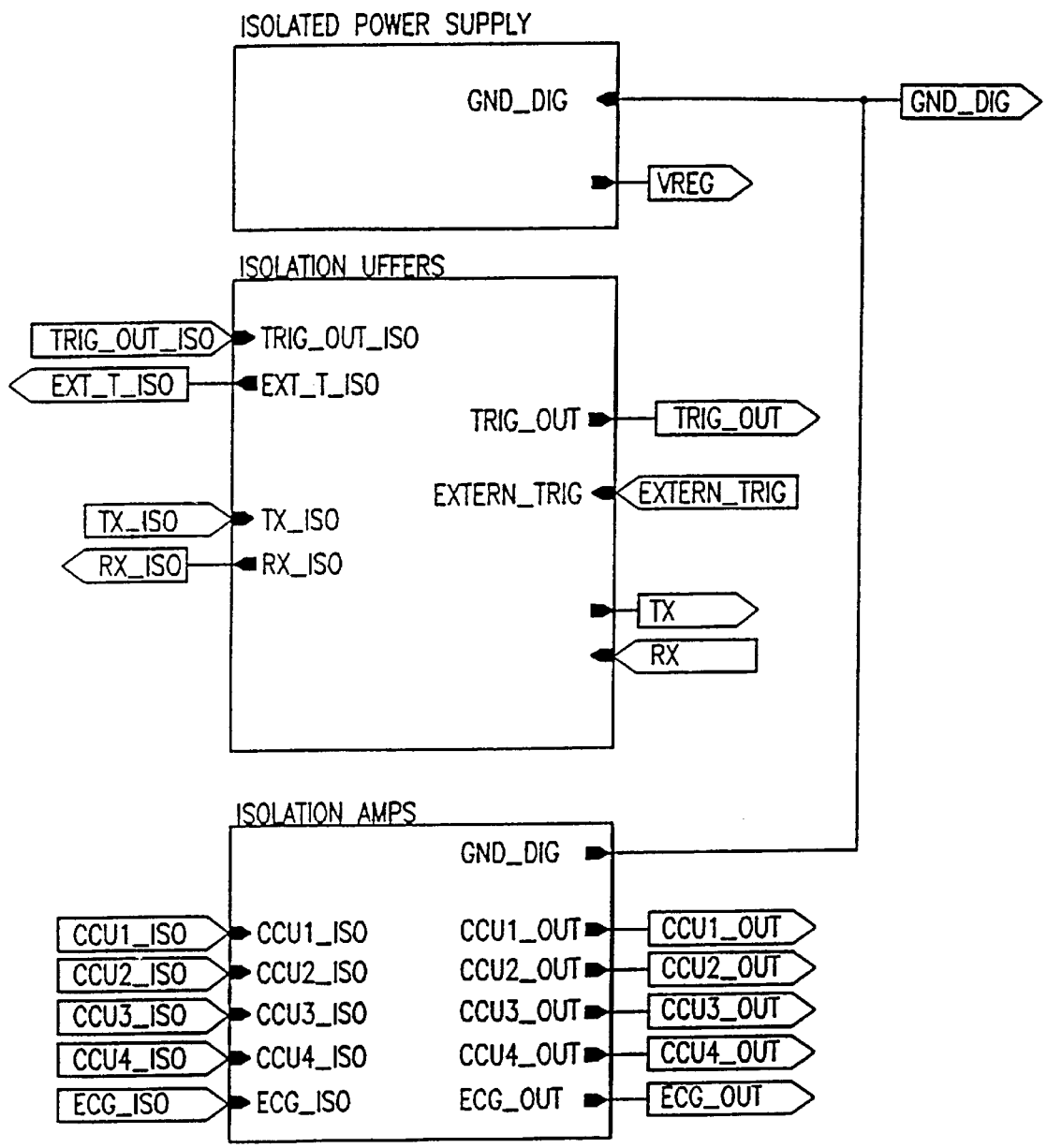
Figure 27A:
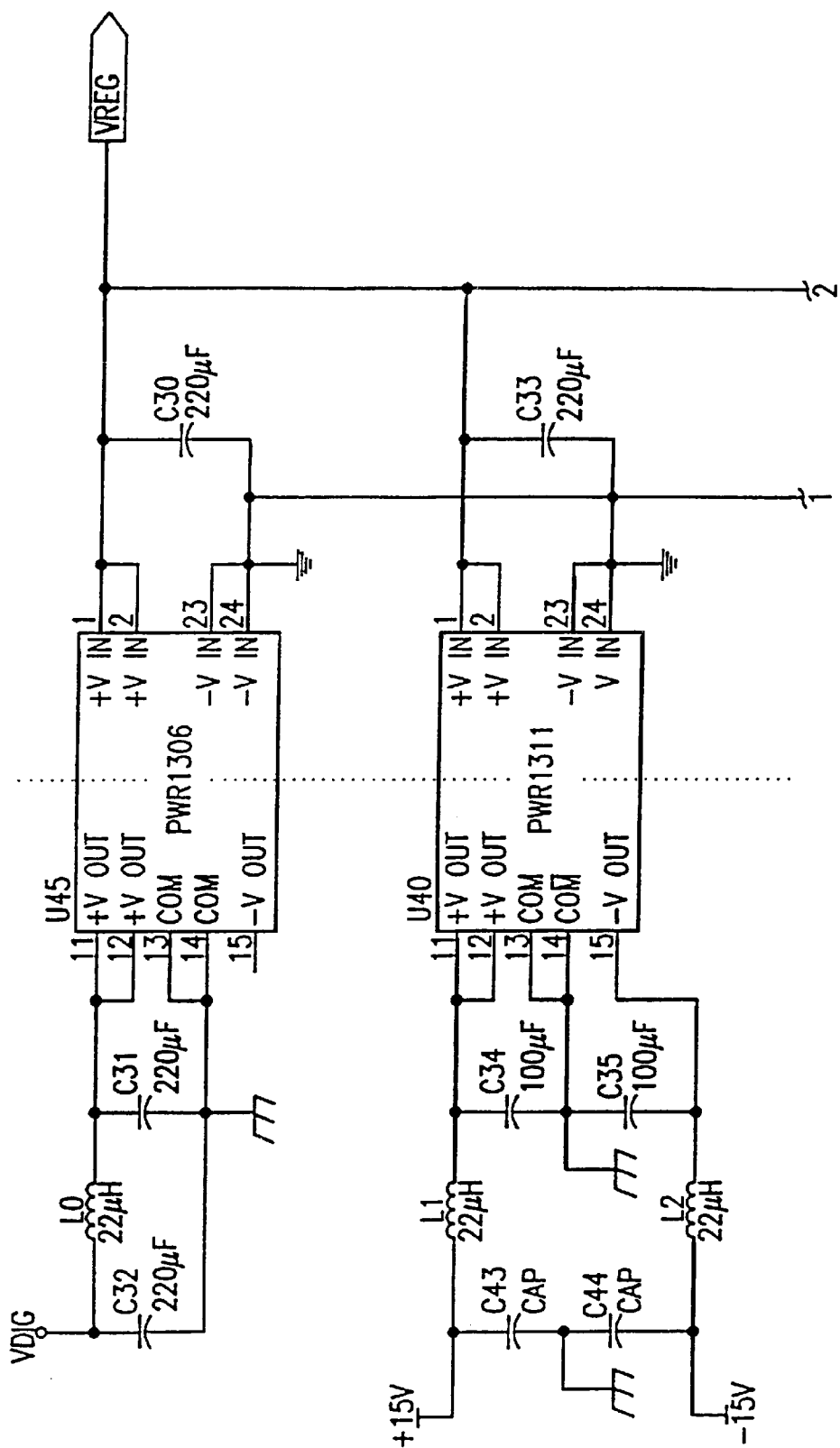
Figure 27B:
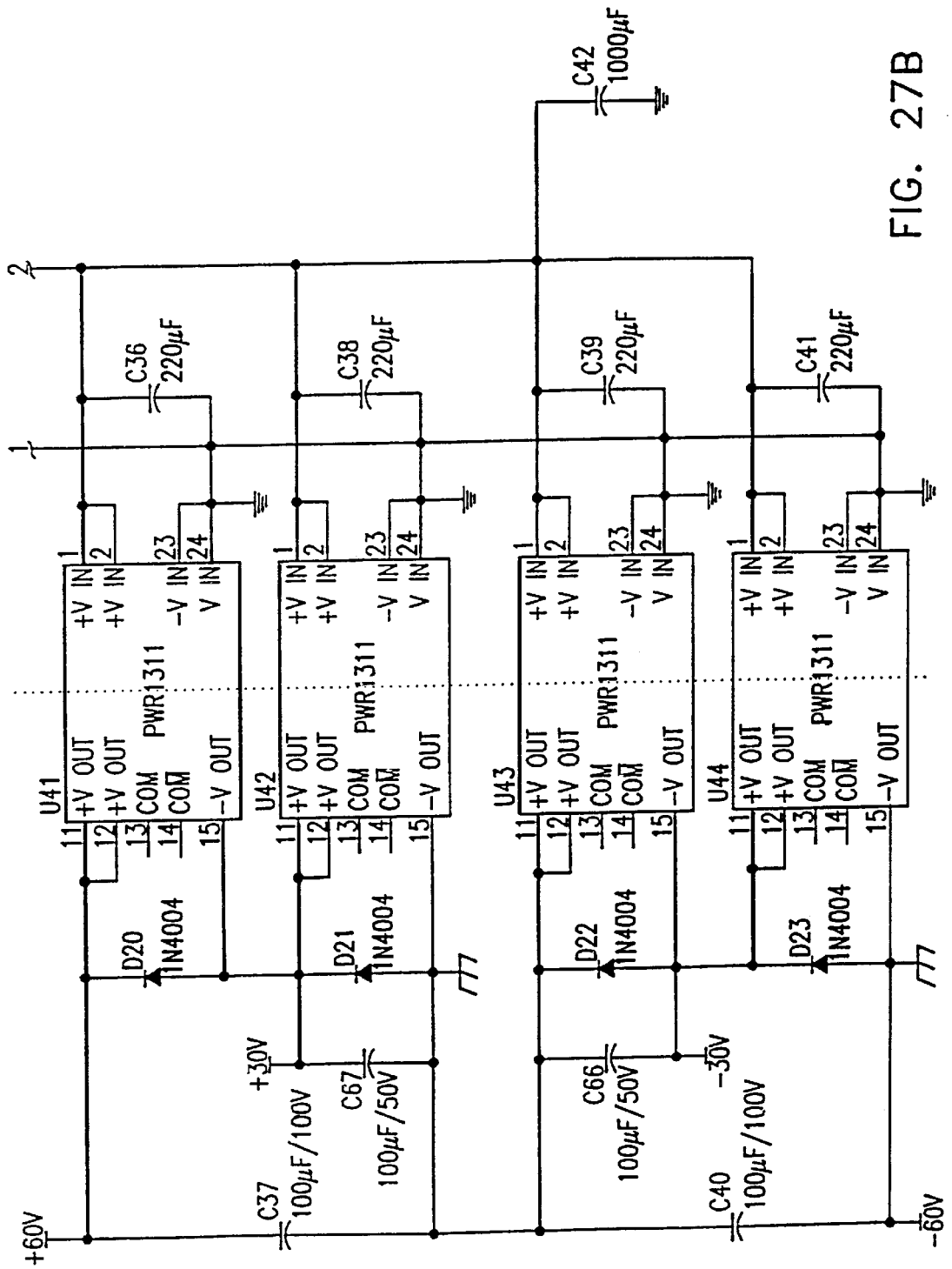
Figure 28:
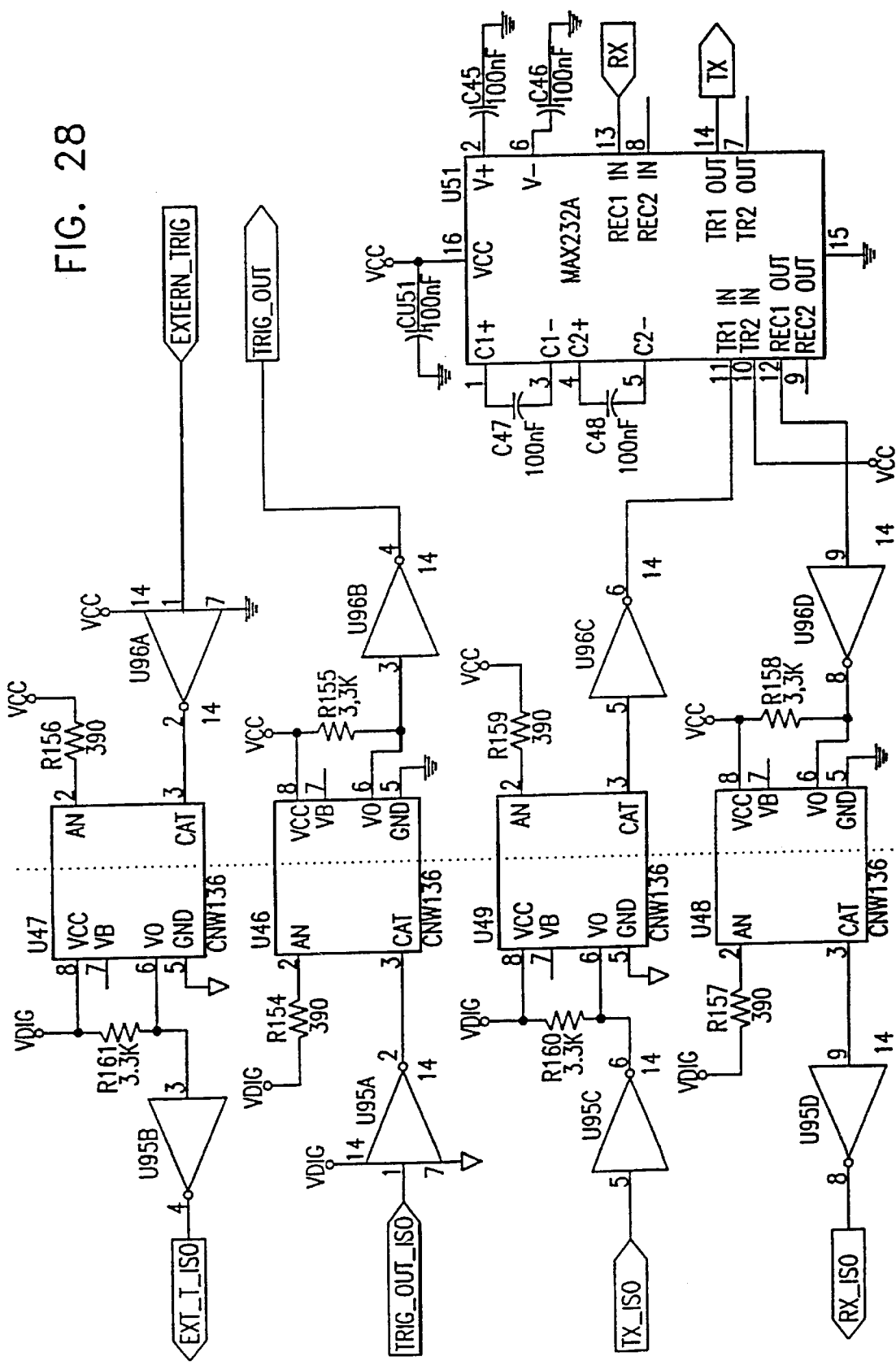
Figure 29A:
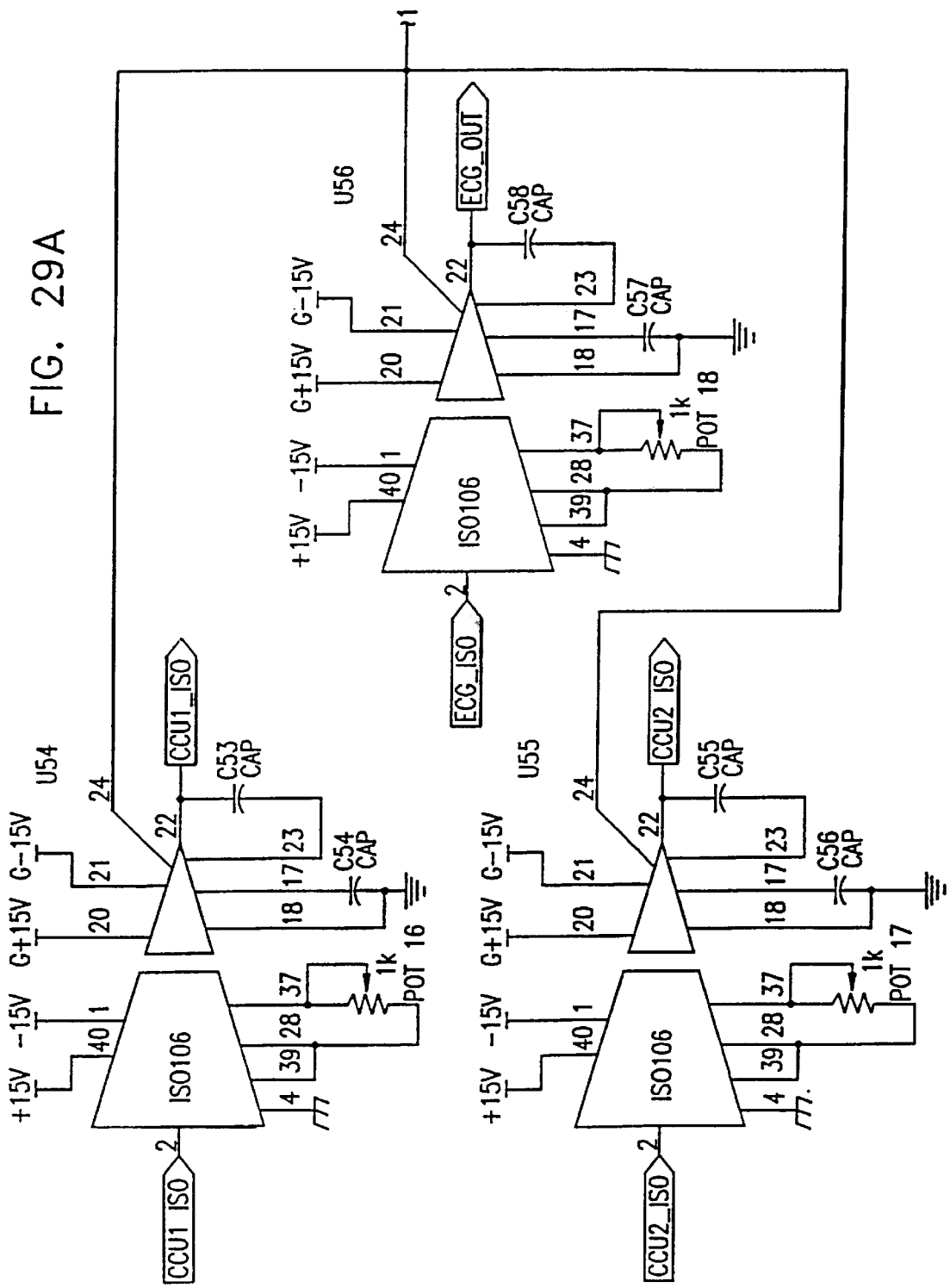
Figure 29B:
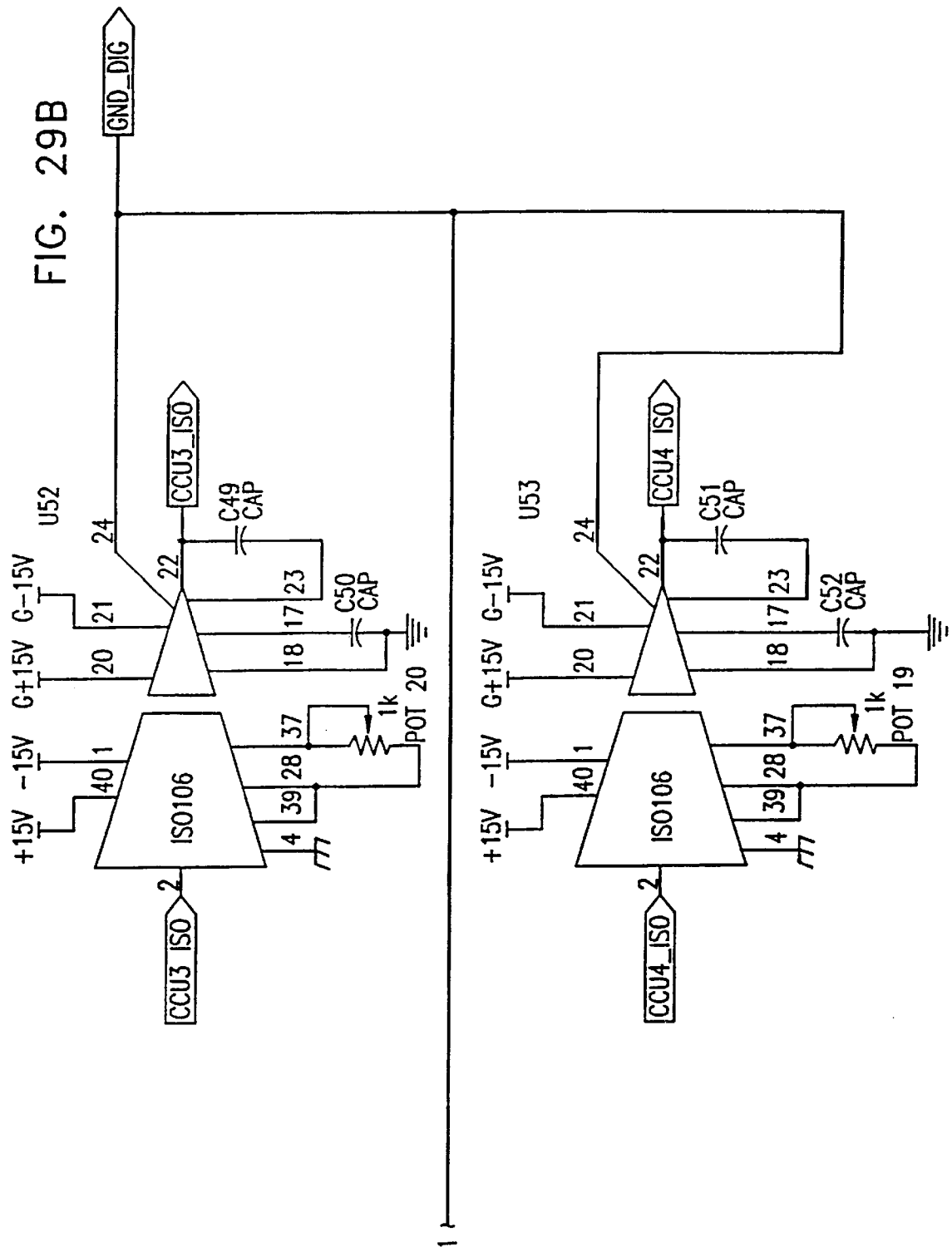

FIG. 23 shows second CCU section 142, including two CCU channels 180 and 182, for generating pacing pulses at predetermined rates and a relative delay therebetween, similar to pacemakers known in the art. FIGS. 24A, 24B and 24C show details of channel 180. FIGS. 25A and 25B show details of channel 182, which is switched by the same switch and counters as channel 180 (shown in FIG. 24B).

Figure 30:
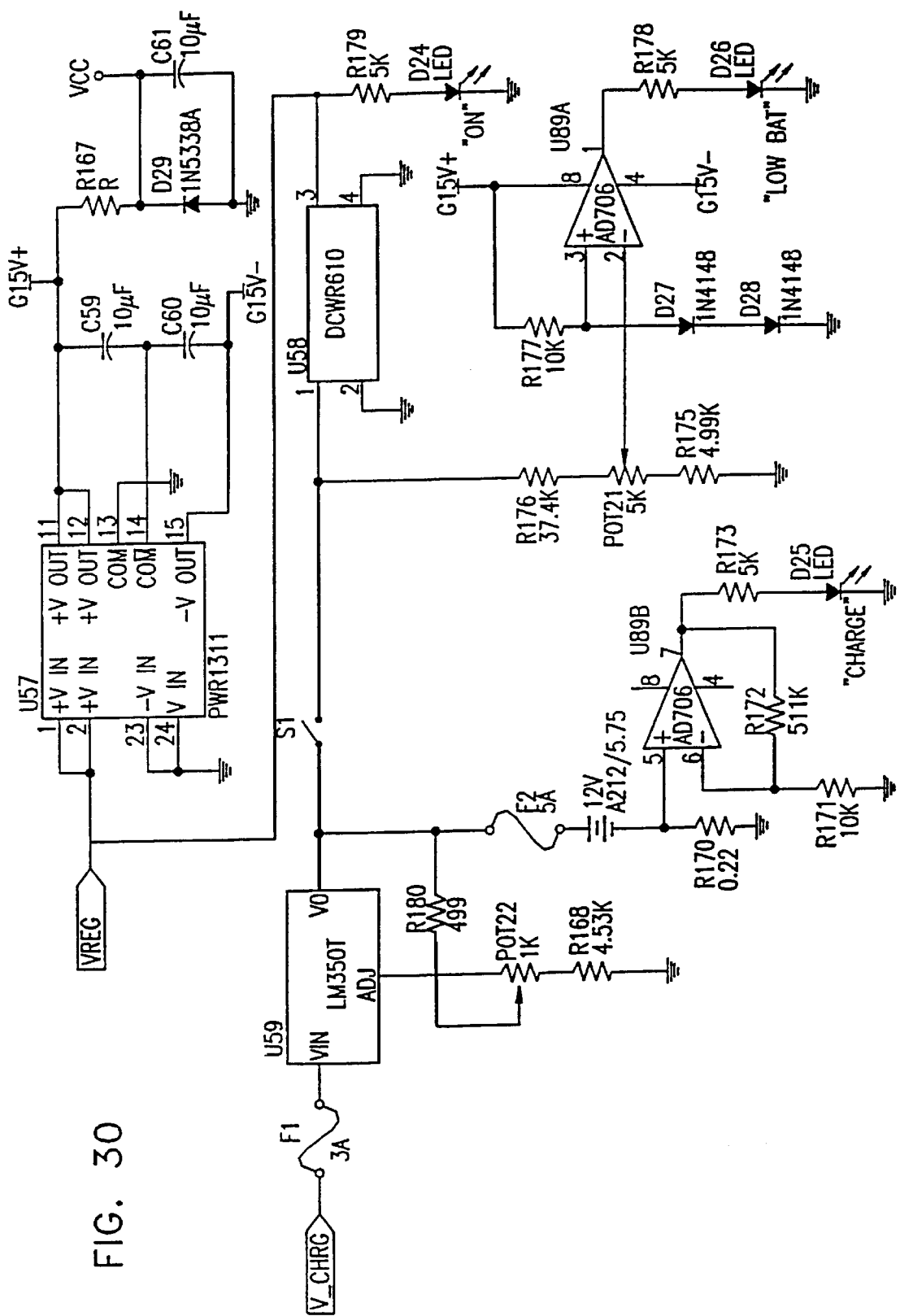
Figure 31:
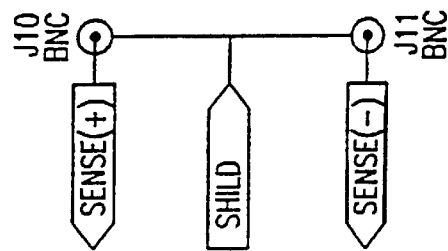
Figure 31:
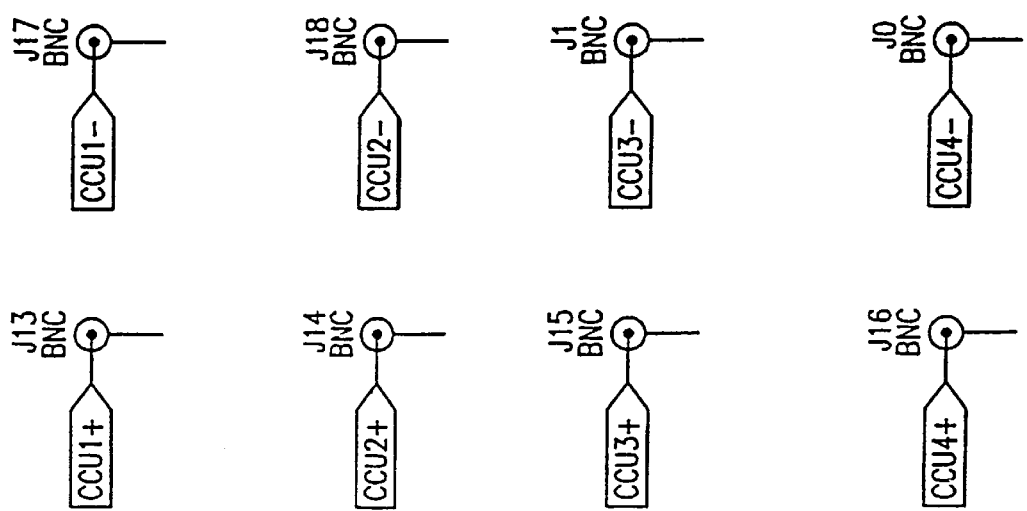
Figure 32:
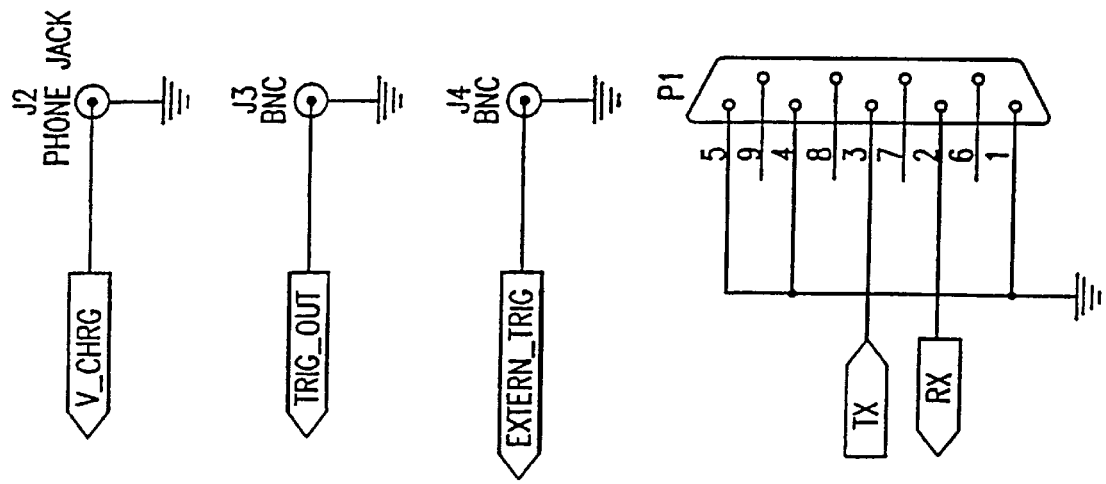
Figure 32:
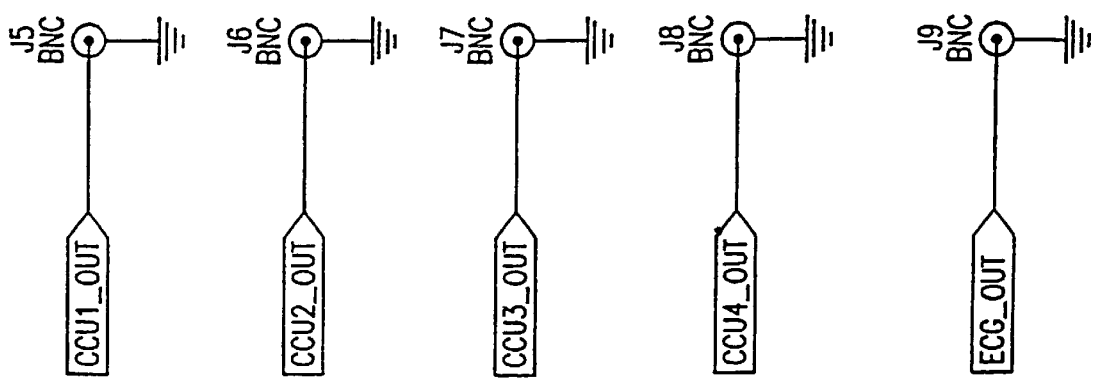

FIGS. 26, 27A, 27B, 28, 29A and 29B show details of isolation circuitry, which is used when circuitry 22 is to be run while connected to external power. FIG. 30 illustrates a battery charging circuit. FIGS. 31 and 32 show front and rear panel connections, respectively.

Although in some of the preferred embodiments described above, as shown in FIG. 1B, for example, circuitry 22 is shown as being contained within an implantable case 32, the specific implementation of the circuitry exemplified by FIGS. 8–32 is better stilted to be contained in an external, bedside case, for example, control unit 27, shown in FIG. 1A, in accordance with the best mode of the invention as it is practiced at present. It will be understood that the circuitry of FIGS. 8–32 can be suitably altered and miniaturized to fit in an implantable case, using methods and electronic devices known in the art, particularly such as are currently used in implantable pacemakers. On the other hand, under some circumstances, non-excitatory stimulation and cardiac output regulation may be best accomplished using such an external, bedside case, when the cardiac output must be regulated temporarily, for example, during recovery from infarction or surgery.

It will be appreciated that the preferred embodiments described above are cited by way of example, and the full scope of the invention is limited only by the claims.

What is claimed is:

1. Apparatus for modifying cardiac output of the heart of a subject, comprising:
   one or more sensors, which sense signals responsive to cardiac activity;
   a stimulation probe comprising one or more stimulation electrodes, which apply non-excitatory stimulation pulses to a cardiac muscle segment; and
   signal generation circuitry, coupled to the one or more sensors and the stimulation probe, which circuitry receives the signals from the one or more sensors and generates non-excitatory stimulation pulses, only at a time at which they are unable to propagate action potentials responsive to the signals,
   wherein the signal generation circuitry identifies an arrhythmia in the signals and controls the stimulation pulses responsive thereto.

2. Apparatus for modifying cardiac output of the heart of a subject, comprising:
   one or more sensors, which sense signals responsive to cardiac activity;
   a stimulation probe comprising one or more stimulation electrodes, which apply non-excitatory stimulation pulses to a cardiac muscle segment; and
   signal generation circuitry, coupled to the one or more sensors and the stimulation probe, which circuitry receives the signals from the one or more sensors and generates the non-excitatory stimulation pulses, responsive to the signals,
   wherein the signal generation circuitry detects a QT interval in the signals and controls the stimulation pulses responsive thereto.

3. Apparatus for modifying cardiac output of the heart of a subject, comprising:
   one or more sensors, which sense signals responsive to cardiac activity;
   a stimulation probe comprising one or more stimulation electrodes, which apply non-excitatory stimulation pulses to a cardiac muscle segment; and
   signal generation circuitry, coupled to the one or more sensors and the stimulation probe, which circuitry receives the signals from the one or more sensors and generates the non-excitatory stimulation pulses, responsive to the signals,
   wherein the one or more stimulation electrodes apply the stimulation pulse to a heart segment having an area of at least 1 $cm^2$.

4. Apparatus according to claim 3, wherein the one or more stimulation electrodes apply the stimulation pulse to a heart segment having an area of at least 4 $cm^2$.

5. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates the non-excitatory stimulation pulses, responsive to the signals, wherein the one or more stimulation electrodes apply the stimulation pulse to a heart segment having an area of at least 5 mm$^2$, and wherein the signal generation circuitry varies the area of the heart segment to which the stimulation pulse is applied.

6. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates non-excitatory stimulation pulses, only at a time at which they are unable to propagate action potentials responsive to the signals, wherein the stimulation probes comprises a net of electrodes.

7. Apparatus according to claim 6, wherein the electrodes in the net are addressable, such that an extent of the segment to which the stimulation pulses is applied is controlled by addressing selected electrodes in the net.

8. Apparatus according to claim 6, wherein the circuitry applies multiple, different stimulation pulses to different ones of the electrodes in the net.

9. Apparatus according to claim 8, wherein the multiple, different stimulation pulses comprises a time sequence of pulses.

10. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates the non-excitatory stimulation pulses, responsive to the signals, wherein the one or more sensors comprise an intracardiac electrode, and wherein the signal generation circuitry synchronizes the stimulation pulse to electrical activity of the heart, and wherein the stimulation probe comprises a hybrid electrode, including the intracardiac electrode together with at least one of the one or more stimulation electrodes.

11. Apparatus according to claim 10, wherein the hybrid electrode comprises a core section including the sensing electrode, enclosed within an annular section including the at least one stimulation electrode.

12. Apparatus according, to claim 11, wherein the annular section comprises a carbon material.

13. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates the non-excitatory stimulation pulses, responsive to the signals, wherein the one or more sensors comprise a hemodynamic sensor, which generates signals responsive to blood flow.

14. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates the non-excitatory stimulation pulses, responsive to the signals, wherein the one or more sensors comprise a hemodynamic sensor, which generates signals responsive to blood oxygenation.

15. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates the non-excitatory stimulation pulses, responsive to the signals, wherein the one or more sensors comprise a hemodynamic sensor, which generates signals responsive to a temperature.

16. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein applying the stimulation probe comprises applying a probe comprising a plurality of stimulation electrodes, and wherein generating and conveying the pulse comprises generating a sequence of pulses and applying each pulse in the sequence to a different one of the plurality of stimulation electrodes.

17. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse only at a time at which it is unable to propagate action potentials responsive to the signal and conveying the pulse to at least one of the one or more electrodes, wherein generating and conveying the pulse comprises detecting a cardiac arrhythmia and adjusting the application of the pulses responsive thereto.

18. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein generating and conveying the pulse comprises detecting a QT interval in the signals and generating pulses responsive thereto.

19. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein the pulse comprises a baseline pulse and a waveform of substantially higher frequency than the baseline pulse superimposed thereon.

20. A method according to claim 8, wherein the waveform comprises a square wave.

21. A method according to claim 8, wherein varying the extent comprises selectively addressing a net of stimulation electrodes implanted in the heart.

22. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein applying the stimulation probe comprises varying the extent of a portion of the area of the heart segment to which the stimulation pulse is applied.

23. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein applying the stimulation probe comprises inserting at least one of the one or more stimulation electrodes into the coronary sinus.

24. A method according to claim 23, wherein inserting the at least one stimulation electrode comprises inserting the electrode into the coronary sinus.

25. A method according to claim 23, wherein sensing the hemodynamic parameter comprises sensing cardiac output, and wherein generating the pulse comprises changing the pulse responsive to the signal to increase the cardiac output.

26. A method according to claim 23, wherein sensing the hemodynamic parameter comprises sensing cardiac output, and wherein generating the pulse comprises changing the pulse responsive to the signal to decrease the cardiac output.

27. A method according to claim 23, wherein sensing the hemodynamic parameter comprises sensing a pressure.

28. A method according to claim 23, wherein sensing the hemodynamic parameter comprises sensing a flow rate.

29. A method according to claim 23, wherein sensing the hemodynamic parameter comprises sensing oxygenation.

30. A method according to claim 23, wherein sensing the hemodynamic parameter comprises sensing a temperature.

31. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing cardiac output, and wherein generating the pulse comprises changing the pulse responsive to the signal to increase the cardiac output.

32. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing cardiac output, and wherein generating the pulse comprises changing the pulse responsive to the signal to decrease the cardiac output.

33. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing a pressure.

34. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing a flow rate.

35. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing oxygenation.

36. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein receiving the signal comprises sensing a temperature.

37. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein generating and conveying the pulse comprises generating and conveying pulses at selected times of day.

38. A method according to claim 37, wherein generating and conveying the pulse comprises generating and conveying pulses at selected times of day.

39. A method according to claim 38, wherein generating and conveying the pulses at selected times of day comprises conveying pulses to increase cardiac output during the subject's waking hours.

40. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse responsive to the signal and conveying the pulse to at least one of the one or more electrodes, wherein conveying the pulses comprises applying pulses to a heart segment having an area of at least 1 $cm^2$.

41. A method according to claim 40, wherein applying the pulses comprises applying pulses to a heart segment having an area of at least 1 $cm^2$.

42. A method according to claim 41, wherein applying the pulses comprises applying pulses to a heart segment having an area of at least 4 $cm^2$.

* * * * *

(12) EX PARTE REEXAMINATION CERTIFICATE (5295th)
United States Patent
Ben-Haim et al.

(10) Number: US 6,298,268 C1
(45) Certificate Issued: Mar. 7, 2006

(54) CARDIAC OUTPUT CONTROLLER

(75) Inventors: Shlomo Ben-Haim, Haifa (IL); Nissim Darvish, Haifa (IL); Yuval Mika, Haifa (IL); Maier Fenster, Petach Tikva (IL)

(73) Assignee: Impulse Dynamics NV, Curacao (AN)

Reexamination Request:
No. 90/006,788, Oct. 10, 2003

Reexamination Certificate for:
Patent No.: 6,298,268
Issued: Oct. 2, 2001
Appl. No.: 09/254,902
Filed: Mar. 12, 1999

(22) PCT Filed: Jul. 9, 1997
(86) PCT No.: PCT/IL97/00235
§ 371 (c)(1),
(2), (4) Date: Mar. 12, 1999
(87) PCT Pub. No.: WO98/10831
PCT Pub. Date: Mar. 19, 1998

Related U.S. Application Data
(60) Provisional application No. 60/026,392, filed on Sep. 16, 1996.

(51) Int. Cl.
*A61N 1/365* (2006.01)

(52) U.S. Cl. .......................................... 607/9
(58) Field of Classification Search ................ 607/1–32
See application file for complete search history.

(56) References Cited

U.S. PATENT DOCUMENTS

| | | | |
|---|---|---|---|
| 3,572,345 A | 3/1971 | Auphan |
| 3,587,567 A | 6/1971 | Schiff |
| 3,651,805 A | 3/1972 | Breiling |
| 3,942,536 A | 3/1976 | Dahl et al. |
| 3,952,750 A | 4/1976 | Mirowski et al. |

(Continued)

FOREIGN PATENT DOCUMENTS

| | | |
|---|---|---|
| EP | 148687 | 7/1985 |
| EP | 314078 A1 | 5/1989 |
| EP | 727241 | 4/1996 |
| JP | 04117967 A2 | 4/1992 |
| JP | 4365493 | 12/1992 |
| JP | 7126600 | 5/1995 |
| JP | 8243176 A2 | 9/1996 |
| WO | WO 92/00716 | 1/1992 |
| WO | WO 95/08316 | 9/1995 |
| WO | WO 9810831 | 9/1996 |
| WO | WO 97/25101 | 1/1997 |
| WO | WO 200004947 | 1/2002 |

OTHER PUBLICATIONS

Antman, E.M. et al. "Treatment of 150 Cases of Life–Threatening Digitalis Intoxication with Digoxin–Specific Fab Antibody Fragments;" Jun. 1990 Circulation; vol. 81: No. 6: pp. 1744–1752.

Antoni, H. et al. "Polarization Effects of Sinusoidal 50–Cycle Alternating Current on Membrane Potential of Mammalian Cardiac Fibers", Pfluegers Arch. 314, pp. 274–291 (1970).

Bach, S.M., Tach Arrhythmia Detection, Implantable Cardioverter Defibrilator Therapy: The Engineering–Clinical Interface, Chapter 15, pp. 303–323, Eds, Mark W. Kroll and Michael H. Lehmann, Kluwer Academic Publishers, USA, 1997.

(Continued)

*Primary Examiner*—Scott Getzow

(57) ABSTRACT

This invention is an apparatus for modifying cardiac output of the heart of a subject, including one or more sensors which sense signals responsive to cardiac activity, and a stimulation probe including one or more stimulation electrodes which apply non-excitatory stimulation pulses to a cardiac muscle segment. Signal generation circuitry is coupled to the one or more sensors and the stimulation probe, which circuitry receives the signals from the one or more sensors and generates the non-excitatory stimulation pulses responsive to the signals.

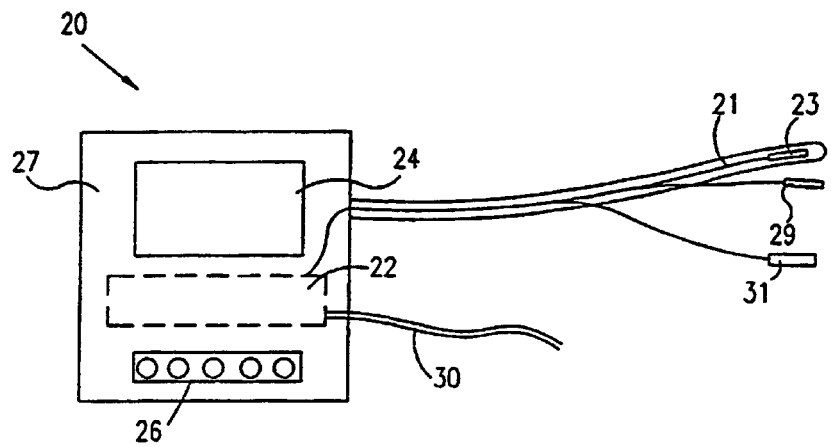

U.S. PATENT DOCUMENTS

| | | |
|---|---|---|
| 4,030,509 A | 6/1977 | Heilman et al. |
| 4,106,494 A | 8/1978 | McEachern |
| 4,164,216 A | 8/1979 | Person |
| 4,184,493 A | 1/1980 | Mower et al. |
| 4,202,340 A | 5/1980 | Mower et al. |
| 4,223,678 A | 9/1980 | Mower |
| 4,237,895 A | 12/1980 | Johnson |
| 4,273,114 A | 6/1981 | Berkalow et al. |
| 4,312,354 A | 1/1982 | Walters |
| 4,316,472 A | 2/1982 | Mower et al. |
| 4,384,585 A | 5/1983 | Zipes |
| 4,387,717 A | 6/1983 | Brownlee |
| 4,403,614 A | 9/1983 | Engle et al. |
| 4,407,288 A | 10/1983 | Mirowski et al. |
| 4,440,172 A | 4/1984 | Langer |
| 4,506,680 A | 3/1985 | Stokes |
| 4,543,738 A | 10/1985 | Hellman et al. |
| 4,543,956 A | 10/1985 | Herscovici |
| 4,554,922 A | 11/1985 | Prystowsky et al. |
| 4,559,946 A | 12/1985 | Mower |
| 4,559,947 A | 12/1985 | Renger et al. |
| 4,566,456 A | 1/1986 | Koning |
| 4,572,191 A | 2/1986 | Langer et al. |
| 4,628,934 A | 12/1986 | Pohndorf et al. |
| 4,651,716 A | 3/1987 | Forester |
| 4,674,508 A | 6/1987 | DeCote |
| 4,679,572 A | 7/1987 | Baker, Jr. |
| 4,690,155 A | 9/1987 | Hess |
| 4,726,379 A | 2/1988 | Altman et al. |
| 4,765,341 A | 8/1988 | Mower et al. |
| 4,830,006 A | 5/1989 | Haluska et al. |
| 4,928,688 A | 5/1990 | Mower |
| 4,971,058 A | 11/1990 | Pless et al. |
| 4,979,507 A | 12/1990 | Heinz et al. |
| 4,998,531 A | 3/1991 | Bocchi et al. |
| 5,003,976 A | 4/1991 | Alt |
| 5,020,544 A | 6/1991 | Dahl et al. |
| 5,022,396 A | 6/1991 | Watanabe |
| 5,044,375 A | 9/1991 | Bach, Jr. et al. |
| 5,083,564 A | 1/1992 | Scherlag |
| 5,085,218 A * | 2/1992 | Heil et al. .................. 600/373 |
| 5,087,243 A | 2/1992 | Avitall |
| 5,097,832 A | 3/1992 | Buchanan |
| 5,111,815 A | 5/1992 | Mower |
| 5,129,394 A | 7/1992 | Mehra |
| 5,137,021 A | 8/1992 | Wayne et al. |
| 5,154,501 A | 10/1992 | Svenson |
| 5,156,147 A | 10/1992 | Warren et al. |
| 5,156,149 A | 10/1992 | Hudrlik |
| 5,161,527 A | 11/1992 | Nappholz |
| 5,163,428 A | 11/1992 | Pless |
| 5,172,699 A | 12/1992 | Svenson et al. |
| 5,184,620 A | 2/1993 | Cudahy et al. |
| 5,199,428 A | 4/1993 | Obel et al. |
| 5,205,284 A | 4/1993 | Freeman |
| 5,213,098 A | 5/1993 | Bennett et al. |
| 5,236,413 A | 8/1993 | Feiring |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,305,745 A | 4/1994 | Zacouto |
| 5,320,642 A | 6/1994 | Scherlag |
| 5,320,643 A | 6/1994 | Roline et al. |
| 5,324,327 A * | 6/1994 | Cohen .................. 607/122 |
| 5,327,887 A | 7/1994 | Nowakowski |
| 5,346,506 A | 9/1994 | Mower et al. |
| 5,353,800 A | 10/1994 | Pohndorf |
| 5,366,486 A | 11/1994 | Zipes et al. |
| 5,368,040 A | 11/1994 | Carney |
| 5,370,665 A | 12/1994 | Hudrlik |
| 5,386,837 A | 2/1995 | Sterzer |
| 5,387,419 A | 2/1995 | Levy |
| 5,391,192 A | 2/1995 | Lu |
| 5,391,199 A | 2/1995 | Ben-Haim |
| 5,398,683 A | 3/1995 | Edwards |
| 5,415,629 A | 5/1995 | Henley |
| 5,417,717 A | 5/1995 | Salo et al. |
| 5,419,763 A | 5/1995 | Hildebrand |
| 5,425,363 A | 6/1995 | Wang |
| 5,433,730 A * | 7/1995 | Alt .............................. 607/5 |
| 5,443,485 A | 8/1995 | Housworth |
| 5,443,489 A | 8/1995 | Ben-Haim |
| 5,447,520 A | 9/1995 | Spano |
| 5,458,568 A | 10/1995 | Racchini et al. |
| 5,464,020 A | 11/1995 | Lerner |
| 5,468,254 A | 11/1995 | Hahn |
| 5,472,453 A | 12/1995 | Alt |
| 5,476,484 A | 12/1995 | Hedberg |
| 5,476,485 A | 12/1995 | Weinberg et al. |
| 5,476,497 A | 12/1995 | Mower |
| 5,482,052 A | 1/1996 | Lerner |
| 5,499,971 A | 3/1996 | Shapland et al. |
| 5,501,662 A | 3/1996 | Hofman |
| 5,514,162 A | 5/1996 | Bornzin et al. |
| 5,520,642 A | 5/1996 | Bigagli et al. |
| 5,531,764 A | 7/1996 | Adams et al. |
| 5,540,722 A | 7/1996 | Clare |
| 5,549,646 A | 8/1996 | Katz et al. |
| 5,556,421 A | 9/1996 | Prutchi |
| 5,568,809 A | 10/1996 | Ben-Haim |
| 5,571,143 A | 11/1996 | Hoegnelid et al. |
| 5,584,803 A | 12/1996 | Stevens |
| 5,584,868 A | 12/1996 | Salo et al. |
| 5,587,200 A | 12/1996 | Lorenz |
| 5,601,609 A | 2/1997 | Duncan |
| 5,601,611 A | 2/1997 | Fayram et al. |
| 5,626,622 A | 5/1997 | Cooper |
| 5,634,899 A | 6/1997 | Shapland et al. |
| 5,649,966 A | 7/1997 | Noren et al. |
| 5,651,378 A | 7/1997 | Matheny |
| 5,662,687 A | 9/1997 | Hedberg et al. |
| 5,674,251 A | 10/1997 | Combs et al. |
| 5,674,259 A | 10/1997 | Gray |
| 5,683,431 A | 11/1997 | Wang |
| 5,687,734 A | 11/1997 | Dempsey et al. |
| 5,713,935 A | 2/1998 | Prutchi et al. |
| 5,720,768 A | 2/1998 | Verboven-Nelissen |
| 5,735,876 A | 4/1998 | Kroll et al. |
| 5,738,096 A | 4/1998 | Ben Haim |
| 5,738,105 A | 4/1998 | Kroll |
| 5,749,906 A | 5/1998 | Kieval et al. |
| 5,755,740 A | 5/1998 | Nappholz |
| 5,782,876 A | 7/1998 | Flammang |
| 5,782,881 A | 7/1998 | Lu et al. |
| 5,792,198 A | 8/1998 | Nappholz |
| 5,792,208 A | 8/1998 | Gray |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,865,787 A | 2/1999 | Shapland et al. |
| 5,906,607 A | 5/1999 | Taylor et al. |
| 5,913,876 A | 6/1999 | Taylor et al. |
| 5,927,284 A | 7/1999 | Borst et al. |
| 6,032,074 A | 2/2000 | Collins |
| 6,032,672 A | 3/2000 | Taylor |
| 6,041,252 A | 3/2000 | Walker et al. |
| 6,071,305 A | 6/2000 | Brown et al. |
| 6,086,582 A | 7/2000 | Altman et al. |

| | | |
|---|---|---|
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,295,470 B1 | 9/2001 | Mower |
| 6,337,995 B1 | 1/2002 | Mower |
| 6,341,235 B1 | 1/2002 | Mower |
| 6,343,232 B1 | 1/2002 | Mower |
| 6,411,847 B1 | 6/2002 | Mower |
| RE38,119 E | 5/2003 | Mower |

OTHER PUBLICATIONS

Bakker, P.F., et al., "Beneficial Effects of Biventricular Pacing of Congestive Heart Failure", PACE, vol. 17, Apr. 1994, Part 11, one page.

Bakker, P.F., et al., "Biventricular Pacing Improves Functional Capacity in Patients with End–Stage Congestive Heart Failure" PACE, vol. 17, Apr. 1995, Part 11, one page.

Bargheer K. et al., "Prolongation of Monophasic Action Potential Duration and the Refractory Period in the Human Heart by Tedisamil, a New Potassium–Blocking Agent", J. Eur Heart 15 (10), Oct. 1994, pp. 1409–1414.

Bers, D.M., Excitation–Contraction Coupling and Cardiac Contractile Force, Kluwer Academic Publishers, London, 1993.

Borst, et al. "Coronary Artery Bypass Grafting Without Cardiopulomonary Bypass and Without Interuption of Native Coronary Flow Using a Novel Anastomosis site restraining device ('Octopus')", Journal of the American College of Cardiology, 27 (6), May 1996.

Cano, N.J. et al. "Dose–Dependent Reversal of Digoxin–Inhibited Activity of an In–Vitro NA+K+ATPase Model by Digoxin–Specific Antibody;" May 1996; pp. 107–1011; Toxicology Letters; vol. 85; No. 2.

Cazeau S. et al., "Multisite Pacing for End–Stage Heart Failure: Early Experience", Pacing and Clinical Electrophysiology vol. 19, No. 1996, Part 11, pp. 1748–1757.

Cooper, W., "Postextrasystolic Potentiation: Do We Really Know What It Means and How to Use It?" Circulation, vol. 88, No. 6, Dec. 1993, pp. 2962–2971.

Dillon, SM., "Optical Recordings in the Rabbit Heart Show that Defibrillation Strength Shocks Prolong the Duration of Depolarization and the Refractory Period" in Circ Res., 69 (3), Sep. 1991, pp. 842–856.

Dillon, SM., abstract of "Sychronized Repolarization After Defibrillation Shocks. A Possible Component of the Defibrillation Process Demonstration By Optical Recordings in Rabbit Heart", Circulation, May 1992, vol. 85, No. 5, pp. 1865–1878.

Fain, E.S., et al. "Improved Internal Defibrillation Efficacy with a Biphasic Waveform", American Heart Journal 117 (2), Feb. 1989, pp. 358–364.

Fleg, J.L. et al., "Impact of Age on the Cardiovasvular Response to Dynamic Upright Exercise in Healthy Men and Women", J. Appl. Physiol., vol. 78, 1995, p. 890.

Foster, A.H, et al., "Acute Hemodynamic Effects of Atrio–Biventricular Pacing in Humans", 1995, The Society of Thoracic Surgeons vol. 59, pp. 294–299.

Franz, M.R., "Bridging the Gap Between Basic and Clinical Electrophysiology: What Can be Learned from Monophasic Action Potential Recordings?", J. Cardiovasc Electrophysiol 5(8), Aug. 1994, pp. 699–710.

Franz, M.R., "Method and Theory of Monophasic Action Potential Recording", Prog. Cardiovasc Dis 33 (6), May–Jun. 1991, pp. 347–368.

Franz, M.R., "Progress in Cardiovascular Disease: Monophasic Action Potential Symposium, I. Introduction", Prog. Cardiovasc Dis 33 (6), May–Jun. 1991 pp. 345–346.

Fromer et al., "Ultrarapid Subthreshold Stimulation for Termination of Atrioventricular Node Reentrant Tachycardia", Journal of the American College of Cardiology 20 (Oct. 1992), pp. 879–883.

Fu. P and B.J. Bardakjian, "System Identification of Electrically Coupled Smooth Muscle Cells: The Passive Electrically Coupled Smooth Muscle Cells: The Passive Electrical Properties", published in IEEE Transactions on Biomedical Engineering, 38(11), pp. 1130–1140, 1991.

Ham, Frederic M and Han, Soowhan, "Classification of Cardiac Arrhythmias Using Fuzzy Artmap"; IEEE Transactions on Biomedical Engineering, vol. 43, No. 4, Apr. 1996.

Hoffman, B.F. et al., "Effects of Postextrasystolic Potentiation on Normal & Failing Hearts", Bulletin of New York Academy of Medicine, 41 in 1965, pp. 498–534.

Josephson, M.E., Clinical Cardiac Electrophysiology: Techniques and Interpretations, 2nd. Edition, Lea & Febiger, Philadelphia, 1991.

King, A. et al., The Inotropic Action of Paired Pulse Stimulation in the Normal and Failing Heart: An Experimental Study, Cardiovascular Research, vol. 2, Apr. 1968, pp. 122–129.

Knisley et al., "Prolgongation and Shortening of Action Potentials by Electrical Shocks in Frog Ventricular Muscle", American Journal of Physiology 6 (Heart Circ. Physiol. 35, 1994) pp. H2348–H2358.

Koller, et al., "Relation Between Repolarization and Refractoriness During Programmed Electrical Stimulation in the Human Right Ventricle", Circulation 91(9), 2378–2384, 1995.

Langberg, Jonathan J. et al., "Identification of Ventricular Tachycardia with Use of the Morphology of the Endocardial Electrogram", Circulation, vol. 77, No. 6, Jun. 1988.

McVeigh, E.R et al., "Noninvasive Measurement of Transmural Gradients in Myocardial Strain with MR Imaging", Radiology 180 (3), Sep. 1991, pp. 677, 679–684.

Mercando, A.D., et al., "Automated Detection of Tachardias by Antitachicardia Devices", Chapter 100, pp. 943–948, in Cardiac Electrophysiology from Cell to Bedside, Eds. Douglas P. Zipes and Jose Jalife, publishers W.B. Saunders Company (1990).

Moran, R.J. et al; "Digoxin–Specific Fab Fragments Impair Renal Function in the Rat:" 1994; pp. 854–856; Journal of Pharmacy and Pharmacology; vol. 46: No 10.

Morse, et al., "A Guide to Cardiac Pacemakers,Defibrillators and Related Products", Droege Computing Services, Durham, NC.

Merck Manual, The, Section 3, the 16th Edition of the Merck Manual, Published in 1992.

Paul, VE., et al. "Automatic Recognition of Ventricular Arrythmias Using Temporal Electrogram Analysis" PACE, vol. 14, pp. 1265–1273, (1991).

Quizhen Xue et al., "Neural–Network–Based Adaptive Matched Filtering for QRS Detection", IEEE Transactions on Biomedical Engineering, vol. 39, No. 4, Apr. 1992.

Saksena et al., "Dual–site Atrial Pacing in Atrial Fibrillation", JACC, vol. 28, No. 3, Sep. 1996, pp. 687–694.

Shumaik, G.M. et al, "Oleander Poisoning; Treatment with Digoxin–Specific Fab Antibody Fragments;" Jul. 1988; pp. 732–735; Annals of Emergency Medicine; vol. 17; No. 7.

Sweeny RJ, et al., abstract of "Countershock Strength–Duration Relationship for Myocardial Refractory Period Extension", Acad Emerg. Med., Jan. 1995, vol. 2, No. 1, pp. 57–62.

Sweeny RJ, et al., abstract of "Refractory Interval After Transcardiac Shocks During Ventricular Fibrillation", Circulation, Dec. 1996, vol. 94, No. 11, pp. 2947–2952.

Sweeny RJ, et al., abstract of "Ventricular Refractory Period Extension Caused by Defibrillation Shocks", Circulation, Sep. 1990, vol. 82, No. 3, pp. 965–972.

Talit, U. et al., "The Effect of External Cardiac Pacing on Stroke Volume", Pace 13, May 1990, pp. 598–560.

Tsong, T.Y., "Electroportion of Cell Membranes" Aug. 1991; pp. 297–306; Biophysical Journal; vol. 60.

Verrier, et al, "Electrophysiologic Basis for T Wave Alternans as an Indeox of Vulnerability to Ventricular Fibrillation" Journal of Cardiovascular Electrophysiology, vol. 5, pp. 445–461, 1994.

Webster, John G., ed., Design of Cardiac Pacemakers, IEEE Press, Piscataway, New Jersey, 1995.

Wessale, J.L. et al., "Stroke Volume and Three Phase Cardiac Output Rate Relationship with Ventricular Pacing" Pace 13, May 1990, pp. 673–680.

Wirtzfeld, A. et al., "Physiological Pacing: Present Status and Future Developments", Pace 10 Jan.–Feb. 1987, Part I, pp. 41–57.

Zipes, D et al., Cardiac Electrophysiology from Cell to Bedside, 1990, W.B. Saunders Co., Philadelphia.

Guidant Product Catalogue, 2001, 2 pages.

"The Latest Tetralogy of Fallot Discussion with Graphical Support Including Video of Echocardiography and Catherization" Pediatric Electrophysiologypicu Book ("An On–Line Resource for Pediatric Critical Care").

Brumwell D.A. et al. "The Amplifier Sensing the Depolarization", Implantable Cardioverter Defibrillator Therapy: The Engineering–Clinical Interface, Chapt. 14, pp. 275–302, Eds. Kroll and Lehmann, Kluwer Academic Publishers, USA 1997.

Gill RJ, et al., abstract of "Refractory Period Extension During Ventricular Pacing at Fibrillatory Pacing Rates" Pacing Clin. Elctrophysiol, Mar. 1997, vol. 20, No. 3, pp. 647–653.

Hardage, M.L. and Sweeney, M.B., "Anti–Tachycardia Pacing and Cardioversion", Implantable Cardiovertre Defibrilator Therapy: The Engineering–Clinical Interface, Chapt. 6, pp. 325–342, Eds. Mark W. Kroll and Michael H. Lehmann, Kluwer Academic Publishers U.S.A 1997.

Matheny R.G. and C.J. Shaar, "Vagus Nerve Stimulation as a Method to Temporarily Slow or Arrest the Heart" Annals of Thoracic Surgery. 63 (6) Supplement, pp. S28–29, Jun. 1997.

Supino, C.G., "The System", Implantable Cardioverter Defibrillator Therapy: The Engineering–Clinal Interface, Chapt. 8, pp. 163–172, Eds. Mark W. Kroll and Michael H. Lehmann, Kluwer Academic Publishers, USA 1997.

Thakor et al., "Effect of Varying Pacing Waveform Shapes on Propagation and Hemodynamics in the Rabbit Heart", The Americal Journal of Cardiology 79 (6A), pp. 36–43, 1997.

* cited by examiner

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2–5, 10, 13–16, 18, 19 and 22–42 is confirmed.

Claims 1, 6–8, 11 and 17 are determined to be patentable as amended.

Claims 9, 12, 20 and 21, dependent on an amended claim, are determined to be patentable.

New claims 43–64 are added and determined to be patentable.

1. Apparatus for modifying cardiac output of the heart of a subject, comprising:
   one or more sensors, which sense signals responsive to cardiac activity;
   a stimulation probe comprising one or more stimulation electrodes, which apply non-excitatory stimulation pulses to a cardiac muscle segment; and
   signal generation circuitry, coupled to the one or more sensors and the stimulation probe, which circuitry receives the signals from the one or more sensors and generates non-excitatory stimulation pulses, only at a time at which they are unable to propagate action potentials responsive to the signals,
   wherein the signal generation circuitry identifies an arrhythmia in the signals and controls the stimulation pulses responsive thereto *and wherein said non-excitatory stimulation pulses are capable of modifying cardiac output also in a non-arrhythmic heart.*

6. Apparatus for modifying cardiac output of the heart of a subject, comprising:
   one or more sensors, which sense signals responsive to cardiac activity;
   a stimulation probe comprising one or more stimulation electrodes, which apply non-excitatory stimulation pulses to a cardiac muscle segment; and
   signal generation circuitry, coupled to the one or more sensors and the stimulation probe, which circuitry receives the signals from the one or more sensors and generates non-excitatory stimulation pulses, only at a time at which they are unable to propagate action potentials responsive to the signals,
   wherein the stimulation probes comprises a net of electrodes, *at least two electrodes of which can be electrified at different times from each other.*

7. Apparatus according to [claim] *any of claims* 6, *and 47–49*, wherein the electrodes in the net are addressable, such that an extent of the segment to which the stimulation pulses is applied is controlled by addressing selected electrodes in the net.

8. Apparatus according to [claim] *any of claims* 6, *and 47–49*, wherein the circuitry applies multiple, different stimulation pulses to different ones of the electrodes in the net.

11. Apparatus according to [claim] *any of claims* 10 *and 50–52*, wherein the hybrid electrode comprises a core section including the sensing electrode, enclosed within an annular section including the at least one stimulation electrode.

17. A method for modifying cardiac output, comprising:
   applying a stimulation probe comprising one or more stimulation electrodes to a subject's heart;
   receiving a signal from at least one sensor responsive to the subject's cardiac muscle activity; and
   generating a non-excitatory stimulation pulse only at a time at which it is unable to propagate action potentials responsive to the signal and conveying the pulse to at least one of the one or more electrodes,
   wherein generating and conveying the pulse comprises detecting a cardiac arrhythmia and adjusting the application of the pulses responsive thereto *and wherein said non-excitatory stimulation pulses are capable of modifying cardiac output also in a non-arrhythmic heart.*

*43. Apparatus for modifying cardiac output of the heart of a subject, comprising:*
   *one or more sensors, which sense signals responsive to cardiac activity, at least one of said sensors sensing other than electrical activity of the heart;*
   *a stimulation probe comprising one or more stimulation electrodes, which apply non-excitatory stimulation pulses to a cardiac muscle segment; and*
   *signal generation circuitry, coupled to the one or more sensors and the stimulation probe, which circuitry receives the signals from the one or more sensors including from said at least one of said sensors and generates non-excitatory stimulation pulses, only at a time at which they are unable to propagate action potentials responsive to the signals,*
   *wherein the signal generation circuitry identifies an arrhythmia in the signals and controls the stimulation pulses responsive thereto.*

*44. A method for modifying cardiac output, comprising:*
   *applying a stimulation probe comprising one or more stimulation electrodes to a subject's heart;*
   *receiving a signal from at least one sensor responsive to the subject's cardiac muscle activity, at least one of said at least one sensor sensing other than electrical activity of the heart; and*
   *generating a non-excitatory stimulation pulse only at a time at which it is unable to propagate action potentials responsive to the signal including from said at least one of said at least one sensor conveying the pulse to at least one of the one or more electrodes,*
   *wherein generating and conveying the pulse comprises detecting a cardiac arrhythmia and adjusting the application of the pulses responsive thereto.*

*45. Apparatus for modifying cardiac output of the heart of a subject, comprising:*
   *one or more sensors, which sense signals responsive to cardiac activity;*
   *a stimulation probe comprising one or more stimulation electrodes, which apply non-excitatory stimulation pulses to a cardiac muscle segment; and*
   *signal generation circuitry, coupled to the one or more sensors and the stimulation probe, which circuitry* receives the signals from the one or more sensors and generates non-excitatory stimulation pulses, only at a time at which they are unable to propagate action potentials responsive to the signals and at which time they are unable to prevent propagation of an action potential, wherein the signal generation circuitry identifies an arrhythmia in the signals and controls the stimulation pulses responsive thereto.

46. A method for modifying cardiac output, comprising:

applying a stimulation probe comprising one or more stimulation electrodes to a subject's heart;

receiving a signal from at least one sensor responsive to the subject's cardiac muscle activity; and generating a non-excitatory stimulation pulse only at a time at which it is unable to propagate action potentials responsive to the signal and conveying the pulse to at least one of the one or more electrodes and at which time they are unable to prevent propagation of an action potential, wherein generating and conveying the pulse comprises detecting a cardiac arrhythmia and adjusting the application of the pulses responsive thereto.

47. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates non-excitatory stimulation pulses, only at a time at which they are unable to propagate action potentials responsive to the signals, wherein said non-excitatory stimulation pulses are capable of modifying cardiac output also in a non-arrhythmic heart and wherein the stimulation probes comprises a net of electrodes.

48. Apparatus for modifying cardiac output of the heart of a subject, comprising:

one or more sensors, which sense signals responsive to cardiac activity, at least one of said sensors sensing other than electrical activity of the heart;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors including from said at least of said sensors and generates non-excitatory stimulation pulses, only at a time at which they are unable to propagate action potentials responsive to the signals, wherein the stimulation probes comprises a net of electrodes.

49. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors and generates non-excitatory stimulation pulses, only at a time at which they are unable to propagate action potentials responsive to the signals and at which time they are unable to prevent propagation of an action potential, wherein the stimulation probes comprises a net of electrodes.

50. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment, wherein said non-excitatory stimulation pulses are capable of modifying cardiac output also in a non-arrhythmic heart; and signal generation circuitry, coupled to the one or more sensors and the stimulation probe, which circuitry receives the signals from the one or more sensors and generates the non-excitatory stimulation pulses, responsive to the signals, wherein the one or more sensors comprise an intracardiac electrode, and wherein the signal generation circuitry synchronizes the stimulation pulse to electrical activity of the heart, and wherein the stimulation probe comprises a hybrid electrode, including the intracardiac electrode together with at least one of the one or more stimulation electrodes.

51. Apparatus for modifying cardiac output of the heart of a subject, comprising:

one or more sensors, which sense signals responsive to cardiac activity, at least one of said sensors sensing other than electrical activity of the heart;

a stimulation probe comprising one or more stimulation electrodes, which apply non-excitatory stimulation pulses to a cardiac muscle segment; and signal generation circuitry, coupled to the one or more sensors and the stimulation probe, which circuitry receives the signals from the one or more sensors including from said at least one of said sensors and generates the non-excitatory stimulation pulses, responsive to the signals, wherein the one or more sensors comprise an intracardiac electrode, and wherein the signal generation circuitry synchronizes the stimulation pulse to electrical activity of the heart, and wherein the stimulation probe comprises a hybrid electrode, including the intracardiac electrode together with at least one of the one or more stimulation electrodes.

52. Apparatus for modifying cardiac output of the heart of a subject, comprising:

one or more sensors, which sense signals responsive to cardiac activity;

a stimulation probe comprising one or more stimulation electrodes, which apply non-excitatory stimulation pulses to a cardiac muscle segment at which time they are unable to prevent propagation of an action potential; and signal generation circuitry, coupled to the one or more sensors and the stimulation probe, which circuitry receives the signals from the one or more sensors and generates the non-excitatory stimulation pulses, responsive to the signals, wherein the one or more sensors comprise an intracardiac electrode, and wherein the signal generation circuitry synchronizes the stimulation pulse to electrical activity of the heart, and wherein the stimulation probe comprises a hybrid electrode, including the intracardiac electrode together with at least one of the one or more stimulation electrodes.

53. A method according to claim 37, wherein said generating and conveying is applied only at said selected times.

54. A method according to claim 37, wherein said generating and conveying is applied even in the event of an arrhythmia.

55. Apparatus according to any of claims 1–6, 9–10, 12–15, 45, 47, 49, 50, and 52, wherein a signal from at least one sensor of other than electrical activity is used for generating said pulses.

56. A method according to any of claims 16–42, 46, 53, and 54, wherein a signal from at least one sensor of other than electrical activity is used for generating said pulses.

57. Apparatus according to any of claims 1–6, 9–10, 12–15, 43, 47, 48, 50, and 51, wherein said non-excitatory pulses are generated at a time at which they are unable to prevent the propagation of action potentials.

58. A method according to any of claims 16–42, 44, 53, and 54, wherein said non-excitatory pulses are generated at a time at which they are unable to prevent the propagation of action potentials.

59. Apparatus according to any of claims 2–6, 9–10, 12–15, 43, 45,48, 49, 51, and 52, wherein said non-excitatory stimulation pulses are capable of modifying cardiac output also in a non-arrhythmic heart.

60. A method according to any of claims 16, 18–42, 44, 46, 53, and 54, wherein said non-excitatory stimulation pulses are capable of modifying cardiac output also in a non-arrhythmic heart.

61. Apparatus according to any of claims 1–6, 9–10, 12–15, 43, 45, and 47–52, configured to increase cardiac output.

62. Apparatus according to any of claims 1–6, 9–10, 12–15, 43, 45, and 47–52, configured to reduce cardiac output.

63. A method according to any of claims 16–42, 44, 46, 53, and 54, wherein said method increases cardiac output.

64. A method according to any of claims 16–42, 44, 46, 53, and 54, wherein said method reduces cardiac output.

\* \* \* \* \*